(12) United States Patent
Gillespie et al.

(10) Patent No.: US 6,184,182 B1
(45) Date of Patent: Feb. 6, 2001

(54) COMPOSITION AND METHOD FOR TREATING PLANTS WITH EXOGENOUS CHEMICALS

(75) Inventors: Jane L. Gillespie, St. Louis; Anthony J. I. Ward, Clayton, both of MO (US)

(73) Assignee: Monsanto Company, St. Louis, MO (US)

( * ) Notice: Under 35 U.S.C. 154(b), the term of this patent shall be extended for 0 days.

(21) Appl. No.: 08/957,750

(22) Filed: Oct. 24, 1997

Related U.S. Application Data
(60) Provisional application No. 60/029,317, filed on Oct. 25, 1996, provisional application No. 60/034,887, filed on Jan. 31, 1997, and provisional application No. 60/039,789, filed on Mar. 4, 1997.

(51) Int. Cl.$^7$ ................................................ A01N 25/30
(52) U.S. Cl. ..................... 504/116; 504/206; 504/235; 504/250; 514/561; 514/563; 514/772
(58) Field of Search ................... 504/116, 206, 504/235, 250; 514/561, 563, 772

(56) References Cited

U.S. PATENT DOCUMENTS

| | | | |
|---|---|---|---|
| 4,834,908 | 5/1989 | Hazen | 252/356 |
| 4,944,791 | 7/1990 | Schröder | 71/92 |
| 5,180,416 | 1/1993 | Katou | 504/136 |
| 5,308,827 | * 5/1994 | Sakamoto et al. | 504/206 |
| 5,310,724 | 5/1994 | Kondo | 504/273 |
| 5,466,458 | 11/1995 | Martin | 424/405 |
| 5,466,659 | 11/1995 | Keeney | 504/130 |
| 5,512,079 | 4/1996 | Jahnke | 71/64.08 |
| 5,558,806 | 9/1996 | Policello | 252/355 |
| 5,580,567 | 12/1996 | Roberts | 424/405 |

FOREIGN PATENT DOCUMENTS

| | | | |
|---|---|---|---|
| 60702/94 | 7/1995 | (AU). | |
| 2081254 | 4/1993 | (CA). | |
| 2099631 | 1/1994 | (CA). | |
| 32 47 050 | 6/1984 | (DE) | A01N/25/30 |
| 4 318 673 | 1/1995 | (DE). | |
| 0 019 384 | 11/1980 | (EP). | |
| 0 146 238 | 6/1985 | (EP). | |
| 0 204 146 | 12/1986 | (EP). | |
| 0 206 537 | 12/1986 | (EP) | A01N/57/20 |
| 0 342 685 | 11/1989 | (EP). | |
| 0 433 577 | 6/1991 | (EP). | |
| 0 485 207 | 5/1992 | (EP) | A01N/25/04 |
| 0 556 649 | 8/1993 | (EP). | |
| 0 579 052 | 1/1994 | (EP) | A01N/25/02 |
| 0 648 413 | 4/1995 | (EP). | |
| 0 664 954 | 8/1995 | (EP). | |
| 0 729 700 | 9/1996 | (EP). | |
| 67 542 | 4/1995 | (HU). | |
| 58-124703 | 7/1983 | (JP). | |
| 2-169545 | 6/1990 | (JP). | |
| 2-169546 | 6/1990 | (JP). | |
| 2-172950 | 7/1990 | (JP). | |
| 2-172951 | 7/1990 | (JP). | |
| 4-134001 | 5/1992 | (JP). | |
| 5-065201 | 3/1993 | (JP). | |

(List continued on next page.)

OTHER PUBLICATIONS

Gaskin, R. E. et al., Some Physicochemical Factors Influencing Foliar Uptake Enhancement of Glyphosate–Mono(Isopropylammonium)by Polyoxyethylene Surfactants: *Pesticide Science*, vol. 34, No. 3, pp. 195–206, Jan. 1992, XP000287976.

Wyrill, J.B., et al., "Glyphosate Toxicity to Common Milkweed and Hemp Dogbane as Infrluenced by Surfactants," *Weed Science*; vol. 25, No. 3, pp. 275–287, May 1997, XP002034447.

Anon. (no date). LI–700. Brochure of Agridyne, Pont–du–Casse, France.

Anon. (1993). 40 CFR §180.1001, 435–458.

Anon. (1997). Crop protection round–up: adjuvants. Farm Chemicals, Mar. 1997, 56–57.

Bravais et al. (1993). Influence of triolein and methyl, ethyl and propyl oleate on the deposit shape and the foliar penetration of phenmedipham and quizalofop–ethyl. Mededelingen Faculteit Landbouwwetenschappen Rijksuniversiteit Gent 58(3a), 803–807.

Bruce et al. (1993). Absorption and activity of nicosulfuron and primisulfuron in quackgrass (*Elytrigia repens*) as affected by adjuvants. Weed Science 41, 281–224.

De Villiers et al. (1996). Optimizing tralkoxydim efficacy with carrier water high in sodium bicarbonate. FRI Bulletin 193 (Proceedings, Fourth International Symposium on Adjuvants for Agrochemicals, 1995), 207–210.

Eberlein et al. (1992). Hairy nightshade (*Solanum sarrachoides*) control in potatoes (*Solanum tuberosum*) with bentazon plus additives. Weed Technology 6, 85–90.

(List continued on next page.)

*Primary Examiner*—S. Mark Clardy
(74) *Attorney, Agent, or Firm*—James C. Forbes

(57) ABSTRACT

Methods and compositions are disclosed wherein exogenous chemicals are applied to plants to generate a desired biological response. One embodiment of the present invention is a plant treatment composition that comprises (a) an exogenous chemical and (b) an alkylether surfactant or mixture of such surfactants having the formula

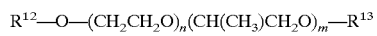

$$R^{12}-O-(CH_2CH_2O)_n(CH(CH_3)CH_2O)_m-R^{13}$$

wherein $R^{12}$ is an alkyl or alkenyl group having about 16 to about 22 carbon atoms, n is an average number of about 10 to about 100, m is an average number of 0 to about 5 and $R^{13}$ is hydrogen or $C_{1-4}$ alkyl. The alkylether surfactant or mixture thereof is present in an amount such that the weight/weight ratio of said alkylether surfactant or mixture of such surfactants to the exogenous chemical is about 1:3 to about 1:100.

75 Claims, No Drawings

FOREIGN PATENT DOCUMENTS

| | | | |
|---|---|---|---|
| 5-078204 | 3/1993 | (JP) . | |
| 5-085901 | 4/1993 | (JP) . | |
| 5-112414 | 5/1993 | (JP) . | |
| 5-148105 | 6/1993 | (JP) . | |
| 5-155706 | 6/1993 | (JP) . | |
| 6-234603 | 8/1994 | (JP) . | |
| 6-263576 | 9/1994 | (JP) . | |
| 7-187915 | 7/1995 | (JP) . | |
| 8-151308 | 6/1996 | (JP) . | |
| WO 90/07272 | 7/1990 | (WO) . | |
| 91/08666 | 6/1991 | (WO) | A01N/25/12 |
| WO 92/06596 | 10/1992 | (WO) . | |
| WO 93/00007 | 1/1993 | (WO) . | |
| WO 93/21768 | 11/1993 | (WO) . | |
| WO 94/09627 | 5/1994 | (WO) . | |
| WO 94/13140 | 6/1994 | (WO) . | |
| WO 94/19941 | 9/1994 | (WO) . | |
| WO 95/07614 | 3/1995 | (WO) . | |
| 95/16351 | 6/1995 | (WO) | A01N/25/30 |
| 95/12977 | 8/1995 | (WO) | A01N/37/46 |
| WO 95/28410 | 10/1995 | (WO) . | |
| WO 95/31898 | 11/1995 | (WO) . | |
| WO 95/34200 | 12/1995 | (WO) . | |
| WO 96/00010 | 1/1996 | (WO) . | |
| WO 96/01047 | 1/1996 | (WO) . | |
| 96/03871 | 2/1996 | (WO) | A01N/25/04 |
| WO 96/22020 | 7/1996 | (WO) . | |
| WO 96/28973 | 9/1996 | (WO) . | |
| WO 97/12515 | 4/1997 | (WO) . | |
| WO 97/12516 | 4/1997 | (WO) . | |
| WO 97/27743 | 8/1997 | (WO) . | |
| WO 97/41730 | 11/1997 | (WO) . | |
| 89/3661 | 1/1990 | (ZA) . | |

OTHER PUBLICATIONS

Florence & Whitehill (1980). Some features of breakdown in water–in–oil–in–water multiple emulsions. Journal of Colloid and Interface Science 79, 243–256.

Foy (1996). Adjuvants—current trends and technology. Pesticide Formulation Adjuvant Technology (Formulations Forum 1994), 323–352. Boca Raton: CRC Press.

Foy & Witt (1993). Effects of methylated crop oils and other selected adjuvants on the herbicidal efficacy and selectivity of imazethapyr in soybeans. Pesticide Science 38, 260–262.

Garr & Hanks (1996). Effects of adjuvants on velvetleaf control with chlorimuron and imazethapyr in soybeans. FRI Bulletin 193 (Proceedings, Fourth International Symposium on Adjuvants for Agrochemicals, 1995), 432–436.

Gauvrit et al. (1995). Influence of ester derivatives of oleic–sunflower seed oil on the foliar penetration of herbicides. Mededelingen Faculteit Landbouwwetenschappen Rijksuniversiteit Gent 60(2a), 183–189.

Hamilton (1993). Structure and general properties of mineral and vegetable oils used as spray adjuvants. Pesticide Science 37, 141–146.

Hickey (1987). Methyl esters of fatty acids as pesticide formulation and application aids. ASTM Special Technical Publication 968, 67–74.

Killick et al. (1996). Ethylated esterified seed oils—a second generation of herbicide adjuvants. FRI Bulletin 193 (Proceedings, Fourth International Symposium on Adjuvants for Agrochemicals, 1995), 78–83.

Knoche & Bukovac (1993). Interaction of surfactant and leaf surface in glyphosate absorption. Weed Science 41, 87–93.

Kwon & Penner (1996). The effect of piperonyl butoxide and adjuvants on sulfonylurea herbicide activity. Weed Technology 10, 127–133.

Mack et al. (1996). Effects of several adjuvant classes on two herbicides for weed control. FRI Bulletin 193 (Proceedings, Fourth International Symposium on Adjuvants for Agrochemicals, 1995), 448–453.

Manthey et al. (1989a). Herbicide–oil–water emulsions. Weed Technology 3, 13–19.

Manthey et al. (1989b). Esterified seed oils with herbicides. In Chow et al., ed.: Adjuvants and Agrochemicals, vol. 2, 139–148. Boca Raton: CRC Press.

Manthey et al. (1990). Small grain and grass weed response to BAS–514 with adjuvants. Weed Technology 4, 366–370.

Manthey et al. (1992). Foliar absorption and phytotoxicity of quizalofop with lipid compounds. Weed Science 40, 558–562.

McMullan (1992). Effect of adjuvant and acidifying agent on imazamethabenz efficacy. Canadian Journal of Plant Science 72, 1389–1392.

Nalewaja (1986). Seed oils with herbicides. Mededelingen Faculteit Landbouwwetenschappen Rijksuniversiteit Gent 51(2a), 301–310.

Nalewaja & Matysiak (1993). Optimizing adjuvants to overcome glyphosate antagonistic salts. Weed Technology 7, 337–342.

Nalewaja et al. (1990). Imazethapyr efficacy with adjuvants and environments. Weed Technology 4, 765–770.

Nandula et al. (1995). Effectiveness of adjuvants with nicosulfuron and primisulfuron for wirestem muhyl (*Muhlenbergia frondosa*) control in no–till corn (*Zea mays*). Weed Technology 9, 525–530.

Omotosho et al. (1989). Methotrexate transport from the internal phase of multiple w/o/w emulsions. Journal of Microencapsulation 6, 183–192.

Roberts (1992). Laboratory procedures applicable to the evaluation of spray adjuvants utilizing methylated seed oils. Abstracts, Third International Symposium on Adjuvants for Agrochemicals. No page number.

Santier & Chamel (1996). Penetration of triolein and methyl oleate through isolated plant cuticles and their effect on penetration of [$^{14}$C] quizalofop–ethyl and [$^{14}$C] fenoxaprop– ethyl. Weed Research 36, 167–174.

Schönherr (1993). Effects of monodisperse alcohol ethoxylates on mobility of 2,4–D in isolated plant cuticles. Pesticide Science 38, 155–164.

Skelton (1993). Pesticide microemulsion concentrate formulations utilizing fatty acid methyl esters as solvent alternatives. ASTM Special Technical Publication 1183, 114–120.

Skrzypezak & Nalewaja (1987). Influence of various fatty acid formulations on the uptake and translocation of sethoxydim and fluazifop–butyl. Roczniki Nauk Rolniczych, Ser. E 16(2), 143–150. Abstract only.

Stock et al. (1992). Surfactant–enhanced foliar uptake of some organic compounds: interactions with two model polyoxyethylene aliphatic alcohols. Pesticide Science 34, 233–242.

Tann et al. (1996). Effect of various carbon chain length methyl esters as agricultural tank mix adjuvants. FRI Bulletin 193 (Proceedings, Fourth International Symposium on Adjuvants for Agrochemicals, 1995), 72–77.

Thompson et al. (1996). Adjuvant effects on imazethapyr, 2,4–D and picloram absorption by leafy spurge (*Euphorbia esula*). Weed Science 44, 469–475.

Townson (1990). Influence of formulation and application variables in relation to the performance of glyphosate and imazapyr for control of *Imperata cylindrica* (L.) Raeuschel. Ph.D. Thesis, University of Bristol. 312 pp.

Urvoy & Gauvrit (1991). Seed oils as adjuvants: penetration of glycerol trioleate, methanol oleate and diclofop–methyl in maize leaves. Proceedings, Brighton Crop Protection Conference, vol. 1, 337–342.

Urvoy et al. (1992). Seed oils as additives: penetration of triolein, methyl oleate and diclofop–methyl in maize leaves. Weed Research 32, 375–383.

Van Toor et al. (1994). Relationships between the herbicidal activity and foliar uptake of surfactant–containing solutions of glyphosate applied to foliage of oats and field beans. Crop Protection 13, 260–270.

Wills et al. (1993). Evaluation of the effect of a paraffinic petroleum oil–based adjuvant and an organosilicone–modifield methylated vegetable oil–based adjuvant on the efficacy of imazethapyr herbicide as applied in conventional and ultra–low volumes. Pesticide Science 38, 280–282.

Young (1983). Glyphosate plus adjuvants. Proceedings, Northeastern Weed Science Society 37, 250–254.

Serre, I. et al. (1993). Seed oil derivatives as adjuvants: influence of methyl to octadecyl oleates on the penetration of herbicides through various plant cuticles. Mededelingen, Faculteit Landbouwwetenschappen Rijksuniversiteit Gent 58(3a), 795–802. CA Abstract 120:263749.

\* cited by examiner

COMPOSITION AND METHOD FOR TREATING PLANTS WITH EXOGENOUS CHEMICALS

This application claims the benefit of provisional application Ser. No. 60/029,317, filed Oct. 25, 1996; provisional application Ser. No. 60/034,887, filed Jan. 31, 1997; and provisional application Ser. No. 60/039,789, filed Mar. 4, 1997. Each of those applications is incorporated here by reference.

BACKGROUND OF THE INVENTION

This invention relates to formulations and methods for enhancing the efficacy of exogenous chemicals used in treating plants. An exogenous chemical, as defined herein, is any chemical substance, whether naturally or synthetically derived, which (a) has biological activity or is capable of releasing in a plant an ion, moiety or derivative which has biological activity, and (b) is applied to a plant with the intent or result that the chemical substance or its biologically active ion, moiety or derivative enter living cells or tissues of the plant and elicit a stimulatory, inhibitory, regulatory, therapeutic, toxic or lethal response in the plant itself or in a pathogen, parasite or feeding organism present in or on the plant. Examples of exogenous chemical substances include, but are not limited to, chemical pesticides (such as herbicides, algicides, fungicides, bactericides, viricides, insecticides, aphicides, miticides, nematicides, molluscicides, and the like), plant growth regulators, fertilizers and nutrients, gametocides, defoliants, desiccants, mixtures thereof, and the like.

Exogenous chemicals, including foliar-applied herbicides, have at times been formulated with surfactants, so that when water is added, the resulting sprayable composition is more easily and effectively retained on the foliage (e.g., the leaves or other photosynthesizing organs) of plants. Surfactants can also bring other benefits, including improved contact of spray droplets with a waxy leaf surface and, in some cases, improved penetration of the accompanying exogenous chemical into the interior of leaves. Through these and perhaps other effects, surfactants have long been known to increase the biological effectiveness of herbicide compositions, or other compositions of exogenous chemicals, when added to or included in such compositions. Thus, for example, the herbicide glyphosate (N-phosphonomethylglycine) has been formulated with surfactants such as polyoxyalkylene-type surfactants including, among other surfactants, polyoxyalkylene alkylamines. Commercial formulations of glyphosate herbicide marketed under the trademark ROUNDUP® have been formulated with a surfactant composition based on such a polyoxyalkylene alkylamine, in particular a polyethoxylated tallowamine, this surfactant composition being identified as MON 0818. Surfactants have generally been combined with glyphosate or other exogenous chemicals either in a commercial concentrate (herein referred to as a "coformulation"), or in a diluted mixture that is prepared from separate compositions, one comprising an exogenous chemical (e.g. glyphosate) and another comprising surfactant, prior to use in the field (i.e., a tank mix).

Various combinations of exogenous chemicals and surfactants or other adjuvants have been tested in the past. In some instances, the addition of a particular surfactant has not produced uniformly positive or negative changes in the effect of the exogenous chemical on the plant (e.g., a surfactant that may enhance the activity of a particular herbicide on certain weeds may interfere with, or antagonize, the herbicidal efficacy on another weed species).

Some surfactants tend to degrade fairly rapidly in aqueous solutions. As a result, surfactants that exhibit this property can only be used effectively in tank mixes (i.e., mixed with the other ingredients in solution or dispersion in the tank soon before spraying is to occur), rather than being coformulated in an aqueous composition with the other ingredients in the first instance. This lack of stability, or inadequate shelf-life, has hindered the use of certain surfactants in some exogenous chemical formulations.

Other surfactants, though chemically stable, are physically incompatible with certain exogenous chemicals, particularly in concentrate coformulations. For example, most classes of nonionic surfactant, including polyoxyethylene alkylether surfactants, do not tolerate solutions of high ionic strength, as for example in a concentrated aqueous solution of a salt of glyphosate. Physical incompatibility can also lead to inadequate shelf-life. Other problems that can arise from such incompatibility include the formation of aggregates large enough to interfere with commercial handling and application, for example by blocking spray nozzles.

Another problem that has been observed in the past is the effect of environmental conditions on uptake of an exogenous chemical composition into foliage of a plant. For example, conditions such as temperature, relative humidity, presence or absence of sunlight, and health of the plant to be treated, can affect the uptake of a herbicide into the plant. As a result, spraying exactly the same herbicidal composition in two different situations can result in different herbicidal control of the sprayed plants.

One consequence of the above-described variability is that often a higher rate of herbicide per unit area is applied than might actually be required in that situation, in order to be certain that adequate control of undesired plants will be achieved. For similar reasons, other foliar-applied exogenous chemicals are also typically applied at significantly higher rates than needed to give the desired biological effect in the particular situation where they are used, to allow for the natural variability that exists in efficiency of foliar uptake. A need therefore exists for compositions of exogenous chemicals that, through more efficient uptake into plant foliage, allow reduced use rates.

Many exogenous chemicals are commercially packaged as a liquid concentrate that contains a significant amount of water. The packaged concentrate is shipped to distributors or retailers. Ultimately the packaged concentrate ends up in the hands of an end user, who further dilutes the concentrate by adding water in accordance with label instructions on the package. The dilute composition thus prepared is then sprayed on plants.

A significant portion of the cost of such packaged concentrates is the cost of transporting the concentrate from the manufacturing site to the location where the end user purchases it. Any liquid concentrate formulation that contained relatively less water and thus more exogenous chemical would reduce the cost per unit amount of exogenous chemical. However, one important limit on the ability of the manufacturer to increase the loading of the exogenous chemical in the concentrate is the stability of that formulation. With some combinations of ingredients, a limit will be reached at which any further reduction of water content in the concentrate will cause it to become unstable (e.g., to separate into discrete layers), which may make it commercially unacceptable.

Accordingly, a need exists for improved formulations of exogenous chemicals, particularly herbicides, that are stable, effective, less sensitive to environmental conditions, and permit the use of reduced amounts of exogenous chemical to achieve the desired biological effect in or on plants. A need also exists for stable liquid concentrate formulations of exogenous chemicals that contain less water and more exogenous chemical than prior art concentrates.

SUMMARY OF THE INVENTION

The present invention relates to novel methods and compositions wherein exogenous chemicals are applied to plants to generate a desired biological response.

One embodiment of the present invention is a plant treatment composition that comprises (a) an exogenous chemical and (b) an alkylether surfactant or mixture of such surfactants having the formula $$R^{12}\text{—}O\text{—}(CH_2CH_2O)_n(CH(CH_3)CH_2O)_m\text{—}R^{13} \qquad VI$$

wherein $R^{12}$ is an alkyl or alkenyl group having about 16 to about 22 carbon atoms, n is an average number of about 10 to about 100, m is an average number of 0 to about 5 and $R^{13}$ is hydrogen or $C_{1-4}$ alkyl. The alkylether surfactant or mixture thereof is present in an amount such that the weight/weight ratio of said alkylether surfactant or mixture of such surfactants to the exogenous chemical is about 1:3 to about 1:100. The term "alkylether" as used herein should be understood to include alkenylether surfactants. Preferably $R^{12}$ is a saturated straight-chain alkyl group, $R^{13}$ is hydrogen, m is 0 and n is from about 10 to about 40, more preferably from about 20 to about 40. Most preferably the alkylether surfactant is a polyoxyethylene cetyl or stearyl ether or mixture thereof having 20–40 moles of ethylene oxide (EO).

In one embodiment, the composition is an aqueous concentrate further comprising water and an amount of a solid inorganic particulate colloidal material effective to stabilize the composition, said composition not exhibiting phase separation over a period of time T as defined below when stored in a closed container at a temperature in the range from about 15° C. to about 30° C.; wherein the exogenous chemical and the surfactant are present at concentrations in the absolute or relative to each other such that, in the absence of the colloidal material, phase separation would occur during said period of time T.

The period of time T over which a composition can be observed to determine if phase separation occurs is in the range from about 1 hour to about 60 days. "Phase separation" in the present context means separation of at least part of the surfactant component from other ingredients of the composition as a distinct phase. The particulate colloidal material preferably is present in an amount between about 0.01% and about 5% by weight, more preferably between about 0.5% and about 2.5% by weight, of the composition. By "aqueous concentrate" is meant a composition comprising water and from about 10% to about 60% by weight of the exogenous chemical.

Examples of suitable solid particulate colloidal materials include inorganic oxides such as silicon oxides, aluminum oxides, titanium oxides, and mixtures thereof. Preferably the particulate colloidal material has an average specific surface area of about 50 to about 400 m²/g, more preferably about 180 to about 400 m²/g. In one particular embodiment, the particulate colloidal material has a bimodal distribution of specific surface area whereby a first component of the colloidal material has an average specific surface area of about 50 to about 150 m²/g and a second component of the colloidal material has an average specific surface area of about 180 to about 400 m²/g.

In another embodiment of the invention, compositions are provided comprising (a) an exogenous chemical, (b) an alkylether surfactant or mixture of such surfactants having the formula shown above, and (c) a compound of formula $$R^{14}\text{—}CO\text{—}A\text{—}R^{15} \qquad VII$$

wherein $R^{14}$ is a hydrocarbyl group having about 5 to about 21 carbon atoms, $R^{15}$ is a hydrocarbyl group having 1 to about 14 carbon atoms, the total number of carbon atoms in $R^{14}$ and $R^{15}$ is about 11 to about 27, and A is O or NH. $R^{14}$ preferably has about 11 to about 21 carbon atoms, $R^{15}$ preferably has 1 to about 6 carbon atoms and A is preferably O. The aqueous composition in embodiments comprising a compound of formula VII preferably is an emulsion comprising an oil phase that comprises said second excipient substance, for example a water-in-oil-in-water multiple emulsion or an oil-in-water emulsion.

A composition comprising a compound of formula VII can, if desired or necessary, further comprise an amount of solid inorganic particulate colloidal material effective to stabilize the composition, exactly as defined above.

In certain preferred embodiments of the present invention, the compound (c) is a $C_{1-4}$ alkyl ester of a $C_{12-18}$ fatty acid, more preferably a $C_{1-4}$ alkyl ester of a $C_{12-18}$ saturated fatty acid. Propyl, isopropyl or butyl esters of $C_{12-18}$ fatty acids, such as butyl stearate, are especially preferred.

A wide variety of exogenous chemicals can be used in the compositions and methods of the present invention. A preferred class is foliar-applied exogenous chemicals, i.e. exogenous chemicals that are normally applied post-emergence to foliage of plants. A preferred subclass of foliar-applied exogenous chemicals is those that are water-soluble. By "water-soluble" in this context is meant having a solubility in distilled water at 25° C. greater than about 1% by weight. Especially preferred water-soluble exogenous chemicals are salts that have an anion portion and a cation portion. In one embodiment of the invention, at least one of the anion and cation portions is biologically active and has a molecular weight of less than about 300. Particular examples of such exogenous chemicals where the cation portion is biologically active are paraquat, diquat and chlormequat. More commonly it is the anion portion that is biologically active.

Another preferred subclass of exogenous chemicals is those that exhibit systemic biological activity in the plant. Within this subclass, an especially preferred group of exogenous chemicals is N-phosphonomethylglycine and its herbicidal derivatives. N-phosphonomethylglycine, often referred to by its common name glyphosate, can be used in its acid form, but is more preferably used in the form of a salt. Any water-soluble salt of glyphosate can be used in the practice of this invention. Some preferred salts include the sodium, potassium, ammonium, mono-, di-, tri- and tetra-$C_{1-4}$-alkylammonium, mono-, di- and tri-$C_{1-4}$-alkanolammonium, mono-, di- and tri-$C_{1-4}$-alkylsulfonium and sulfoxonium salts. The ammonium, monoisopropylammonium and trimethylsulfonium salts of glyphosate are especially preferred. Mixtures of salts can also be useful in certain situations.

Compositions of the present invention can be used in methods of treating plants. Foliage of a plant is contacted with a biologically effective amount of the composition. "Contacting" in this context means placing the composition on the foliage.

A composition of the present invention comprising an exogenous chemical and an alkylether surfactant as described above can have a number of different physical forms. For example, the composition can further comprise water in an amount effective to make the composition a dilute aqueous composition ready for application to foliage of a plant. Such a composition typically contains about 0.02 to about 2 percent by weight of the exogenous chemical, but for some purposes can contain up to about 10 percent by weight or even more of the exogenous chemical.

Alternatively, the composition can be a shelf-stable concentrate composition comprising the exogenous chemical substance in an amount of about 10 to about 90 percent by weight. Such shelf-stable concentrates can be, for example, (1) a solid composition comprising the exogenous chemical substance in an amount of about 30 to about 90 percent by weight, such as a water-soluble or water-dispersible granular formulation, or (2) a composition that further comprises a liquid diluent, wherein the composition comprises the exogenous chemical substance in an amount of about 10 to about 60 percent by weight. In this latter embodiment, it is especially preferred for the exogenous chemical substance to be water-soluble and present in an aqueous phase of the composition in an amount of about 15 to about 45 percent by weight of the composition. In particular, such a composition can be, for example, an aqueous solution concentrate or an emulsion having an oil phase. If it is an emulsion, it can more specifically be, for example, an oil-in-water emulsion, a water-in-oil emulsion, or a water-in-oil-in-water multiple emulsion. When a compound (c) such as butyl stearate is included in an emulsion composition, it is predominantly present in the oil phase.

As described above, one embodiment of the invention is a sprayable composition that comprises an exogenous chemical, an aqueous diluent, and an alkylether surfactant. The term "spray composition" is sometimes used herein to mean a sprayable composition.

In a related embodiment of the invention, a concentrate composition is provided which, upon dilution, dispersion or dissolution in water forms the sprayable composition just described. The concentrate composition contains a reduced amount of the aqueous diluent, or, in a particular embodiment, is a dry composition having less than about 5% water by weight. Typically a concentrate composition of the invention contains at least about 10% by weight of the exogenous chemical, preferably at least about 15%.

The compositions and methods of the present invention have a number of advantages. They provide enhanced biological activity of exogenous chemicals in or on plants in comparison with prior formulations, either in terms of greater ultimate biological effect, or obtaining an equivalent biological effect while using a reduced application rate of exogenous chemical. Certain herbicide formulations of the present invention can avoid antagonism that has been observed in some prior art herbicide formulations, and can minimize quick production of necrotic lesions on leaves that in some situations hinder overall translocation of herbicide in the plant. Certain herbicide compositions of the invention modify the spectrum of activity of the herbicide across a range of plant species. For example, certain formulations of the present invention containing glyphosate can provide good herbicidal activity against broadleaf weeds while not losing any herbicidal effectiveness on narrowleaf weeds. Others can enhance herbicidal effectiveness on narrowleaf weeds to a greater extent than on broadleaf weeds. Still others can have enhanced effectiveness which is specific to a narrow range of species or even a single species.

Another advantage of the present invention is that it employs relatively small amounts of the alkylether surfactant in relation to the amount of exogenous chemical employed. This makes the compositions and methods of the present invention relatively inexpensive, and also tends to reduce instability problems in specific compositions where the alkylether surfactant is physically incompatible with the exogenous chemical (e.g., in solutions of high ionic strength, such as concentrated glyphosate salt solutions).

Even at the low concentrations of the excipient substances used in the present invention, there may be limits on the maximum concentration of exogenous chemical that can be used without causing compatibility problems (e.g., separation of the composition into discrete layers). In some preferred embodiments of the invention, composition stability at high loadings of exogenous chemical is maintained by adding other ingredients such as, for example, colloidal particulates. Some compositions of the present invention exhibit enhanced biological activity and have a higher loading of exogenous chemical than possible in prior art compositions.

Further, compositions of the present invention are less sensitive in some instances to environmental conditions such as relative humidity at the time of application to the plant. Also, the present invention allows the use of smaller amounts of herbicides or other pesticides, while still obtaining the required degree of control of weeds or other undesired organisms.

DESCRIPTION OF ILLUSTRATIVE EMBODIMENTS

Examples of exogenous chemical substances that can be included in compositions of the present invention include, but are not limited to, chemical pesticides (such as herbicides, algicides, fungicides, bactericides, viricides, insecticides, aphicides, miticides, nematicides, molluscicides and the like), plant growth regulators, fertilizers and nutrients, gametocides, defoliants, desiccants, mixtures thereof and the like. In one embodiment of the invention, the exogenous chemical is polar.

A preferred group of exogenous chemicals are those that are normally applied post-emergence to the foliage of plants, i.e. foliar-applied exogenous chemicals.

Some exogenous chemicals useful in the present invention are water-soluble, for example salts that comprise biologically active ions, and also comprise counterions, which may be biologically inert or relatively inactive. A particularly preferred group of these water-soluble exogenous chemicals or their biologically active ions or moieties are systemic in plants, that is, they are to some extent translocated from the point of entry in the foliage to other parts of the plant where they can exert their desired biological effect. Especially preferred among these are herbicides, plant growth regulators and nematicides, particularly those that have a molecular weight, excluding counterions, of less than about 300. More especially preferred among these are exogenous chemical compounds having one or more functional groups selected from amine, carboxylate, phosphonate and phosphinate groups.

Among such compounds, an even more preferred group are herbicidal or plant growth regulating exogenous chemical compounds having at least one of each of amine, carboxylate, and either phosphonate or phosphinate functional groups. Salts of N-phosphonomethylglycine are examples of this group of exogenous chemicals. Further examples include salts of glufosinate, for instance the ammonium salt (ammonium DL-homoalanin-4-yl(methyl) phosphinate).

Another preferred group of exogenous chemicals which can be applied by the method of the invention are nematicides such as those disclosed in U.S. Pat. No. 5,389,680, the disclosure of which is incorporated herein by reference. Preferred nematicides of this group are salts of 3,4,4-trifluoro-3-butenoic acid or of N-(3,4,4-trifluoro-1-oxo-3-butenyl)glycine.

Exogenous chemicals which can usefully be applied by the method of the present invention are normally, but not exclusively, those which are expected to have a beneficial effect on the overall growth or yield of desired plants such as crops, or a deleterious or lethal effect on the growth of undesirable plants such as weeds. The method of the present invention is particularly useful for herbicides, especially those that are normally applied post-emergence to the foliage of unwanted vegetation.

Herbicides which can be applied by the method of the present invention include but are not limited to any listed in standard reference works such as the "Herbicide Handbook," *Weed Science Society of America*, 1994, 7th Edition, or the "Farm Chemicals Handbook," Meister Publishing Company, 1997 Edition. Illustratively these herbicides include acetanilides such as acetochlor, alachlor and metolachlor, aminotriazole, asulam, bentazon, bialaphos, bipyridyls such as paraquat, bromacil, cyclohexenones such as clethodim and sethoxydim, dicamba, diflufenican, dinitroanilines such as pendimethalin, diphenylethers such as acifluorfen, fomesafen and oxyfluorfen, fatty acids such as $C_{9-10}$ fatty acids, fosamine, flupoxam, glufosinate, glyphosate, hydroxybenzonitriles such as bromoxynil, imidazolinones such as imazaquin and imazethapyr, isoxaben, norflurazon, phenoxies such as 2,4-D, phenoxypropionates such as diclofop, fluazifop and quizalofop, picloram, propanil, substituted ureas such as fluometuron and isoproturon, sulfonylureas such as chlorimuron, chlorsulfuron, halosulfuron, metsulfuron, primisulfuron, sulfometuron and sulfosulfuron, thiocarbamates such as triallate, triazines such as atrazine and metribuzin, and triclopyr. Herbicidally active derivatives of any known herbicide are also within the scope of the present invention. A herbicidally active derivative is any compound which is a minor structural modification, most commonly but not restrictively a salt or ester, of a known herbicide. These compounds retain the essential activity of the parent herbicide, but may not necessarily have a potency equal to that of the parent herbicide. These compounds may convert to the parent herbicide before or after they enter the treated plant. Mixtures or coformulations of a herbicide with other ingredients, or of more than one herbicide, may likewise be employed.

An especially preferred herbicide is N-phosphonomethylglycine (glyphosate), a salt, adduct or ester thereof, or a compound which is converted to glyphosate in plant tissues or which otherwise provides glyphosate ion. Glyphosate salts that can be used according to this invention include but are not restricted to alkali metal, for example sodium and potassium, salts; ammonium salt; alkylamine, for example dimethylamine and isopropylamine, salts; alkanolamine, for example ethanolamine, salts; alkylsulfonium, for example trimethylsulfonium, salts; sulfoxonium salts; and mixtures thereof. The herbicidal compositions sold by Monsanto Company as ROUNDUP® and ACCORD® contain the monoisopropylamine (IPA) salt of N-phosphonomethylglycine. The herbicidal compositions sold by Monsanto Company as ROUNDUP® Dry and RIVAL® contain the monoammonium salt of N-phosphonomethylglycine. The herbicidal composition sold by Monsanto Company as ROUNDUP® Geoforce contains the monosodium salt of N-phosphonomethylglycine. The herbicidal composition sold by Zeneca as TOUCHDOWN® contains the trimethylsulfonium salt of N-phosphonomethylglycine. The herbicidal properties of N-phosphonomethylglycine and its derivatives were first discovered by Franz, then disclosed and patented in U.S. Pat. No. 3,799,758, issued Mar. 26, 1974. A number of herbicidal salts of N-phosphonomethylglycine were patented by Franz in U.S. Pat. No. 4,405,531, issued Sep. 20, 1983. The disclosures of both of these patents are hereby incorporated by reference.

Because the commercially most important herbicidal derivatives of N-phosphonomethylglycine are certain salts thereof, the glyphosate compositions useful in the present invention will be described in more detail with respect to such salts. These salts are well known and include ammonium, IPA, alkali metal (such as the mono-, di-, and trisodium salts, and the mono-, di-, and tripotassium salts), and trimethylsulfonium salts. Salts of N-phosphonomethylglycine are commercially significant in part because they are water soluble. The salts listed immediately above are highly water soluble, thereby allowing for highly concentrated solutions that can be diluted at the site of use. In accordance with the method of this invention as it pertains to glyphosate herbicide, an aqueous solution containing a herbicidally effective amount of glyphosate and other components in accordance with the invention is applied to foliage of plants. Such an aqueous solution can be obtained by dilution of a concentrated glyphosate salt solution with water, or dissolution or dispersion in water of a dry (e.g. granular, powder, tablet or briquette) glyphosate formulation.

Exogenous chemicals should be applied to plants at a rate sufficient to give the desired biological effect. These application rates are usually expressed as amount of exogenous chemical per unit area treated, e.g. grams per hectare (g/ha). What constitutes a "desired effect" varies according to the standards and practice of those who investigate, develop, market and use a specific class of exogenous chemicals. For example, in the case of a herbicide, the amount applied per unit area to give 85% control of a plant species as measured by growth reduction or mortality is often used to define a commercially effective rate.

Herbicidal effectiveness is one of the biological effects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The herbicidal effectiveness data set forth herein report "inhibition" as a percentage following a standard procedure in the art which reflects a visual assessment of plant mortality and growth reduction by comparison with untreated plants, made by technicians specially trained to make and record such observations. In all cases, a single technician makes all assessments of percent inhibition within any one experiment or trial. Such measurements are relied upon and regularly reported by Monsanto Company in the course of its herbicide business.

The selection of application rates that are biologically effective for a specific exogenous chemical is within the skill of the ordinary agricultural scientist. Those of skill in the art will likewise recognize that individual plant conditions, weather and growing conditions, as well as the specific exogenous chemical and formulation thereof selected, will affect the efficacy achieved in practicing this invention. Useful application rates for exogenous chemicals employed can depend upon all of the above conditions. With respect to the use of the method of this invention for glyphosate herbicide, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate or derivatives thereof are used to control a very wide variety of plants worldwide. Such compositions can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium, and Zea.

Particularly important species for which glyphosate compositions are used are exemplified without limitation by the following:

Annual Broadleaves:
  velvetleaf (*Abutilon theophrasti*)
  pigweed (Amaranthus spp.)
  buttonweed (Borreria spp.)
  oilseed rape, canola, indian mustard, etc. (Brassica spp.)
  commelina (Commelina spp.)
  filaree (Erodium spp.)
  sunflower (Helianthus spp.)
  morningglory (Ipomoea spp.)
  kochia (*Kochia scoparia*)
  mallow (Malva spp.)
  wild buckwheat, smartweed, etc. (Polygonum spp.)
  purslane (Portulaca spp.)
  russian thistle (Salsola spp.)
  sida (Sida spp.)
  wild mustard (*Sinapis arvensis*)
  cocklebur (Xanthium spp.)
Annual Narrowleaves:
  wild oat (*Avena fatua*)
  carpetgrass (Axonopus spp.)
  downy brome (*Bromus tectorum*)
  crabgrass (Digitaria spp.)
  barnyardgrass (*Echinochloa crus-galli*)
  goosegrass (*Eleusine indica*)
  annual ryegrass (*Lolium multiflorum*)
  rice (*Oryza sativa*)
  ottochloa (*Ottochloa nodosa*)
  bahiagrass (*Paspalum notatum*)
  canarygrass (Phalaris spp.)
  foxtail (Setaria spp.)
  wheat (*Triticum aestivum*)
  corn (*Zea mays*)
Perennial Broadleaves:
  mugwort (Artemisia spp.)
  milkweed (Asclepias spp.)
  canada thistle (*Cirsium arvense*)
  field bindweed (*Convolvulus arvensis*)
  kudzu (Pueraria spp.)
Perennial Narrowleaves:
  brachiaria (Brachiaria spp.)
  bermudagrass (*Cynodon dactylon*)
  yellow nutsedge (*Cyperus esculentus*)
  purple nutsedge (*C. rotundus*)
  quackgrass (*Elymus repens*)
  lalang (*Imperata cylindrica*)

perennial ryegrass (*Lolium perenne*)
guineagrass (*Panicum maximum*)
dallisgrass (*Paspalum dilatatum*)
reed (Phragmites spp.)
johnsongrass (*Sorghum halepense*)
cattail (Typha spp.)
Other Perennials:
horsetail (Equisetum spp.)
bracken (*Pteridium aquilinum*)
blackberry (Rubus spp.)
gorse (*Ulex europaeus*)

Thus, the method of the present invention, as it pertains to glyphosate herbicide, can be useful on any of the above species.

Effectiveness in greenhouse tests, usually at exogenous chemical rates lower than those normally effective in the field, is a proven indicator of consistency of field performance at normal use rates. However, even the most promising composition sometimes fails to exhibit enhanced performance in individual greenhouse tests. As illustrated in the Examples herein, a pattern of enhancement emerges over a series of greenhouse tests; when such a pattern is identified this is strong evidence of biological enhancement that will be useful in the field.

Compositions of the present invention include one or more long-chain alkylether surfactants having the formula VI above. $R^{12}$ can be branched or unbranched, saturated or unsaturated. $R^{12}$ is preferably straight chain saturated $C_{16}$ alkyl (cetyl) or straight chain saturated $C_{18}$ alkyl (stearyl). In preferred alkylethers m is 0, n is an average number from about 20 to about 40 and $R^{13}$ is preferably hydrogen. Among especially preferred alkylether surfactants are those identified in the International Cosmetic Ingredient Directory as ceteth-20, ceteareth-20, ceteareth-27, steareth-20 and steareth-30.

Aqueous concentrate compositions in some circumstances are limited in the degree to which an exogenous chemical such as glyphosate can be loaded. At some point, as the loading of exogenous chemical is increased, the composition will not remain suitably stable. Addition of a small amount of colloidal particulate to such compositions has surprisingly been found to greatly increase loading ability while retaining desired stability. Inclusion of such colloidal particulates can also enhance biological activity of an exogenous chemical formulation. Oxides of silicon, aluminum and titanium are preferred colloidal particulate materials. Particle size is preferably such that specific surface area is in the range from about 50 to about 400 $m^2/g$. Where the exogenous chemical is glyphosate, the use of colloidal particulate enables glyphosate acid equivalent loadings of at least 30% by weight for compositions containing sufficient alkylether and fatty acid ester to show enhanced herbicidal effectiveness, or at least 40% by weight for compositions containing alkylether but no fatty acid ester, and showing herbicidal effectiveness at least equal to current commercial products loaded at about 30% by weight. We have found especially useful improvement in storage stability can be obtained using colloidal particulates having specific surface area between about 180 and about 400 $m^2/g$.

Other means of improving stability of highly loaded compositions may also be possible and are within the scope of the present invention.

Compositions in accordance with the present invention are typically prepared by combining water, the exogenous chemical, the alkylether surfactant, and other ingredients such as colloidal particulates and/or fatty acid esters if such ingredients are to be used. Details of specific processes used to prepare such compositions are included in the Examples herein.

The concentrations of the various components will vary, in part depending on whether a concentrate is being prepared that will be further diluted before spraying onto a plant, or whether a solution or dispersion is being prepared that can be sprayed without further dilution.

In an aqueous glyphosate formulation that includes a $C_{16-18}$ alkylether surfactant and butyl stearate, suitable concentrations can be: glyphosate 0.1–400 g a.e./l, alkylether surfactant 0.001–10% by weight, and butyl stearate 0.001–10% by weight. To achieve the higher concentrations in these ranges, it is often beneficial to add other ingredients to provide acceptable storage stability, for example colloidal particulate silica or aluminum oxide at 0.5–2.5% by weight. In an aqueous glyphosate formulation that includes a $C_{16-18}$ alkylether surfactant but no butyl stearate, glyphosate concentration can suitably be increased to 500 g a.e./l or more, in the presence of a colloidal particulate at 0.5–2.5% by weight.

In solid glyphosate formulations, higher concentrations of ingredients are possible because of the elimination of most of the water.

Although various compositions of the present invention are described herein as comprising certain listed materials, in some preferred embodiments of the invention the compositions consist essentially of the indicated materials.

Optionally, other agriculturally acceptable materials can be included in the compositions. For example, more than one exogenous chemical can be included. Also, various agriculturally acceptable adjuvants can be included, whether or not their purpose is to directly contribute to the effect of the exogenous chemical on a plant. For example, when the exogenous chemical is a herbicide, liquid nitrogen fertilizer or ammonium sulfate might be included in the composition. As another example, stabilizers can be added to the composition. In some instances it might be desirable to include microencapsulated acid in the composition, to lower the pH of a spray solution on contact with a leaf. One or more surfactants can also be included. Surfactants mentioned here by trade name, and other surfactants that can be useful in the method of the invention, are indexed in standard reference works such as McCutcheon's Emulsifiers and Detergents, 1997 edition, Handbook of Industrial Surfactants, 2nd Edition, 1997, published by Gower, and International Cosmetic Ingredient Dictionary, 6th Edition, 1995.

The compositions of the present invention can be applied to plants by spraying, using any conventional means for spraying liquids, such as spray nozzles, atomizers, or the like. Compositions of the present invention can be used in precision farming techniques, in which apparatus is employed to vary the amount of exogenous chemical applied to different parts of a field, depending on variables such as the particular plant species present, soil composition, and the like. In one embodiment of such techniques, a global positioning system operated with the spraying apparatus can be used to apply the desired amount of the composition to different parts of a field.

The composition at the time of application to plants is preferably dilute enough to be readily sprayed using standard agricultural spray equipment. Preferred application rates for the present invention vary depending upon a number of factors, including the type and concentration of active ingredient and the plant species involved. Useful rates for applying an aqueous composition to a field of foliage can range from about 25 to about 1,000 liters per hectare (l/ha) by spray application. The preferred application rates for aqueous solutions are in the range from about 50 to about 300 l/ha.

Many exogenous chemicals (including glyphosate herbicide) must be taken up by living tissues of the plant and translocated within the plant in order to produce the desired biological (e.g., herbicidal) effect. Thus, it is important that a herbicidal composition not be applied in such a manner as to excessively injure and interrupt the normal functioning of the local tissue of the plant so quickly that translocation is reduced. However, some limited degree of local injury can be insignificant, or even beneficial, in its impact on the biological effectiveness of certain exogenous chemicals.

A large number of compositions of the invention are illustrated in the Examples that follow. Many concentrate compositions of glyphosate have provided sufficient herbicidal effectiveness in greenhouse tests to warrant field testing on a wide variety of weed species under a variety of application conditions. Aqueous compositions tested in the field comprising an alkylether surfactant and/or containing a fatty acid ester have included:

| Field composition | Glyphosate g a.e./l | Fatty acid ester | Surfactant | Type of surfactant | Type of fatty acid ester |
|---|---|---|---|---|---|
| F-5 | 163 | 1.0 | 10.0 | oleth-20 | Bu stearate |
| F-8 | 163 | 1.0 | 10.0 | steareth-20 | Bu stearate |
| F-11 | 163 | 0.5 | 5.0 | oleth-20 | Bu stearate |
| F-12 | 163 | 0.3 | 5.0 | oleth-20 | Bu stearate |
| F-13 | 163 | 0.3 | 2.5 | oleth-20 | Bu stearate |
| F-16 | 163 | 0.5 | 5.0 | steareth-20 | Bu stearate |
| F-17 | 163 | 0.5 | 5.0 | ceteth-20 | Bu stearate |
| F-19 | 163 | 0.5 | 5.0 | ceteareth-27 | Bu stearate |
| F-22 | 163 | | 5.0 | steareth-20 | |
| F-23 | 163 | | 5.0 | ceteth-20 | |
| F-24 | 163 | | 5.0 | laureth-23 | |
| F-25 | 163 | 0.3 | 5.0 | ceteareth-27 | Bu stearate |
| F-26 | 163 | 0.3 | 2.5 | ceteareth-27 | Bu stearate |
| F-27 | 163 | | 5.0 | ceteareth-27 | |
| F-28 | 163 | 0.5 | 5.0 | ceteareth-27 | Me stearate |
| F-29 | 163 | 0.5 | 5.0 | steareth-20 | Me stearate |
| F-30 | 163 | 0.5 | 5.0 | oleth-20 | |
| F-33 | 163 | 0.5 | 5.0 | ceteareth-15 | Bu stearate |
| F-34 | 163 | | 5.0 | ceteareth-15 | |
| F-35 | 163 | 0.5 | 5.0 | steareth-30 | Bu stearate |

The above compositions were prepared by process (vii) if they contain fatty acid ester and by process (viii) if they do not. Both processes are described in the Examples.

Aqueous compositions tested in the field containing colloidal particulates have included:

| Field composition | Glyphosate g a.e./l | Fatty acid ester | Surfactant | Coll. partic. | Other surfactant | Type of colloidal particulate | Type of fatty acid ester | Other ingredients |
|---|---|---|---|---|---|---|---|---|
| F-36 | 360 | 1.0 | 10.0 | 1.3 | steareth-20 | Aerosil 380 | Bu stearate | |
| F-37 | 360 | 1.0 | 10.0 | 1.3 | oleth-20 | Aerosil 380 | Bu stearate | |
| F-38 | 360 | 1.0 | 10.0 | 1.3 | steareth-30 | Aerosil 380 | Bu stearate | |
| F-39 | 360 | | 10.0 | 1.3 | steareth-30 | Aerosil 380 | | |
| F-50 | 360 | 1.0 | 10.0 | 1.3 | ceteareth-15 | Aerosil 380 | Bu stearate | |
| F-51 | 360 | 1.0 | 10.0 | 1.3 | ceteth-20 | Aerosil 380 | Bu stearate | |
| F-52 | 360 | 1.0 | 10.0 | 1.3 | steareth-20 | Aerosil 380 | Bu stearate | |
| F-53 | 360 | 1.0 | 10.0 | 1.3 | oleth-20 | Aerosil 380 | Bu stearate | |
| F-54 | 360 | 1.0 | 10.0 | 1.3 | ceteareth-27 | Aerosil 380 | Bu stearate | |
| F-55 | 360 | 1.0 | 10.0 | 1.3 | steareth-30 | Aerosil 380 | Bu stearate | |
| F-56 | 360 | | 10.0 | 1.3 | steareth-30 | Aerosil 380 | | |
| F-57 | 360 | | 10.0 | 1.3 | ceteareth-27 | Aerosil 380 | | |
| F-58 | 360 | | 10.0 | 1.3 | steareth-20 | Aerosil 380 | | |
| F-59 | 360 | | 10.0 | 1.3 | oleth-20 | Aerosil 380 | | |
| F-60 | 360 | 1.0 | 10.0 | 1.3 | ceteareth-27 | Aerosil 380 | Me stearate | |
| F-61 | 360 | 1.0 | 10.0 | 1.3 | ceteareth-27 | Aerosil 380 | Me palmitate | |
| F-62 | 300 | | 10.0 | 1.3 | ceteareth-27 | Aerosil 380 | | |
| F-63 | 240 | | 10.0 | 1.3 | ceteareth-27 | Aerosil 380 | | |
| F-64 | 360 | | 6.0 | 1.3 | ceteareth-27 | Aerosil 380 | | |
| F-65 | 300 | | 6.0 | 1.3 | ceteareth-27 | Aerosil 380 | | |
| F-66 | 240 | | 6.0 | 1.3 | ceteareth-27 | Aerosil 380 | | |
| F-84 | 480 | | 3.0 | 0.8 | steareth-20 | Aerosil 380 | | |
| F-85 | 480 | | 3.0 | 1.5 | oleth-20 | Aerosil 380 | | |
| F-86 | 480 | | 3.0 | 1.5 | oleth-20 | Aerosil MOX-170 | | |
| F-87 | 480 | | 3.0 | 1.5 | oleth-20 | Aerosil OX-50 | | |

-continued

| Field composition | Gly-phosate g a.e./l | Fatty acid ester | Surfactant | Coll. partic. | Other | Type of surfactant | Type of colloidal particulate | Type of fatty acid ester | Other ingredients |
|---|---|---|---|---|---|---|---|---|---|
| F-89 | 480 | | 3.0 | 1.5 | | steareth-20 | Aerosil blend 2 | | |
| F-90 | 480 | | 3.0 | 1.5 | | oleth-20 | Aerosil blend 2 | | |
| F-91 | 480 | | 4.5 | 1.5 | | oleth-20 | Aerosil 380 | | |
| F-92 | 480 | | 4.5 | 1.5 | | steareth-20 | Aerosil 380 | | |
| F-93 | 480 | | 3.0 | 1.5 | | steareth-20 | Aerosil blend 1 | | |
| F-94 | 480 | | 1.0 | 1.5 | | steareth-20 | Aerosil blend 1 | | |
| F-95 | 480 | | 6.0 | 1.5 | | steareth-20 | Aerosil blend 1 | | |
| F-96 | 480 | | 4.5 | 1.5 | 0.5 | steareth-20 | Aerosil blend 2 | | propylene glycol |
| F-97 | 480 | | 6.0 | 1.5 | 0.5 | steareth-20 | Aerosil blend 2 | | propylene glycol |
| F-98 | 480 | | 6.0 | 1.5 | 0.5 | oleth-20 | Aerosil blend 2 | | propylene glycol |
| F-99 | 480 | | 4.5 + 2.3 | 1.5 | 0.5 | steareth-20 + Ethomeen T/25 | Aerosil blend 2 | | propylene glycol |
| F-100 | 480 | | 6.0 | 1.5 | | steareth-20 | Al oxide C | | |
| F-101 | 480 | | 4.5 + 2.3 | 1.5 | 0.5 | steareth-20 + Ethomeen T/25 | Al oxide C | | propylene glycol |
| F-102 | 480 | | 4.5 + 1.0 | 1.5 | 0.5 | steareth-20 + Ethomeen T/25 | Al oxide C | | propylene glycol |
| F-103 | 480 | | 3.0 | 1.5 | | steareth-20 | Aerosil 380 | | |
| F-104 | 480 | | 4.5 | 1.5 | | steareth-20 | Al oxide C | | |
| F-105 | 480 | | 6.0 | 1.5 | | steareth-20 | Aerosil 380 | | |
| F-106 | 480 | | 4.5 + 1.0 | 1.5 | 0.5 | steareth-20 + Ethomeen T/25 | Aerosil 380 | | propylene glycol |
| F-107 | 480 | | 4.5 + 2.3 | 1.5 | 0.5 | steareth-20 + Ethomeen T/25 | Aerosil 380 | | propylene glycol |
| F-108 | 480 | | 4.5 | 1.5 | | steareth-20 | Aerosil blend 2 | | |
| F-109 | 480 | | 6.0 | 1.5 | | steareth-20 | Aerosil blend 2 | | |
| F-110 | 480 | | 4.5 + 1.0 | 1.5 | 0.5 | steareth-20 + Ethomeen T/25 | Aerosil blend 2 | | propylene glycol |
| F-111 | 480 | | 4.5 | 1.5 | | steareth-30 | Aerosil blend 2 | | |
| F-112 | 480 | | 4.5 + 1.0 | 1.5 | 0.5 | steareth-20 + Ethomeen T/25 | Aerosil blend 2 | | propylene glycol |
| F-113 | 480 | | 6.0 | 1.5 | | steareth-30 | Aerosil blend 2 | | |
| F-114 | 480 | | 4.5 + 2.3 | 1.5 | 0.5 | steareth-20 + Ethomeen T/25 | Aerosil blend 2 | | propylene glycol |
| F-115 | 480 | | 10.0 | 1.5 | | steareth-20 | Aerosil blend 2 | | |
| F-116 | 480 | | 4.5 | 1.5 | | ceteareth-27 | Aerosil 380 | | |
| F-117 | 480 | | 6.0 | 1.5 | | ceteareth-27 | Aerosil 380 | | |
| F-118 | 480 | | 4.5 | 1.5 | | ceteareth-27 | Aerosil blend 2 | | |
| F-119 | 480 | | 6.0 | 1.5 | | ceteareth-27 | Aerosil blend 2 | | |
| F-120 | 480 | | 4.5 | 1.5 | | ceteareth-27 | Al oxide C | | |
| F-121 | 480 | | 6.0 | 1.5 | | ceteareth-27 | Al oxide C | | |

Aerosil blend 1: Aerosil MOX-80 + Aerosil MOX-170 (1:1)
Aerosil blend 2: Aerosil MOX-80 + Aerosil 380 (1:2)

The above compositions were prepared by process (ix) as described in the Examples.

Aqueous compositions tested in the field comprising soybean lecithin (45% phospholipid, Avanti), alkylether surfactant and fatty acid ester have included:

| Field composition | Gly-phosate g a.e./l | Lecithin | MON 0818 | Fatty acid ester | Surfactant | Type of surfactant | Type of fatty acid ester |
|---|---|---|---|---|---|---|---|
| F-136 | 360 | 6.0 | 4.5 | 1.5 | 3.0 + 4.5 | ceteareth-27 + Ethomeen T/25 | Bu stearate |
| F-138 | 228 | 0.8 | | 3.8 | 3.0 + 3.0 | ceteareth-27 + Ethomeen T/25 | Bu stearate |
| F-139 | 228 | 1.5 | | 1.5 | 3.0 + 3.0 | Ethomeen T/25 ceteareth-27 + Ethomeen T/25 | Bu stearate |

The above compositions were prepared by process (x) as described in the Examples.

Dry compositions tested in the field have included:

| Field composition | Glyphosate a.e. | Butyl stearate | Sur- factant | Colloidal particulate | Other | Type of Other surfactant | Type of colloidal particulate | Other ingredients |
|---|---|---|---|---|---|---|---|---|
| F-156 | 64 | | 25.0 | 2.0 | | steareth-20 | Aerosil blend 1 | |
| F-157 | 68 | | 20.0 | 2.0 | | steareth-20 | Aerosil blend 1 | |
| F-158 | 72 | | 15.0 | 2.0 | | steareth-20 | Aerosil blend 1 | |
| F-159 | 64 | | 25.0 | 1.0 | | ceteth-20 | Aerosil 380 | |
| F-160 | 65 | | 25.0 | 1.0 | | steareth-20 | Aerosil 380 | |
| F-161 | 65 | | 25.0 | 1.0 | | oleth-20 | Aerosil 380 | |
| F-166 | 68 | | 20.0 | 2.0 | | steareth-20 | Aerosil blend 1 | |
| F-167 | 66 | 2.0 | 20.0 | 2.0 | | steareth-20 | Aerosil blend 1 | |
| F-168 | 68 | | 20.0 | 2.0 | | oleth-20 | Aerosil blend 1 | |
| F-169 | 66 | 2.0 | 20.0 | 2.0 | | oleth-20 | Aerosil blend 1 | |
| F-170 | 66 | 2.0 | 20.0 | 2.0 | | ceteareth-27 | Aerosil blend 1 | |
| F-171 | 48 | | 14.1 | | 36.1 | ceteareth-27 | | $NH_4$ phosphate |
| F-172 | 65 | | 20.0 | | 5.0 | ceteareth-27 | | Na acetate |
| F-173 | 70 | | 20.0 | | | ceteareth-27 | | |

Aerosil blend 1: Aerosil MOX-80 + Aerosil MOX-170 (1:1)

The above compositions were prepared by the process described for dry granular compositions in Example 40.

EXAMPLES

In the following Examples illustrative of the invention, greenhouse tests were conducted to evaluate relative herbicidal effectiveness of glyphosate compositions. Compositions included for comparative purposes included the following:

Formulation B: which consists of 41% by weight of glyphosate IPA salt in aqueous solution. This formulation is sold in the U.S.A. by Monsanto Company under the ACCORD® trademark.

Formulation C: which consists of 41% by weight of glyphosate IPA salt in aqueous solution with a coformulant (15% by weight) of a surfactant (MON 0818 of Monsanto Company) based on polyoxyethylene (15) tallowamine. This formulation is sold in Canada by Monsanto Company under the ROUNDUP® trademark.

Formulation J: which consists of 41% by weight of glyphosate IPA salt in aqueous solution, together with surfactant. This formulation is sold in the U.S.A. by Monsanto Company under the ROUNDUP® ULTRA trademark.

Formulation K: which consists of 75% by weight of glyphosate ammonium salt together with surfactant, as a water-soluble dry granular formulation. This formulation is sold in Australia by Monsanto Company under the ROUNDUP® DRY trademark.

Formulations B, C and J contain 356 grams of glyphosate acid equivalent per liter (g a.e./l). Formulation K contains 680 grams of glyphosate acid equivalent per kilogram (g a.e./kg).

Various proprietary excipients were used in compositions of the Examples. They may be identified as follows:

| Trade name | Manufacturer | Chemical description |
|---|---|---|
| Aerosil 90 | Degussa | amorphous silica, 90 $m^2/g$ |
| Aerosil 380 | Degussa | amorphous silica, 380 $m^2/g$ |
| Aerosil MOX-80 | Degussa | amorphous silica/aluminum oxide, 80 $m^2/g$ |
| Aerosil MOX-170 | Degussa | amorphous silica/aluminum oxide, 170 $m^2/g$ |
| Aerosil OX-50 | Degussa | amorphous silica, 50 $m^2/g$ |
| Agrimul PG-2069 | Henkel | $C_{9-11}$ alkylpolyglycoside |
| Arcosolve DPM | Arco | dipropyleneglycol monomethyl ether |
| Dowanol PNB | Dow | propylene glycol n-butyl ether |
| Dowanol TPNB | Dow | tripropylene glycol n-butyl ether |
| Emerest 2661 | Henkel | PEG-12 laurate |
| Ethomeen T/25 | Akzo | tallowamine 15EO |
| Fluorad FC-754 | 3M | fluorinated alkyl quaternary ammonium chloride |
| Fluorad FC-760 | 3M | fluorinated alkanol EO |
| Genapol UD-110 | Hoechst | $C_{11}$ oxo alcohol 11EO |
| MON 0818 | Monsanto | tallowamine 15EO-based surfactant |
| Neodol 1-12 | Shell | $C_{11}$ linear alcohol 12EO |
| Neodol 1-9 | Shell | $C_{11}$ linear alcohol 9EO |
| Neodol 25-12 | Shell | $C_{12-15}$ linear alcohol 12EO |
| Neodol 25-20 | Shell | $C_{12-15}$ linear alcohol 20EO |
| Neodol 25-3 | Shell | $C_{12-15}$ linear alcohol 3EO |
| Neodol 45-13 | Shell | $C_{14-15}$ linear alcohol 13EO |
| Neodox 25-11 | Shell | $C_{12-15}$ linear alcohol ethoxycarboxylate 11EO |
| Orchex 796 | Exxon | paraffinic oil |
| Pluronic F-108 | BASF | 128EO-54PO-128EO block copolymer |
| Pluronic F-127 | BASF | 98EO-67PO-98EO block copolymer |
| Pluronic F-68 | BASF | 75EO-30PO-75EO block copolymer |
| Sident 9 | Degussa | abrasive silica, 50 $m^2/g$ |
| Sipernat 22 | Degussa | hydrophilic precipitated silica, 190 $m^2/g$, av. aggregate size 100 $\mu m$ |
| Sipernat 22S | Degussa | hydrophilic precipitated silica, 190 $m^2/g$, av. aggregate size <100 $\mu m$ |
| Span 60 | ICI | sorbitan monostearate |
| Span 80 | ICI | sorbitan monooleate |
| Stepfac 8170 | Stepan | nonylphenol EO phosphate |
| Surfynol 104 | Air Products | tetramethyldecyne diol |
| Tergitol 15-S-15 | Union Carbide | $C_{15}$ branched secondary alcohol 15EO |
| Tergitol 15-S-20 | Union Carbide | $C_{15}$ branched secondary alcohol 20EO |
| Tergitol 15-S-30 | Union Carbide | $C_{15}$ branched secondary alcohol 30EO |
| Tergitol 15-S-40 | Union Carbide | $C_{15}$ branched secondary |

-continued

| Trade name | Manufacturer | Chemical description |
| --- | --- | --- |
| | | alcohol 40EO |
| Tween 20 | ICI | sorbitan monolaurate 20EO |
| Tween 80 | ICI | sorbitan monooleate 20EO |
| Velvetex AB-45 | Henkel | cocobetaine |

Fatty alcohol ethoxylate (alkylether) surfactants are referred to in the Examples by their generic names as given in the International Cosmetic Ingredient Dictionary, 6th Edition, 1995 (Cosmetic, Toiletry and Fragrance Association, Washington, D.C.). They were interchangeably sourced from various manufacturers, for example:

Laureth-23: Brij 35 (ICI), Trycol 5964 (Henkel).
Ceteth-10: Brij 56 (ICI).
Ceteth-20: Brij 58 (ICI).
Steareth-10: Brij 76 (ICI).
Steareth-20: Brij 78 (ICI), Emthox 5888-A (Henkel), STA-20 (Heterene).
Steareth-30: STA-30 (Heterene).
Steareth-100: Brij 700 (ICI).
Ceteareth-15: CS-15 (Heterene).
Ceteareth-20: CS-20 (Heterene).
Ceteareth-27: Plurafac A-38 (BASF).
Ceteareth-55: Plurafac A-39 (BASF).
Oleth-2: Brij 92 (ICI).
Oleth-10: Brij 97 (ICI).
Oleth-20: Brij 98 (ICI), Trycol 5971 (Henkel).

Where a proprietary excipient is a surfactant supplied as a solution in water or other solvent, the amount to be used was calculated on a true surfactant basis, not an "as is" basis. For example, Fluorad FC-135 is supplied as 50% true surfactant, together with 33% isopropanol and 17% water; thus to provide a composition containing 0.1% w/w Fluorad FC-135 as reported herein, 0.2 g of the product as supplied was included in 100 g of the composition. The amount of lecithin, however, is always reported herein on an "as is" basis, regardless of the content of phospholipid in the lecithin sample used.

Spray compositions of the Examples contained an exogenous chemical, such as glyphosate IPA salt, in addition to the excipient ingredients listed. The amount of exogenous chemical was selected to provide the desired rate in grams per hectare (g/ha) when applied in a spray volume of 93 l/ha. Several exogenous chemical rates were applied for each composition. Thus, except where otherwise indicated, when spray compositions were tested, the concentration of exogenous chemical varied in direct proportion to exogenous chemical rate, but the concentration of excipient ingredients was held constant across different exogenous chemical rates.

Concentrate compositions were tested by dilution, dissolution or dispersion in water to form spray compositions. In these spray compositions prepared from concentrates, the concentration of excipient ingredients varied with that of exogenous chemical.

Many of the Examples feature aqueous concentrate compositions of the invention. Except where otherwise indicated, these aqueous concentrate compositions were prepared by the following general processes (v) to (x).

(v) A weighed amount of lecithin powder of the type indicated was placed in a beaker and deionized water was added in sufficient quantity to provide, after sonication as detailed below, a lecithin stock at a convenient concentration, normally in the range from 10% to 20% w/w and typically 15% w/w. The beaker and its contents were then placed in a Fisher Sonic Dismembrator, Model 550, fitted with a 2.4 cm probe tip with the pulse period set at 15 seconds with 1 minute intervals between pulses to allow cooling. Power output was set at level 8. After a total of 3 minutes of sonication (12 pulse periods) the resulting lecithin stock was finally adjusted to the desired concentration if necessary with deionized water. To prepare an aqueous concentrate formulation, the following ingredients were mixed in the appropriate proportions with mild agitation, normally in the order given although this was sometimes varied and was found in some cases to affect the physical stability of the concentrate formulation: (a) exogenous chemical, for example glyphosate IPA salt as a 62% w/w solution at pH 4.4–4.6; (b) lecithin stock; (c) other ingredients if required; and (d) water.

(vi) Water-in-oil-in-water (W/O/W) multiple emulsions were prepared as follows. First a water-in-oil emulsion was prepared. To do this, the required amounts of the selected oil and a first emulsifier (referred to in the Examples as "emulsifier #1") were mixed thoroughly. If it was desired to prepare the formulation with glyphosate in the inner aqueous phase, a measured amount of concentrated (62% w/w) aqueous solution of glyphosate IPA salt was added to the mixture of oil and first emulsifier with agitation to ensure homogeneity. The amount of water required in the inner aqueous phase was then added to complete the water-in-oil emulsion, which was finally subjected to high-shear mixing, typically using a Silverson L4RT-A mixer fitted with a fine emulsor screen operated for 3 minutes at 10,000 rpm. The required amount of a second emulsifier (referred to in the Examples as "emulsifier #2") was next added to the water-in-oil emulsion with agitation to ensure homogeneity. If it was desired to prepare the formulation with glyphosate in the outer aqueous phase, a measured amount of concentrated (62% w/w) aqueous solution of glyphosate IPA salt was added to the blend of the water-in-oil emulsion and the second emulsifier with further agitation. To complete the water-in-oil-in-water multiple emulsion composition, the amount of water required in the outer aqueous phase was added. The composition was finally subjected to high-shear mixing, typically using a Silverson L4RT-A mixer fitted with a medium emulsor screen, operated for 3 minutes at 7,000 rpm.

(vii) Oil-in-water (O/W) emulsions were prepared as follows. The required amount of the selected oil and surfactant (sometimes referred to in the Examples as "emulsifier #2" as it corresponds to the second emulsifier in process (vi)) were mixed thoroughly. If the surfactant selected was not free-flowing at ambient temperature, heat was applied to bring the surfactant into a flowable condition before mixing with the oil. A measured amount of concentrated (62% w/w) aqueous solution of glyphosate IPA salt was added to the surfactant-oil mixture with agitation. The required amount of water was added to bring the concentration of glyphosate and other ingredients to the desired level. The composition was finally subjected to high-shear mixing, typically using a Silverson L4RT-A mixer fitted with a medium emulsor screen, operated for 3 minutes at 7,000 rpm.

(viii) Surfactant-containing aqueous solution concentrates having no oil component were prepared as follows. A concentrated (62% w/w) aqueous solution of glyphosate IPA salt was added in the desired amount to a weighed quantity of the selected surfactant(s). If the surfactant selected is not free-flowing at ambient temperature, heat was applied to bring the surfactant into a flowable condition before adding the glyphosate solution. The required amount of water was added to bring the concentration of glyphosate and other ingredients to the desired level. The composition was finally subjected to high-shear mixing, typically using a Silverson L4RT-A mixer fitted with a medium emulsor screen, operated for 3 minutes at 7,000 rpm.

(ix) For compositions containing a colloidal particulate, the required amount by weight of the selected colloidal particulate was suspended in a concentrated (62% w/w) aqueous solution of glyphosate IPA salt and agitated with cooling to ensure homogeneity. To the resulting suspension was added the required amount by weight of the selected surfactant(s). For a surfactant which is not free-flowing at ambient temperature, heat was applied to bring the surfactant into a flowable condition before adding it to the suspension. In those instances where an oil, such as butyl stearate, was also to be included in the composition, the oil was first thoroughly mixed with the surfactant and the surfactant-oil mixture added to the suspension. To complete the aqueous concentrate, the required amount of water was added to bring the concentration of glyphosate and other ingredients to the desired level. The concentrate was finally subjected to high-shear mixing, typically using a Silverson L4RT-A mixer fitted with a medium emulsor screen, operated for 3 minutes at 7,000 rpm.

(x) The procedure for preparing aqueous concentrate formulations containing lecithin and butyl stearate was different from that followed for other lecithin-containing concentrates. Exogenous chemical, for example glyphosate IPA salt, was first added, with mild agitation, to deionized water in a formulation jar. The selected surfactant (other than lecithin) was then added, while continuing the agitation, to form a preliminary exogenous chemical/surfactant mixture. Where the surfactant is not free-flowing at ambient temperature, the order of addition was not as above. Instead, the non-free-flowing surfactant was first added to water together with any other surfactant (other than lecithin) required in the composition, and was then heated to 55° C. in a shaker bath for 2 hours. The resulting mixture was allowed to cool, then exogenous chemical was added with mild agitation to form the preliminary exogenous chemical/surfactant mixture. A weighed amount of the selected lecithin was added to the preliminary exogenous chemical/surfactant mixture, with stirring to break up lumps. The mixture was left for about 1 hour to allow the lecithin to hydrate, then butyl stearate was added, with further stirring until no phase separation occurred. The mixture was then transferred to a microfluidizer (Microfluidics International Corporation, Model M-110F) and microfluidized for 3 to 5 cycles at 10,000 psi (69 MPa). In each cycle, the formulation jar was rinsed with microfluidized mixture. In the last cycle, the finished composition was collected in a clean dry beaker.

The following procedure was used for testing compositions of the Examples to determine herbicidal effectiveness, except where otherwise indicated.

Seeds of the plant species indicated were planted in 85 mm square pots in a soil mix which was previously steam sterilized and prefertilized with a 14-14-14 NPK slow release fertilizer at a rate of 3.6 kg/m$^3$. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and about 18° C. during the night. Plants were sub-irrigated throughout the test to ensure adequate soil moisture levels.

Pots were assigned to different treatments in a fully randomized experimental design with 3 replications. A set of pots was left untreated as a reference against which effects of the treatments could later be evaluated.

Application of glyphosate compositions was made by spraying with a track sprayer fitted with a 9501E nozzle calibrated to deliver a spray volume of 93 liters per hectare (l/ha) at a pressure of 166 kilopascals (kPa). After treatment, pots were returned to the greenhouse until ready for evaluation.

Treatments were made using dilute aqueous compositions. These could be prepared as spray compositions directly from their ingredients, or by dilution with water of preformulated concentrate compositions.

For evaluation of herbicidal effectiveness, all plants in the test were examined by a single practiced technician, who recorded percent inhibition, a visual measurement of the effectiveness of each treatment by comparison with untreated plants. Inhibition of 0% indicates no effect, and inhibition of 100% indicates that all of the plants are completely is dead. Inhibition of 85% or more is in most cases considered acceptable for normal herbicidal use; however in greenhouse tests such as those of the Examples it is normal to apply compositions at rates which give less than 85% inhibition, as this makes it easier to discriminate among compositions having different levels of effectiveness.

Example 1

Aqueous concentrate compositions were prepared containing glyphosate IPA salt and excipient ingredients as shown in Table 1a. These compositions are water-in-oil-in-water multiple emulsions and were prepared by process (vi) described above.

TABLE 1a

| Conc. comp. | Glyphosate a.e. | Butyl stearate | Emulsifier #1 | Emulsifier #2 | % in inner aq. phase Water | % in inner aq. phase Glyphosate | Emulsifier #1 | Emulsifier #2 |
|---|---|---|---|---|---|---|---|---|
| 1-01 | 10 | 18.0 | 3.0 | 5.0 | 9.0 | 20 | Span 80 | Tween 20 |
| 1-02 | 10 | 7.5 | 3.0 | 5.0 | 4.5 | 20 | Span 80 | Tween 20 |
| 1-03 | 10 | 7.5 | 3.0 | 10.0 | 4.5 | 20 | Surfynol 104 | Neodol 25-12 |
| 1-04 | 10 | 7.5 | 3.0 | 10.0 | 4.5 | 20 | Surfynol 104 | Neodol 25-20 |
| 1-05 | 10 | 7.5 | 3.0 | 10.0 | 4.5 | 20 | Surfynol 104 | Tergitol 15-S-15 |
| 1-06 | 10 | 7.5 | 3.0 | 10.0 | 4.5 | 20 | Surfynol 104 | Tergitol 15-S-20 |
| 1-07 | 10 | 7.5 | 3.0 | 10.0 | 4.5 | 20 | Surfynol 104 | Tween 20 |
| 1-08 | 10 | 7.5 | 3.0 | 10.0 | 4.5 | 20 | Surfynol 104 | ceteareth-55 |
| 1-09 | 10 | 7.5 | 3.0 | 10.0 | 4.5 | 20 | Surfynol 104 | Tergitol 15-S-30 |
| 1-10 | 10 | 7.5 | 3.0 | 10.0 | 4.5 | 20 | Neodol 25-3 | ceteareth-55 |
| 1-11 | 10 | 7.5 | 3.0 | 10.0 | 4.5 | 20 | Neodol 25-3 | Tergitol 15-S-30 |
| 1-12 | 10 | 7.5 | 3.0 | 10.0 | 4.5 | 20 | Span 60 | ceteareth-55 |
| 1-13 | 10 | 7.5 | 3.0 | 10.0 | 4.5 | 20 | Span 60 | Tergitol 15-S-30 |
| 1-14 | 10 | 7.5 | 3.0 | 10.0 | 4.5 | 20 | oleth-2 | ceteareth-55 |
| 1-15 | 10 | 7.5 | 3.0 | 10.0 | 4.5 | 20 | oleth-2 | Tergitol 15-S-30 |
| 1-16 | 10 | 7.5 | 3.0 | 10.0 | 4.5 | 20 | Emid 6545 | ceteareth-55 |
| 1-17 | 10 | 7.5 | 3.0 | 10.0 | 4.5 | 20 | Emid 6545 | Tergitol 15-S-30 |

Velvetleaf (*Abutilon theophrasti*, ABUTH) and Japanese millet (*Echinochloa crus-galli*, ECHCF) plants were grown and treated by the standard procedures given above. Applications of spray compositions were made 35 days after planting ABUTH and 33 days after planting ECHCF, and evaluation of herbicidal inhibition was done 17 days after application.

Formulations B, C and J were applied as comparative treatments. Results, averaged for all replicates of each treatment, are shown in Table 1b.

TABLE 1b

| Concentrate composition | Glyphosate rate g a.e./ha | % Inhibition ABUTH | % Inhibition ECHCF |
|---|---|---|---|
| Formulation B | 150 | 0 | 0 |
| | 250 | 35 | 40 |
| | 350 | 50 | 63 |
| | 450 | 60 | 43 |
| Formulation C | 150 | 63 | 63 |
| | 250 | 80 | 96 |
| | 350 | 92 | 98 |
| | 450 | 98 | 87 |
| Formulation J | 150 | 43 | 30 |
| | 250 | 75 | 85 |
| | 350 | 82 | 98 |
| | 450 | 96 | 95 |
| 1-01 | 150 | 65 | 53 |
| | 250 | 85 | 70 |
| | 350 | 90 | 87 |
| | 450 | 98 | 73 |
| 1-02 | 150 | 63 | 5 |
| | 250 | 78 | 53 |
| | 350 | 88 | 80 |
| | 450 | 97 | 87 |
| 1-03 | 150 | 75 | 0 |
| | 250 | 87 | 22 |
| | 350 | 88 | 72 |
| | 450 | 97 | 17 |
| 1-04 | 150 | 84 | 0 |
| | 250 | 90 | 10 |
| | 350 | 95 | 70 |
| | 450 | 98 | 60 |

TABLE 1b-continued

| Concentrate composition | Glyphosate rate g a.e./ha | % Inhibition ABUTH | % Inhibition ECHCF |
|---|---|---|---|
| 1-05 | 150 | 77 | 0 |
| | 250 | 83 | 3 |
| | 350 | 93 | 30 |
| | 450 | 95 | 10 |
| 1-06 | 150 | 72 | 0 |
| | 250 | 83 | 47 |
| | 350 | 94 | 60 |
| | 450 | 98 | 20 |
| 1-07 | 150 | 75 | 0 |
| | 250 | 77 | 40 |
| | 350 | 96 | 47 |
| | 450 | 96 | 50 |
| 1-08 | 150 | 87 | 40 |
| | 250 | 97 | 82 |
| | 350 | 99 | 83 |
| | 450 | 100 | 77 |
| 1-19 | 150 | 82 | 10 |
| | 250 | 82 | 40 |
| | 350 | 96 | 67 |
| | 450 | 97 | 67 |
| 1-10 | 150 | 82 | 13 |
| | 250 | 94 | 83 |
| | 350 | 99 | 85 |
| | 450 | 99 | 83 |
| 1-11 | 150 | 73 | 17 |
| | 250 | 83 | 60 |
| | 350 | 88 | 73 |
| | 450 | 96 | 63 |
| 1-12 | 150 | 80 | 20 |
| | 250 | 93 | 85 |
| | 350 | 96 | 82 |
| | 450 | 96 | 82 |
| 1-13 | 150 | 78 | 20 |
| | 250 | 83 | 50 |
| | 350 | 92 | 90 |
| | 450 | 92 | 85 |
| 1-14 | 150 | 80 | 30 |
| | 250 | 97 | 85 |
| | 350 | 99 | 99 |
| | 450 | 97 | 96 |
| 1-15 | 150 | 82 | 30 |
| | 250 | 87 | 75 |
| | 350 | 99 | 92 |
| | 450 | 99 | 93 |
| 1-16 | 150 | 82 | 53 |

TABLE 1b-continued

| Concentrate composition | Glyphosate rate g a.e./ha | % Inhibition ABUTH | % Inhibition ECHCF |
|---|---|---|---|
|  | 250 | 96 | 82 |
|  | 350 | 96 | 97 |
|  | 450 | 87 | 82 |
| 1-17 | 150 | 72 | 20 |
|  | 250 | 80 | 63 |
|  | 350 | 92 | 75 |
|  | 450 | 95 | 87 |

Considerable variation was seen in herbicidal effectiveness of water-in-oil-in-water multiple emulsions of this Example, especially on *ECHCF*. Among the most efficacious were 1-08, 1-10, 1-12, 1-14 and 1-16. All of these contained a $C_{16-18}$ alkylether surfactant, ceteareth-55. When Tergitol 15-S-30, a $C_{12-15}$ secondary alkylether surfactant, replaced ceteareth-55, as in 1-09, 1-11, 1-13, 1-15 and 1-17, herbicidal effectiveness, at least on *ECHCF*, was in most cases markedly reduced.

Example 2

Aqueous concentrate compositions were prepared containing glyphosate IPA salt and excipient ingredients as shown in Table 2a. Concentrate compositions 2-01 and 2-02 are water-in-oil-in-water multiple emulsions and were prepared by process (vi), using Span 80 as emulsifier #1. Concentrate compositions 2-03 to 2-12 and 2-14 to 2-17 are oil-in-water emulsions and were prepared by process (vii). Concentrate composition 2-13 is an aqueous solution concentrate and was prepared by process (viii), the component indicated below as "emulsifier #2" being the surfactant component.

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting *ABUTH* and 19 days after planting *ECHCF*, and evaluation of herbicidal inhibition was done 18 days after application.

Formulations B, C and J were applied as comparative treatments. Results, averaged for all replicates of each treatment, are shown in Table 2b.

TABLE 2b

| Concentrate composition | Glyphosate rate g a.e./ha | % Inhibition ABUTH | % Inhibition ECHCF |
|---|---|---|---|
| Formulation B | 150 | 0 | 30 |
|  | 250 | 10 | 40 |
|  | 350 | 37 | 73 |
|  | 450 | 58 | 68 |
| Formulation C | 150 | 42 | 79 |
|  | 250 | 77 | 98 |
|  | 350 | 99 | 97 |
|  | 450 | 97 | 93 |
| Formulation J | 150 | 43 | 67 |
|  | 250 | 73 | 90 |
|  | 350 | 94 | 98 |
|  | 450 | 77 | 78 |
| 2-01 | 150 | 58 | 76 |
|  | 250 | 75 | 77 |
|  | 350 | 88 | 93 |
|  | 450 | 95 | 83 |
| 2-02 | 150 | 27 | 63 |
|  | 250 | 60 | 87 |
|  | 350 | 82 | 98 |
|  | 450 | 77 | 92 |
| 2-03 | 150 | 47 | 76 |
|  | 250 | 65 | 92 |
|  | 350 | 94 | 99 |
|  | 450 | 95 | 91 |
| 2-04 | 150 | 70 | 86 |
|  | 250 | 86 | 95 |
|  | 350 | 97 | 98 |
|  | 450 | 99 | 90 |
| 2-05 | 150 | 42 | 80 |

TABLE 2a

| Conc. comp. | Glyphosate a.e. | Butyl stearate | Span 80 | Emulsifier #2 | % in inner aq. Phase Water | % in inner aq. Phase Glyphosate | Emulsifier #2 |
|---|---|---|---|---|---|---|---|
| 2-01 | 10 | 18.0 | 3.0 | 5.0 | 12.2 | 20 | Tween 20 |
| 2-02 | 10 | 7.5 | 3.0 | 5.0 | 5.3 | 20 | Tween 20 |
| 2-03 | 10 | 1.0 |  | 10.0 |  |  | Neodol 25-20 |
| 2-04 | 10 | 3.0 |  | 10.0 |  |  | Neodol 25-20 |
| 2-05 | 10 | 1.0 |  | 5.0 |  |  | Neodol 25-20 |
| 2-06 | 10 | 3.0 |  | 5.0 |  |  | Neodol 25-20 |
| 2-07 | 15 | 1.0 |  | 10.0 |  |  | Neodol 25-20 |
| 2-08 | 15 | 3.0 |  | 10.0 |  |  | Neodol 25-20 |
| 2-09 | 15 | 1.0 |  | 5.0 |  |  | Neodol 25-20 |
| 2-10 | 15 | 3.0 |  | 5.0 |  |  | Neodol 25-20 |
| 2-11 | 20 | 1.0 |  | 5.0 |  |  | Neodol 25-20 |
| 2-12 | 20 | 1.0 |  | 10.0 |  |  | Neodol 25-20 |
| 2-13 | 10 |  |  | 10.0 |  |  | Neodol 25-20 |
| 2-14 | 10 | 7.5 |  | 10.0 |  |  | Neodol 25-20 |
| 2-15 | 10 | 7.5 |  | 10.0 |  |  | Neodol 25-12 |
| 2-16 | 10 | 7.5 |  | 10.0 |  |  | steareth-20 |
| 2-17 | 10 | 7.5 |  | 10.0 |  |  | oleth-20 |

TABLE 2b-continued

| Concentrate composition | Glyphosate rate g a.e./ha | % Inhibition ABUTH | % Inhibition ECHCF |
|---|---|---|---|
|  | 250 | 72 | 90 |
|  | 350 | 90 | 93 |
|  | 450 | 99 | 96 |
| 2-06 | 150 | 48 | 57 |
|  | 250 | 78 | 92 |
|  | 350 | 94 | 99 |
|  | 450 | 96 | 92 |
| 2-07 | 150 | 78 | 95 |
|  | 250 | 96 | 96 |
|  | 350 | 98 | 98 |
|  | 450 | 100 | 97 |
| 2-08 | 150 | 88 | 96 |
|  | 250 | 98 | 98 |
|  | 350 | 100 | 99 |
|  | 450 | 100 | 99 |
| 2-09 | 150 | 82 | 93 |
|  | 250 | 94 | 96 |
|  | 350 | 99 | 97 |
|  | 450 | 99 | 93 |
| 2-10 | 150 | 72 | 83 |
|  | 250 | 97 | 93 |
|  | 350 | 99 | 100 |
|  | 450 | 100 | 98 |
| 2-11 | 150 | 87 | 83 |
|  | 250 | 98 | 97 |
|  | 350 | 100 | 99 |
|  | 450 | 100 | 99 |
| 2-12 | 150 | 93 | 99 |
|  | 250 | 99 | 99 |
|  | 350 | 99 | 97 |
|  | 450 | 100 | 99 |
| 2-13 | 150 | 70 | 90 |
|  | 250 | 91 | 88 |
|  | 350 | 97 | 94 |
|  | 450 | 99 | 86 |
| 2-14 | 150 | 67 | 76 |
|  | 250 | 93 | 80 |
|  | 350 | 98 | 95 |
|  | 450 | 95 | 78 |
| 2-15 | 150 | 68 | 65 |
|  | 250 | 90 | 87 |
|  | 350 | 97 | 80 |
|  | 450 | 98 | 93 |
| 2-16 | 150 | 83 | 73 |
|  | 250 | 90 | 93 |
|  | 350 | 99 | 100 |
|  | 450 | 100 | 100 |
| 2-17 | 150 | 80 | 66 |
|  | 250 | 98 | 77 |
|  | 350 | 99 | 83 |
|  | 450 | 100 | 85 |

Very high herbicidal activity was evident in compositions 2-13 to 2-17, which have a very high ratio of surfactant to glyphosate a.e. of 1:1. Activity was too high to clearly distinguish among these compositions, but 2-16 and 2-17, containing steareth-20 and oleth-20 respectively, exbited greater effectiveness on *ABUTH* at the lowest glyphosate rate than 2-14 and 2-15, containing Neodol 25-20 and Neodol 25-12 respectively.

Example 3

Aqueous concentrate compositions were prepared containing glyphosate IPA salt and excipient ingredients as shown in Table 3a. Concentrate compositions 3-01 and 3-02 are water-in-oil-in-water multiple emulsions and were prepared by process (vi), using Span 80 as emulsifier #1. Concentrate compositions 3-03 to 3-12 and 3-14 to 3-17 are oil-in-water emulsions and were prepared by process (vii). Concentrate composition 3-13 is an aqueous solution concentrate and was prepared by process (viii), the component indicated below as "emulsifier #2" being the surfactant component.

TABLE 3a

| Conc. comp. | % w/w Glyphosate a.e. | % w/w Butyl stearate | % w/w Span 80 | % w/w Emulsifier #2 | % in inner aq. Phase Water | % in inner aq. Phase Glyphosate | Emulsifier #2 |
|---|---|---|---|---|---|---|---|
| 3-01 | 10 | 18.0 | 3.0 | 5.0 | 12.2 | 20 | Tween 20 |
| 3-02 | 10 | 7.5 | 3.0 | 5.0 | 5.3 | 20 | Tween 20 |
| 3-03 | 10 | 1.0 |  | 10.0 |  |  | Tween 80 |
| 3-04 | 10 | 3.0 |  | 10.0 |  |  | Tween 80 |
| 3-05 | 10 | 1.0 |  | 5.0 |  |  | Tween 80 |
| 3-06 | 10 | 3.0 |  | 5.0 |  |  | Tween 80 |
| 3-07 | 15 | 1.0 |  | 10.0 |  |  | Tween 80 |
| 3-08 | 15 | 3.0 |  | 10.0 |  |  | Tween 80 |
| 3-09 | 15 | 1.0 |  | 5.0 |  |  | Tween 80 |
| 3-10 | 15 | 3.0 |  | 5.0 |  |  | Tween 80 |
| 3-11 | 20 | 1.0 |  | 5.0 |  |  | Tween 80 |
| 3-12 | 20 | 1.0 |  | 10.0 |  |  | Tween 80 |
| 3-13 | 10 |  |  | 10.0 |  |  | Tween 80 |
| 3-14 | 10 | 7.5 |  | 10.0 |  |  | Tween 80 |
| 3-15 | 10 | 7.5 |  | 10.0 |  |  | Neodol 25-20 |
| 3-16 | 10 | 7.5 |  | 10.0 |  |  | steareth-20 |
| 3-17 | 10 | 7.5 |  | 10.0 |  |  | oleth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 19 days after planting ECHCF, and evaluation of herbicidal inhibition was done 18 days after application.

Formulations B, C and J were applied as comparative treatments. Results, averaged for all replicates of each treatment, are shown in Table 3b.

TABLE 3b

| Concentrate composition | Glyphosate rate g a.e./ha | % Inhibition ABUTH | % Inhibition ECHCF |
|---|---|---|---|
| Formulation B | 150 | 0 | 0 |
| | 250 | 3 | 10 |
| | 350 | 17 | 20 |
| | 450 | 20 | 30 |
| Formulation C | 150 | 70 | 33 |
| | 250 | 80 | 70 |
| | 350 | 85 | 80 |
| | 450 | 97 | 77 |
| Formulation J | 150 | 7 | 20 |
| | 250 | 70 | 80 |
| | 350 | 78 | 80 |
| | 450 | 83 | 80 |
| 3-01 | 150 | 40 | 7 |
| | 250 | 48 | 20 |
| | 350 | 73 | 23 |
| | 450 | 75 | 30 |
| 3-02 | 150 | 3 | 0 |
| | 250 | 10 | 17 |
| | 350 | 47 | 23 |
| | 450 | 50 | 30 |
| 3-03 | 150 | 0 | 2 |
| | 250 | 33 | 13 |
| | 350 | 63 | 40 |
| | 450 | 68 | 43 |
| 3-04 | 150 | 17 | 7 |
| | 250 | 43 | 20 |
| | 350 | 78 | 63 |
| | 450 | 78 | 63 |
| 3-05 | 150 | 10 | 3 |
| | 250 | 20 | 13 |
| | 350 | 58 | 40 |
| | 450 | 75 | 40 |
| 3-06 | 150 | 3 | 0 |
| | 250 | 27 | 20 |
| | 350 | 60 | 23 |
| | 450 | 72 | 23 |
| 3-07 | 150 | 32 | 10 |
| | 250 | 68 | 20 |
| | 350 | 75 | 50 |
| | 450 | 86 | 60 |
| 3-08 | 150 | 27 | 20 |
| | 250 | 68 | 30 |
| | 350 | 82 | 40 |
| | 450 | 90 | 73 |
| 3-09 | 150 | 43 | 10 |
| | 250 | 60 | 33 |
| | 350 | 72 | 63 |
| | 450 | 75 | 73 |
| 3-10 | 150 | 33 | 10 |
| | 250 | 62 | 30 |
| | 350 | 77 | 60 |
| | 450 | 83 | 70 |
| 3-11 | 150 | 48 | 13 |
| | 250 | 72 | 63 |
| | 350 | 83 | 80 |
| | 450 | 87 | 80 |
| 3-12 | 150 | 23 | 13 |
| | 250 | 60 | 50 |
| | 350 | 75 | 80 |
| | 450 | 86 | 78 |

TABLE 3b-continued

| Concentrate composition | Glyphosate rate g a.e./ha | % Inhibition ABUTH | % Inhibition ECHCF |
|---|---|---|---|
| 3-13 | 150 | 32 | 13 |
| | 250 | 47 | 40 |
| | 350 | 75 | 50 |
| | 450 | 78 | 70 |
| 3-14 | 150 | 27 | 20 |
| | 250 | 75 | 53 |
| | 350 | 82 | 70 |
| | 450 | 92 | 67 |
| 3-15 | 150 | 70 | 20 |
| | 250 | 78 | 30 |
| | 350 | 92 | 80 |
| | 450 | 93 | 80 |
| 3-16 | 150 | 68 | 40 |
| | 250 | 73 | 30 |
| | 350 | 93 | 80 |
| | 450 | 93 | 77 |
| 3-17 | 150 | 73 | 20 |
| | 250 | 85 | 30 |
| | 350 | 93 | 60 |
| | 450 | 95 | 63 |

Compositions 3-16 and 3-17, containing steareth-20 and oleth-20 respectively, exhibited very high herbicidal activity on *ABUTH*. At the very high surfactant to glyphosate a.e. ratio (1:1) of these compositions, no difference was evident between these compositions and an otherwise similar composition (3-15) containing Neodol 25-20 in place of steareth-20 or oleth-20.

Example 4

Aqueous concentrate compositions were prepared containing glyphosate IPA salt and excipient ingredients as shown in Table 4a. All are oil-in-water emulsions and were prepared by process (vii).

TABLE 4a

| | | % w/w | | |
|---|---|---|---|---|
| Concentrate composition | Glyphosate g a.e./l | Butyl stearate | Surfactant | Type of surfactant |
| 4-01 | 163 | 1.00 | 10.0 | Tween 80 |
| 4-02 | 163 | 1.00 | 10.0 | Neodol 25-12 |
| 4-03 | 163 | 1.00 | 10.0 | Neodol 25-20 |
| 4-04 | 163 | 1.00 | 10.0 | steareth-20 |
| 4-05 | 163 | 1.00 | 10.0 | oleth-20 |
| 4-06 | 163 | 1.00 | 10.0 | Tergitol 15-S-40 |
| 4-07 | 163 | 1.00 | 10.0 | Tergitol 15-S-15 |
| 4-08 | 163 | 1.00 | 10.0 | Tergitol 15-S-20 |
| 4-09 | 163 | 0.50 | 10.0 | Tergitol 15-S-40 |
| 4-10 | 163 | 0.50 | 10.0 | Tergitol 15-S-15 |
| 4-11 | 163 | 0.50 | 10.0 | Tergitol 15-S-20 |
| 4-12 | 163 | 0.50 | 5.0 | Tergitol 15-S-40 |
| 4-13 | 163 | 0.50 | 5.0 | Tergitol 15-S-15 |
| 4-14 | 163 | 0.50 | 5.0 | Tergitol 15-S-20 |
| 4-15 | 163 | 0.25 | 10.0 | Tergitol 15-S-40 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 19 days after application.

Formulations B, C and J were applied as comparative treatments. Results, averaged for all replicates of each treatment, are shown in Table 4b.

TABLE 4b

| Concentrate composition | Glyphosate rate g a.e./ha | % Inhibition ABUTH | % Inhibition ECHCF |
|---|---|---|---|
| Formulation B | 150 | 2 | 20 |
|  | 250 | 2 | 30 |
|  | 350 | 5 | 53 |
|  | 450 | 45 | 75 |
| Formulation C | 150 | 45 | 63 |
|  | 250 | 77 | 93 |
|  | 350 | 83 | 99 |
|  | 450 | 93 | 100 |
| Formulation J | 150 | 15 | 40 |
|  | 250 | 70 | 73 |
|  | 350 | 78 | 98 |
|  | 450 | 92 | 99 |
| 4-01 | 150 | 42 | 50 |
|  | 250 | 72 | 89 |
|  | 350 | 80 | 96 |
|  | 450 | 93 | 98 |
| 4-02 | 150 | 45 | 80 |
|  | 250 | 72 | 83 |
|  | 350 | 85 | 91 |
|  | 450 | 97 | 98 |
| 4-03 | 150 | 60 | 80 |
|  | 250 | 75 | 87 |
|  | 350 | 82 | 96 |
|  | 450 | 86 | 99 |
| 4-04 | 150 | 65 | 60 |
|  | 250 | 82 | 70 |
|  | 350 | 93 | 80 |
|  | 450 | 98 | 87 |
| 4-05 | 150 | 72 | 60 |
|  | 250 | 83 | 87 |
|  | 350 | 95 | 93 |
|  | 450 | 98 | 97 |
| 4-06 | 150 | 50 | 45 |
|  | 250 | 68 | 70 |
|  | 350 | 77 | 85 |
|  | 450 | 83 | 90 |
| 4-07 | 150 | 25 | 40 |
|  | 250 | 65 | 50 |
|  | 350 | 80 | 77 |
|  | 450 | 83 | 80 |
| 4-08 | 150 | 37 | 33 |
|  | 250 | 72 | 80 |
|  | 350 | 77 | 87 |
|  | 450 | 80 | 90 |
| 4-09 | 150 | 32 | 47 |
|  | 250 | 65 | 73 |
|  | 350 | 77 | 75 |
|  | 450 | 80 | 94 |
| 4-10 | 150 | 17 | 30 |
|  | 250 | 65 | 70 |
|  | 350 | 75 | 70 |
|  | 450 | 78 | 89 |
| 4-11 | 150 | 35 | 33 |
|  | 250 | 68 | 68 |
|  | 350 | 77 | 77 |
|  | 450 | 92 | 75 |
| 4-12 | 150 | 13 | 35 |
|  | 250 | 57 | 40 |
|  | 350 | 75 | 57 |
|  | 450 | 77 | 83 |
| 4-13 | 150 | 35 | 40 |
|  | 250 | 63 | 43 |
|  | 350 | 77 | 77 |
|  | 450 | 83 | 75 |
| 4-14 | 150 | 30 | 25 |
|  | 250 | 67 | 53 |
|  | 350 | 78 | 85 |
|  | 450 | 83 | 77 |
| 4-15 | 150 | 13 | 37 |
|  | 250 | 65 | 50 |
|  | 350 | 77 | 57 |
|  | 450 | 87 | 82 |

At a surfactant to glyphosate a.e. weight/weight ratio of about 1:1.5, compositions containing steareth-20 or oleth-20 (4-04 and 4-05 respectively) exhibited herbicidal effectiveness on ABUTH similar to one containing Neodol 25-20 (4-03).

Example 5

Aqueous concentrate compositions were prepared containing glyphosate IPA salt and excipient ingredients as shown in Table 5a. All are oil-in-water emulsions and were prepared by process (vii).

TABLE 5a

| Concentrate composition | Glyphosate g a.e./l | Butyl stearate % w/w | Surfactant % w/w | Type of surfactant |
|---|---|---|---|---|
| 5-01 | 163 | 1.0 | 10.0 | Tween 80 |
| 5-02 | 163 | 1.0 | 10.0 | Neodol 25-12 |
| 5-03 | 163 | 1.0 | 10.0 | Neodol 25-20 |
| 5-04 | 163 | 1.0 | 10.0 | steareth-20 |
| 5-05 | 163 | 1.0 | 10.0 | oleth-20 |
| 5-06 | 163 | 1.0 | 10.0 | Tergitol 15-S-40 |
| 5-07 | 163 | 1.0 | 10.0 | Tergitol 15-S-15 |
| 5-08 | 163 | 1.0 | 10.0 | Tergitol 15-S-20 |
| 5-09 | 163 | 0.5 | 10.0 | Tergitol 15-S-40 |
| 5-10 | 163 | 0.3 | 10.0 | Tergitol 15-S-15 |
| 5-11 | 163 | 0.3 | 10.0 | Tergitol 15-S-20 |
| 5-12 | 163 | 0.3 | 10.0 | Tergitol 15-S-40 |
| 5-13 | 163 | 0.3 | 5.0 | Tergitol 15-S-15 |
| 5-14 | 163 | 0.3 | 5.0 | Tergitol 15-S-20 |
| 5-15 | 163 | 0.3 | 5.0 | Tergitol 15-S-40 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 21 days after application.

Formulations B, C and J were applied as comparative treatments. Results, averaged for all replicates of each treatment, are shown in Table 5b.

TABLE 5b

| Concentrate composition | Glyphosate rate g a.e./ha | % Inhibition ABUTH | % Inhibition ECHCF |
|---|---|---|---|
| Formulation B | 150 | 0 | 23 |
|  | 250 | 0 | 40 |
|  | 350 | 5 | 53 |
|  | 450 | 13 | 57 |
| Formulation C | 150 | 0 | 47 |
|  | 250 | 28 | 87 |
|  | 350 | 72 | 98 |
|  | 450 | 97 | 97 |
| Formulation J | 150 | 5 | 40 |
|  | 250 | 20 | 63 |
|  | 350 | 67 | 93 |
|  | 450 | 82 | 92 |
| 5-01 | 150 | 2 | 40 |
|  | 250 | 30 | 50 |
|  | 350 | 50 | 70 |
|  | 450 | 57 | 85 |
| 5-02 | 150 | 10 | 50 |
|  | 250 | 33 | 50 |
|  | 350 | 75 | 72 |
|  | 450 | 75 | 88 |
| 5-03 | 150 | 17 | 53 |
|  | 250 | 60 | 60 |
|  | 350 | 70 | 92 |
|  | 450 | 78 | 94 |

TABLE 5b-continued

| Concentrate composition | Glyphosate rate g a.e./ha | % Inhibition ABUTH | % Inhibition ECHCF |
|---|---|---|---|
| 5-04 | 150 | 57 | 45 |
|  | 250 | 70 | 70 |
|  | 350 | 82 | 93 |
|  | 450 | 83 | 95 |
| 5-05 | 150 | 47 | 45 |
|  | 250 | 70 | 80 |
|  | 350 | 80 | 88 |
|  | 450 | 88 | 92 |
| 5-06 | 150 | 2 | 42 |
|  | 250 | 20 | 60 |
|  | 350 | 35 | 75 |
|  | 450 | 58 | 89 |
| 5-07 | 150 | 0 | 42 |
|  | 250 | 30 | 68 |
|  | 350 | 40 | 75 |
|  | 450 | 77 | 82 |
| 5-08 | 150 | 2 | 40 |
|  | 250 | 25 | 60 |
|  | 350 | 50 | 83 |
|  | 450 | 75 | 86 |
| 5-09 | 150 | 2 | 43 |
|  | 250 | 27 | 83 |
|  | 350 | 40 | 73 |
|  | 450 | 70 | 78 |
| 5-10 | 150 | 2 | 42 |
|  | 250 | 32 | 47 |
|  | 350 | 43 | 63 |
|  | 450 | 70 | 82 |
| 5-11 | 150 | 0 | 30 |
|  | 250 | 25 | 53 |
|  | 350 | 35 | 75 |
|  | 450 | 70 | 75 |
| 5-12 | 150 | 2 | 40 |
|  | 250 | 13 | 57 |
|  | 350 | 25 | 75 |
|  | 450 | 40 | 83 |
| 5-13 | 150 | 5 | 42 |
|  | 250 | 23 | 62 |
|  | 350 | 38 | 63 |
|  | 450 | 67 | 60 |
| 5-14 | 150 | 2 | 33 |
|  | 250 | 13 | 48 |
|  | 350 | 30 | 53 |
|  | 450 | 70 | 88 |
| 5-15 | 150 | 2 | 33 |
|  | 250 | 18 | 48 |
|  | 350 | 30 | 75 |
|  | 450 | 43 | 65 |

In this test, herbicidal effectiveness overall was lower than in the previous Example, particularly on *ABUTH*. In these circumstances, at a surfactant to glyphosate a.e. weight/weight ratio of about 1:1.5, compositions containing steareth-20 or oleth-20 (5-04 and 5-05 respectively) exhibited greater herbicidal effectiveness on both *ABUTH* and *ECHCF* than one containing Neodol 25-20 (5-03).

Example 6

Aqueous concentrate compositions were prepared containing glyphosate ammonium or IPA salt and excipient ingredients as shown in Table 6a. Concentrate composition 6-01 is a water-in-oil-in-water multiple emulsion and was prepared by process (vi), using Span 80 as emulsifier #1. Concentrate compositions 6-02 to 6-11 and 6-17 are oil-in-water emulsions and were prepared by process (vii). Concentrate compositions 6-12 to 6-16 are aqueous solution concentrates and were prepared by process (viii), the component indicated below as "emulsifier #2" being the surfactant component.

TABLE 6a

| Conc. comp. | Glyphosate a.e. | Butyl stearate | Span 80 | Emulsifier #2 | % in inner aq. Phase Water | % in inner aq. Phase Glyphosate | Emulsifier #2 | Glyphosate salt |
|---|---|---|---|---|---|---|---|---|
| 6-01 | 10 | 18.0 | 3.0 | 5.0 | 9.0 | 20 | Tween 20 | IPA |
| 6-02 | 15 | 1.0 |  | 10.0 |  |  | Tween 80 | IPA |
| 6-03 | 15 | 1.0 |  | 10.0 |  |  | Neodol 25-12 | IPA |
| 6-04 | 15 | 1.0 |  | 10.0 |  |  | Neodol 25-20 | IPA |
| 6-05 | 15 | 1.0 |  | 10.0 |  |  | steareth-20 | IPA |
| 6-06 | 15 | 1.0 |  | 10.0 |  |  | oleth-20 | IPA |
| 6-07 | 15 | 1.0 |  | 10.0 |  |  | Tween 80 | ammonium |
| 6-08 | 15 | 1.0 |  | 10.0 |  |  | Neodol 25-12 | ammonium |
| 6-09 | 15 | 1.0 |  | 10.0 |  |  | Neodol 25-20 | ammonium |
| 6-10 | 15 | 1.0 |  | 10.0 |  |  | steareth-20 | ammonium |
| 6-11 | 15 | 1.0 |  | 10.0 |  |  | oleth-20 | ammonium |
| 6-12 | 15 |  |  | 10.0 |  |  | Tween 80 | IPA |
| 6-13 | 15 |  |  | 10.0 |  |  | Neodol 25-12 | IPA |
| 6-14 | 15 |  |  | 10.0 |  |  | Neodol 25-20 | IPA |
| 6-15 | 15 |  |  | 10.0 |  |  | steareth-20 | IPA |
| 6-16 | 15 |  |  | 10.0 |  |  | oleth-20 | IPA |
| 6-17 | 15 | 1.0 |  | 10.0 |  |  | Emerest 2661 | IPA |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 20 days after application.

Formulations B, C and J were applied as comparative treatments. Results, averaged for all replicates of each treatment, are shown in Table 6b.

TABLE 6b

| Concentrate composition | Glyphosate rate g a.e./ha | % Inhibition ABUTH | % Inhibition ECHCF |
|---|---|---|---|
| Formulation B | 150 | 2 | 5 |
|  | 250 | 3 | 25 |
|  | 350 | 28 | 30 |
|  | 450 | 53 | 50 |
| Formulation C | 150 | 5 | 25 |
|  | 250 | 60 | 50 |
|  | 350 | 85 | 83 |
|  | 450 | 88 | 88 |
| Formulation J | 150 | 2 | 10 |
|  | 250 | 70 | 40 |
|  | 350 | 82 | 53 |
|  | 450 | 87 | 83 |
| 6-01 | 150 | 23 | 20 |
|  | 250 | 72 | 30 |
|  | 350 | 80 | 80 |
|  | 450 | 85 | 69 |
| 6-02 | 150 | 5 | 18 |
|  | 250 | 72 | 38 |
|  | 350 | 82 | 63 |
|  | 450 | 85 | 83 |
| 6-03 | 150 | 25 | 20 |
|  | 250 | 70 | 57 |
|  | 350 | 85 | 68 |
|  | 450 | 90 | 83 |
| 6-04 | 150 | 25 | 27 |
|  | 250 | 77 | 67 |
|  | 350 | 85 | 62 |
|  | 450 | 88 | 70 |
| 6-05 | 150 | 60 | 25 |
|  | 250 | 82 | 62 |
|  | 350 | 87 | 73 |
|  | 450 | 85 | 80 |
| 6-06 | 150 | 50 | 32 |
|  | 250 | 78 | 78 |
|  | 350 | 91 | 91 |
|  | 450 | 98 | 98 |
| 6-07 | 150 | 5 | 25 |
|  | 250 | 55 | 77 |
|  | 350 | 77 | 86 |
|  | 450 | 83 | 99 |
| 6-08 | 150 | 0 | 13 |
|  | 250 | 58 | 78 |
|  | 350 | 80 | 85 |
|  | 450 | 85 | 87 |
| 6-09 | 150 | 7 | 25 |
|  | 250 | 57 | 72 |
|  | 350 | 77 | 83 |
|  | 450 | 91 | 92 |
| 6-10 | 150 | 50 | 25 |
|  | 250 | 80 | 55 |
|  | 350 | 86 | 87 |
|  | 450 | 92 | 82 |
| 6-11 | 150 | 53 | 30 |
|  | 250 | 78 | 80 |
|  | 350 | 87 | 89 |
|  | 450 | 95 | 98 |
| 6-12 | 150 | 0 | 25 |
|  | 250 | 50 | 77 |
|  | 350 | 77 | 90 |
|  | 450 | 83 | 94 |
| 6-13 | 150 | 2 | 30 |
|  | 250 | 55 | 75 |
|  | 350 | 72 | 92 |
|  | 450 | 85 | 80 |
| 6-14 | 150 | 12 | 30 |
|  | 250 | 75 | 78 |
|  | 350 | 84 | 90 |
|  | 450 | 96 | 94 |
| 6-15 | 150 | 55 | 35 |
|  | 250 | 78 | 80 |
|  | 350 | 80 | 94 |
|  | 450 | 86 | 98 |
| 6-16 | 150 | 50 | 35 |
|  | 250 | 73 | 63 |
|  | 350 | 84 | 83 |
|  | 450 | 89 | 95 |
| 6-17 | 150 | 0 | 10 |
|  | 250 | 10 | 53 |
|  | 350 | 53 | 83 |
|  | 450 | 62 | 87 |

Compositions containing steareth-20 (6-05, 6-06, 6-10, 6-11, 6-15, 6-16) generally exhibited superior herbicidal effectiveness to counterparts containing Neodol 25-20 (6-04, 6-09, 6-14), at least on ABUTH. The presence of a small amount of butyl stearate tended to enhance effectiveness on ABUTH (compare 6-05 and 6-06 with 6-15 and 6-16).

Example 7

Aqueous concentrate compositions were prepared containing glyphosate IPA salt and excipient ingredients as shown in Table 7a. Concentrate composition 7-01 is a water-in-oil-in-water multiple emulsion and was prepared by process (vi), using Span 80 as emulsifier #1. Concentrate compositions 7-02 to 7-08, 7-14, 7-16 and 7-17 are oil-in-water emulsions and were prepared by process (vii). Concentrate compositions 7-09 to 7-13 and 7-15 are aqueous solution concentrates and were prepared by process (viii), the component indicated below as "emulsifier #2" being the surfactant component.

TABLE 7a

| Conc. comp. | Glyphosate a.e. | Butyl stearate | Span 80 | Emulsifier #2 | % in inner aq. phase Water | Glyphosate | Emulsifier #2 |
|---|---|---|---|---|---|---|---|
| 7-01 | 10 | 18.0 | 3.0 | 2.5 | 9.0 | 20 | Tween 20 |
| 7-02 | 15 | 1.0 | | 10.0 | | | Emerest 2661 |
| 7-03 | 15 | 1.0 | | 10.0 | | | Tween 80 |
| 7-04 | 15 | 1.0 | | 10.0 | | | oleth-20 |
| 7-05 | 15 | 1.0 | | 10.0 | | | Neodol 25-20 |
| 7-06 | 15 | 1.0 | | 10.0 | | | ceteareth-27 |
| 7-07 | 15 | 1.0 | | 10.0 | | | ceteareth-55 |
| 7-08 | 15 | 1.0 | | 10.0 | | | Genapol UD-110 |
| 7-09 | 15 | | | 10.0 | | | ceteareth-27 |
| 7-10 | 15 | | | 10.0 | | | ceteareth-55 |
| 7-11 | 15 | | | 10.0 | | | Genapol UD-110 |
| 7-12 | 15 | | | 10.0 | | | oleth-20 |
| 7-13 | 10 | | | 10.0 | | | oleth-20 |
| 7-14 | 10 | 1.0 | | 10.0 | | | oleth-20 |
| 7-15 | 20 | | | 10.0 | | | oleth-20 |
| 7-16 | 15 | 0.5 | | 5.0 | | | oleth-20 |
| 7-17 | 15 | 0.5 | | 10.0 | | | oleth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 18 days after application.

Formulations B, C and J were applied as comparative treatments. Results, averaged for all replicates of each treatment, are shown in Table 7b.

TABLE 7b

| Concentrate composition | Glyphosate rate g a.e./ha | % Inhibition ABUTH | % Inhibition ECHCF |
|---|---|---|---|
| Formulation B | 150 | 0 | 0 |
| | 250 | 8 | 20 |
| | 350 | 27 | 40 |
| | 450 | 62 | 50 |
| Formulation C | 150 | 27 | 50 |
| | 250 | 75 | 70 |
| | 350 | 92 | 80 |
| | 450 | 97 | 92 |
| Formulation J | 150 | 23 | 30 |
| | 250 | 72 | 50 |
| | 350 | 94 | 63 |
| | 450 | 95 | 80 |
| 7-01 | 150 | 22 | 30 |
| | 250 | 60 | 40 |
| | 350 | 83 | 57 |
| | 450 | 90 | 67 |
| 7-02 | 150 | 12 | 33 |
| | 250 | 45 | 50 |
| | 350 | 73 | 63 |
| | 450 | 83 | 83 |
| 7-03 | 150 | 27 | 43 |
| | 250 | 68 | 50 |
| | 350 | 80 | 63 |
| | 450 | 87 | 87 |
| 7-04 | 150 | 68 | 47 |
| | 250 | 95 | 73 |
| | 350 | 99 | 78 |
| | 450 | 95 | 90 |
| 7-05 | 150 | 50 | 50 |
| | 250 | 77 | 77 |
| | 350 | 90 | 83 |
| | 450 | 98 | 83 |

TABLE 7b-continued

| Concentrate composition | Glyphosate rate g a.e./ha | % Inhibition ABUTH | % Inhibition ECHCF |
|---|---|---|---|
| 7-06 | 150 | 78 | 67 |
| | 250 | 93 | 82 |
| | 350 | 97 | 87 |
| | 450 | 99 | 97 |
| 7-07 | 150 | 87 | 57 |
| | 250 | 96 | 73 |
| | 350 | 99 | 85 |
| | 450 | 99 | 97 |
| 7-08 | 150 | 42 | 30 |
| | 250 | 73 | 53 |
| | 350 | 82 | 85 |
| | 450 | 95 | 89 |
| 7-09 | 150 | 67 | 40 |
| | 250 | 95 | 73 |
| | 350 | 99 | 95 |
| | 450 | 99 | 98 |
| 7-10 | 150 | 85 | 60 |
| | 250 | 96 | 68 |
| | 350 | 96 | 91 |
| | 450 | 100 | 88 |
| 7-11 | 150 | 13 | 10 |
| | 250 | 67 | 50 |
| | 350 | 78 | 60 |
| | 450 | 88 | 73 |
| 7-12 | 150 | 72 | 43 |
| | 250 | 97 | 68 |
| | 350 | 98 | 83 |
| | 450 | 99 | 93 |
| 7-13 | 150 | 73 | 57 |
| | 250 | 88 | 70 |
| | 350 | 98 | 87 |
| | 450 | 99 | 96 |
| 7-14 | 150 | 80 | 50 |
| | 250 | 96 | 70 |
| | 350 | 99 | 85 |
| | 450 | 98 | 88 |
| 7-15 | 150 | 70 | 43 |
| | 250 | 96 | 53 |
| | 350 | 97 | 82 |
| | 450 | 99 | 89 |
| 7-16 | 150 | 62 | 53 |
| | 250 | 88 | 72 |
| | 350 | 99 | 81 |
| | 450 | 99 | 91 |
| 7-17 | 150 | 72 | 58 |
| | 250 | 95 | 68 |

TABLE 7b-continued

| Concentrate composition | Glyphosate rate g a.e./ha | % Inhibition ABUTH | % Inhibition ECHCF |
|---|---|---|---|
| | 350 | 100 | 89 |
| | 450 | 100 | 93 |

The greatest herbicidal effectiveness in this test was exhibited by compositions containing a $C_{16-18}$ alkylether surfactant (oleth-20, ceteareth-27 or ceteareth-55).

Example 8

Aqueous concentrate compositions were prepared containing glyphosate IPA salt and excipient ingredients as shown in Table 8a. All are oil-in-water emulsions and were prepared by process (vii).

TABLE 8a

| Concentrate composition | Glyphosate g a.e./l | Butyl stearate % w/w | Surfactant % w/w | Type of surfactant |
|---|---|---|---|---|
| 8-01 | 163 | 1.00 | 10.0 | Tween 80 |
| 8-02 | 163 | 1.00 | 10.0 | Emerest 2661 |
| 8-03 | 326 | 1.00 | 10.0 | Genapol UD-110 |
| 8-04 | 326 | 0.50 | 10.0 | Genapol UD-110 |
| 8-05 | 326 | 0.25 | 10.0 | Genapol UD-110 |
| 8-06 | 163 | 0.25 | 10.0 | Genapol UD-110 |
| 8-07 | 163 | 1.00 | 10.0 | Genapol UD-110 |
| 8-08 | 163 | 1.00 | 10.0 | Neodol 1-9 |
| 8-09 | 163 | 1.00 | 10.0 | Neodol 1-12 |
| 8-10 | 163 | 1.00 | 10.0 | Neodol 25-20 |
| 8-11 | 163 | 1.00 | 10.0 | Neodol 25-12 |
| 8-12 | 163 | 1.00 | 10.0 | Neodox 25-11 |
| 8-13 | 163 | 1.00 | 10.0 | laureth-23 |
| 8-14 | 163 | 1.00 | 10.0 | ceteth-20 |
| 8-15 | 163 | 1.00 | 10.0 | steareth-20 |
| 8-16 | 163 | 1.00 | 10.0 | oleth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 15 days after planting ABUTH and ECHCF, and evaluation of herbicidal inhibition was done 23 days after application.

Formulations B, C and J were applied as comparative treatments. Results, averaged for all replicates of each treatment are shown in Table 8b.

TABLE 8b

| Concentrate composition | Glyphosate rate g a.e./ha | % Inhibition ABUTH | % Inhibition ECHCF |
|---|---|---|---|
| Formulation B | 150 | 0 | 0 |
| | 250 | 25 | 22 |
| | 350 | 60 | 40 |
| | 450 | 65 | 52 |
| Formulation C | 150 | 43 | 52 |
| | 250 | 72 | 83 |
| | 350 | 87 | 98 |
| | 450 | 97 | 95 |
| Formulation J | 150 | 50 | 43 |
| | 250 | 75 | 91 |
| | 350 | 86 | 96 |
| | 450 | 95 | 97 |
| 8-01 | 150 | 50 | 30 |
| | 250 | 75 | 75 |
| | 350 | 85 | 87 |
| | 450 | 90 | 92 |
| 8-02 | 150 | 35 | 47 |
| | 250 | 58 | 77 |
| | 350 | 75 | 85 |
| | 450 | 80 | 96 |
| 8-03 | 150 | 33 | 32 |
| | 250 | 57 | 53 |
| | 350 | 75 | 78 |
| | 450 | 84 | 94 |
| 8-04 | 150 | 20 | 25 |
| | 250 | 55 | 68 |
| | 350 | 78 | 91 |
| | 450 | 82 | 97 |
| 8-05 | 150 | 37 | 12 |
| | 250 | 58 | 42 |
| | 350 | 81 | 70 |
| | 450 | 86 | 73 |
| 8-06 | 150 | 50 | 8 |
| | 250 | 65 | 40 |
| | 350 | 81 | 65 |
| | 450 | 92 | 85 |
| 8-07 | 150 | 50 | 30 |
| | 250 | 63 | 48 |
| | 350 | 84 | 68 |
| | 450 | 98 | 84 |
| 8-08 | 150 | 43 | 35 |
| | 250 | 52 | 65 |
| | 350 | 73 | 85 |
| | 450 | 84 | 85 |
| 8-09 | 150 | 55 | 40 |
| | 250 | 68 | 58 |
| | 350 | 79 | 65 |
| | 450 | 97 | 73 |
| 8-10 | 150 | 69 | 40 |
| | 250 | 81 | 68 |
| | 350 | 94 | 92 |
| | 450 | 99 | 96 |
| 8-11 | 150 | 58 | 50 |
| | 250 | 84 | 60 |
| | 350 | 90 | 83 |
| | 450 | 94 | 93 |
| 8-12 | 150 | 50 | 40 |
| | 250 | 57 | 67 |
| | 350 | 65 | 84 |
| | 450 | 75 | 98 |
| 8-13 | 150 | 57 | 53 |
| | 250 | 78 | 73 |
| | 350 | 89 | 97 |
| | 450 | 98 | 97 |
| 8-14 | 150 | 68 | 67 |
| | 250 | 85 | 73 |
| | 350 | 97 | 98 |
| | 450 | 100 | 97 |
| 8-15 | 150 | 72 | 50 |
| | 250 | 88 | 89 |
| | 350 | 89 | 98 |
| | 450 | 99 | 97 |
| 8-16 | 150 | 65 | 53 |
| | 250 | 87 | 72 |
| | 350 | 97 | 85 |
| | 450 | 100 | 95 |

Activity overall in this test was very high, and differences among compositions in herbicidal effectivess are difficult to discern clearly.

Example 9

Aqueous concentrate compositions were prepared containing glyphosate IPA salt and excipient ingredients as shown in Table 9a. All are oil-in-water emulsions and were prepared by process (vii).

TABLE 9a

| Concentrate composition | Glyphosate g a.e./l | Butyl stearate % w/w | Surfactant % w/w | Type of surfactant |
|---|---|---|---|---|
| 9-01 | 163 | 1.00 | 10.0 | Tween 80 |
| 9-02 | 163 | 1.00 | 10.0 | Emerest 2661 |
| 9-03 | 163 | 1.00 | 10.0 | Neodol 25-20 |
| 9-04 | 163 | 1.00 | 10.0 | oleth-20 |
| 9-05 | 163 | 0.50 | 10.0 | oleth-20 |
| 9-06 | 163 | 0.25 | 5.0 | oleth-20 |
| 9-07 | 163 | 0.50 | 2.5 | oleth-20 |
| 9-08 | 163 | 0.50 | 2.5 | oleth-20 |
| 9-09 | 163 | 0.25 | 1.0 | oleth-20 |
| 9-10 | 326 | 1.00 | 5.0 | Neodol 1-12 |
| 9-11 | 326 | 0.50 | 10.0 | Neodol 1-12 |
| 9-12 | 326 | 0.25 | 10.0 | Neodol 1-12 |
| 9-13 | 326 | 1.00 | 10.0 | Neodol 1-12 |
| 9-14 | 326 | 0.50 | 5.0 | Neodol 1-12 |
| 9-15 | 326 | 0.25 | 5.0 | Neodol 1-12 |
| 9-16 | 326 | 0.10 | 5.0 | Neodol 1-12 |

Velvetleaf (*Abutilon theophrasti*, ABUTH) and Japanese millet (*Echinochloa crus-galli*, ECHCF) plants were grown and treated by the standard procedures given above. Applications of spray compositions were made 15 days after planting ABUTH and ECHCF, and evaluation of herbicidal inhibition was done 20 days after application.

Formulations B, C and J were applied as comparative treatments. Results, averaged for all replicates of each treatment, are shown in Table 9b.

TABLE 9b

| Concentrate composition | Glyphosate rate g a.e./ha | % Inhibition ABUTH | % Inhibition ECHCF |
|---|---|---|---|
| Formulation B | 150 | 7 | 50 |
|  | 250 | 45 | 60 |
|  | 350 | 73 | 73 |
|  | 450 | 80 | 78 |
| Formulation C | 150 | 75 | 77 |
|  | 250 | 87 | 100 |
|  | 350 | 96 | 99 |
|  | 450 | 99 | 97 |
| Formulation J | 150 | 72 | 77 |
|  | 250 | 83 | 89 |
|  | 350 | 97 | 99 |
|  | 450 | 97 | 98 |
| 9-01 | 150 | 60 | 75 |
|  | 250 | 80 | 85 |
|  | 350 | 93 | 97 |
|  | 450 | 98 | 98 |
| 9-02 | 150 | 57 | 75 |
|  | 250 | 70 | 83 |
|  | 350 | 87 | 83 |
|  | 450 | 90 | 94 |
| 9-03 | 150 | 77 | 80 |
|  | 250 | 87 | 92 |
|  | 350 | 97 | 87 |
|  | 450 | 99 | 98 |
| 9-04 | 150 | 80 | 89 |
|  | 250 | 93 | 92 |
|  | 350 | 99 | 99 |
|  | 450 | 100 | 99 |
| 9-05 | 150 | 83 | 83 |
|  | 250 | 92 | 93 |
|  | 350 | 97 | 90 |
|  | 450 | 100 | 93 |

TABLE 9b-continued

| Concentrate composition | Glyphosate rate g a.e./ha | % Inhibition ABUTH | % Inhibition ECHCF |
|---|---|---|---|
| 9-06 | 150 | 77 | 77 |
|  | 250 | 80 | 91 |
|  | 350 | 90 | 99 |
|  | 450 | 98 | 99 |
| 9-07 | 150 | 77 | 83 |
|  | 250 | 82 | 89 |
|  | 350 | 90 | 91 |
|  | 450 | 97 | 98 |
| 9-08 | 150 | 47 | 82 |
|  | 250 | 73 | 82 |
|  | 350 | 80 | 97 |
|  | 450 | 92 | 91 |
| 9-09 | 150 | 73 | 78 |
|  | 250 | 87 | 88 |
|  | 350 | 97 | 94 |
|  | 450 | 99 | 99 |
| 9-10 | 150 | 52 | 67 |
|  | 250 | 70 | 80 |
|  | 350 | 93 | 88 |
|  | 450 | 93 | 94 |
| 9-11 | 150 | 40 | 68 |
|  | 250 | 72 | 85 |
|  | 350 | 87 | 96 |
|  | 450 | 93 | 96 |
| 9-12 | 150 | 37 | 60 |
|  | 250 | 68 | 83 |
|  | 350 | 85 | 85 |
|  | 450 | 93 | 75 |
| 9-13 | 150 | 28 | 63 |
|  | 250 | 53 | 80 |
|  | 350 | 85 | 97 |
|  | 450 | 88 | 97 |
| 9-14 | 150 | 37 | 63 |
|  | 250 | 58 | 73 |
|  | 350 | 83 | 96 |
|  | 450 | 90 | 91 |
| 9-15 | 150 | 30 | 70 |
|  | 250 | 47 | 83 |
|  | 350 | 82 | 89 |
|  | 450 | 87 | 89 |
| 9-16 | 150 | 40 | 53 |
|  | 250 | 53 | 82 |
|  | 350 | 80 | 80 |
|  | 450 | 88 | 77 |

Composition 9-04, containing 1% butyl stearate and 10% oleth-20 (surfactant to glyphosate a.e. weight/weight ratio about 1:1.5), exhibited marginally greater herbicidal effectiveness than composition 9-03, containing 1% butyl stearate and 10% oleth-20. At this very high surfactant to glyphosate ratio, however, both performed extremely well. Surprisingly, when the butyl stearate and oleth-20 concentrations were significantly lowered, this high level of performance was maintained to a remarkable degree. Even when butyl stearate was reduced to 0.25% and oleth-20 to 2.5% (surfactant to glyphosate a.e. ratio about 1:6), as in composition 9-06, herbicidal effectiveness was still similar to that obtained with commercial standard Formulations C and J.

Example 10

Aqueous concentrate compositions were prepared containing glyphosate IPA salt and excipient ingredients as shown in Table 10a. Concentrate compositions 10-01 to 10-08 and 10-11 to 10-16 are oil-in-water emulsions and were prepared by process (vii). Concentrate compositions 10-09 and 10-10 are aqueous solution concentrates and were prepared by process (viii).

TABLE 10a

| Concentrate composition | Glyphosate a.e. | Butyl stearate | Surfactant | Type of surfactant |
|---|---|---|---|---|
| | % w/w | | | |
| 10-01 | 15.0 | 0.25 | 5.0 | Emerest 2661 |
| 10-02 | 15.0 | 0.25 | 5.0 | Tween 80 |
| 10-03 | 15.0 | 0.25 | 5.0 | Neodol 25-20 |
| 10-04 | 15.0 | 0.25 | 5.0 | laureth-23 |
| 10-05 | 15.0 | 0.25 | 5.0 | ceteth-20 |
| 10-06 | 15.0 | 0.25 | 2.5 | Tween 80 |
| 10-07 | 15.0 | 0.10 | 1.0 | Tween 80 |
| 10-08 | 15.0 | 1.00 | 10.0 | Tween 80 |
| 10-09 | 15.0 | | 5.0 | laureth-23 |
| 10-10 | 15.0 | | 5.0 | ceteth-20 |
| 10-11 | 15.0 | 1.00 | 10.0 | Neodol 25-20 |
| 10-12 | 15.0 | 1.00 | 10.0 | oleth-20 |
| 10-13 | 15.0 | 0.50 | 5.0 | oleth-20 |
| 10-14 | 15.0 | 0.25 | 5.0 | oleth-20 |
| 10-15 | 15.0 | 0.25 | 2.5 | oleth-20 |
| 10-16 | 15.0 | 0.25 | 5.0 | Genapol UD-110 |

Velvetleaf (*Abutilon theophrasti*, ABUTH) and Japanese millet (*Echinochloa crus-galli*, ECHCF) plants were grown and treated by the standard procedures given above. Applications of spray compositions were made 12 days after planting ABUTH and ECHCF, and evaluation of herbicidal inhibition was done 16 days after application.

Formulations B, C and J were applied as comparative treatments. Results, averaged for all replicates of each treatment, are shown in Table 10b.

TABLE 10b

| Concentrate composition | Glyphosate rate g a.e./ha | % Inhibition ABUTH | ECHCF |
|---|---|---|---|
| Formulation B | 150 | 2 | 10 |
| | 250 | 5 | 20 |
| | 350 | 43 | 30 |
| | 450 | 58 | 43 |
| Formulation C | 150 | 68 | 50 |
| | 250 | 92 | 79 |
| | 350 | 96 | 90 |
| | 450 | 98 | 85 |
| Formulation J | 150 | 57 | 43 |
| | 250 | 90 | 63 |
| | 350 | 95 | 80 |
| | 450 | 95 | 95 |
| 10-01 | 150 | 7 | 33 |
| | 250 | 50 | 43 |
| | 350 | 77 | 53 |
| | 450 | 80 | 93 |
| 10-02 | 150 | 17 | 50 |
| | 250 | 72 | 70 |
| | 350 | 80 | 80 |
| | 450 | 80 | 93 |
| 10-03 | 150 | 43 | 40 |
| | 250 | 75 | 68 |
| | 350 | 87 | 75 |
| | 450 | 96 | 95 |
| 10-04 | 150 | 33 | 47 |
| | 250 | 73 | 63 |
| | 350 | 80 | 77 |
| | 450 | 90 | 93 |
| 10-05 | 150 | 73 | 37 |
| | 250 | 92 | 57 |
| | 350 | 95 | 88 |
| | 450 | 95 | 73 |
| 10-06 | 150 | 25 | 35 |
| | 250 | 68 | 47 |
| | 350 | 80 | 92 |
| | 450 | 88 | 85 |
| 10-07 | 150 | 3 | 30 |
| | 250 | 57 | 40 |
| | 350 | 77 | 53 |
| | 450 | 80 | 67 |
| 10-08 | 150 | 53 | 43 |
| | 250 | 77 | 62 |
| | 350 | 80 | 88 |
| | 450 | 93 | 80 |
| 10-09 | 150 | 32 | 60 |
| | 250 | 77 | 53 |
| | 350 | 93 | 73 |
| | 450 | 97 | 93 |
| 10-10 | 150 | 75 | 35 |
| | 250 | 92 | 77 |
| | 350 | 96 | 77 |
| | 450 | 97 | 93 |
| 10-11 | 150 | 75 | 53 |
| | 250 | 90 | 78 |
| | 350 | 95 | 89 |
| | 450 | 98 | 97 |
| 10-12 | 150 | 80 | 43 |
| | 250 | 95 | 73 |
| | 350 | 96 | 92 |
| | 450 | 98 | 89 |
| 10-13 | 150 | 75 | 53 |
| | 250 | 92 | 97 |
| | 350 | 97 | 99 |
| | 450 | 96 | 93 |
| 10-14 | 150 | 78 | 70 |
| | 250 | 90 | 92 |
| | 350 | 93 | 97 |
| | 450 | 95 | 93 |
| 10-15 | 150 | 70 | 60 |
| | 250 | 83 | 98 |
| | 350 | 95 | 99 |
| | 450 | 97 | 99 |
| 10-16 | 150 | 27 | 52 |
| | 250 | 75 | 73 |
| | 350 | 80 | 98 |
| | 450 | 83 | 99 |

Extremely high herbicidal effectiveness was again observed with a composition (10-15) containing 15% glyphosate a.e. and just 2.5% oleth-20 together with 0.25% butyl stearate. A comparison of 15% glyphosate a.e. compositions containing 5% alkylether surfactant and 0.25% butyl stearate provided the following ranking of alkylethers in descending order of effectiveness: oleth-20 (10-14) >ceteth-20 (10-05)>Neodol 25-20 (10-03)=laureth-23 (10-04).

Example 11

Aqueous concentrate compositions were prepared containing glyphosate IPA salt and excipient ingredients as shown in Table 11a. All are oil-in-water emulsions and were prepared by process (vii).

TABLE 11a

| Concentrate composition | Glyphosate g a.e./l | % w/w Butyl stearate | Surfactant | Type of surfactant |
|---|---|---|---|---|
| 11-01 | 163 | 0.50 | 5.0 | oleth-20 |
| 11-02 | 163 | 0.25 | 5.0 | oleth-20 |
| 11-03 | 163 | 0.25 | 2.5 | oleth-20 |

TABLE 11a-continued

| Concentrate composition | Glyphosate g a.e./l | % w/w Butyl stearate | % w/w Surfactant | Type of surfactant |
|---|---|---|---|---|
| 11-04 | 163 | 1.00 | 10.0 | oleth-20 |
| 11-05 | 163 | 0.50 | 5.0 | steareth-20 |
| 11-06 | 163 | 0.25 | 5.0 | steareth-20 |
| 11-07 | 163 | 0.25 | 2.5 | steareth-20 |
| 11-08 | 163 | 1.00 | 10.0 | steareth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and ECHCF, and evaluation of herbicidal inhibition was done 16 days after application.

Formulations B, C and J were applied as comparative treatments. Results, averaged for all replicates of each treatment, are shown in Table 11b.

TABLE 11b

| Concentrate composition | Glyphosate rate g a.e./ha | % Inhibition ABUTH | % Inhibition ECHCF |
|---|---|---|---|
| Formulation B | 150 | 0 | 30 |
|  | 250 | 20 | 43 |
|  | 350 | 43 | 53 |
|  | 450 | 68 | 57 |
| Formulation C | 150 | 60 | 47 |
|  | 250 | 75 | 53 |
|  | 350 | 87 | 80 |
|  | 450 | 87 | 78 |
| Formulation J | 150 | 42 | 43 |
|  | 250 | 83 | 60 |
|  | 350 | 87 | 73 |
|  | 450 | 93 | 87 |
| 11-01 | 150 | 60 | 60 |
|  | 250 | 78 | 63 |
|  | 350 | 87 | 89 |
|  | 450 | 92 | 78 |
| 11-02 | 150 | 70 | 43 |
|  | 250 | 80 | 91 |
|  | 350 | 87 | 86 |
|  | 450 | 96 | 87 |
| 11-03 | 150 | 52 | 43 |
|  | 250 | 75 | 72 |
|  | 350 | 83 | 93 |
|  | 450 | 87 | 94 |
| 11-04 | 150 | 72 | 50 |
|  | 250 | 93 | 73 |
|  | 350 | 97 | 95 |
|  | 450 | 97 | 91 |
| 11-05 | 150 | 72 | 43 |
|  | 250 | 80 | 78 |
|  | 350 | 87 | 91 |
|  | 450 | 93 | 85 |
| 11-06 | 150 | 68 | 40 |
|  | 250 | 80 | 50 |
|  | 350 | 93 | 75 |
|  | 450 | 95 | 85 |
| 11-07 | 150 | 63 | 37 |
|  | 250 | 78 | 55 |
|  | 350 | 87 | 84 |
|  | 450 | 83 | 82 |
| 11-08 | 150 | 70 | 50 |
|  | 250 | 80 | 70 |
|  | 350 | 92 | 84 |
|  | 450 | 94 | 98 |

All compositions containing butyl stearate and either oleth-20 or steareth-20 showed a very high level of performance by comparison with commercial standard Formulations C and J.

Example 12

Aqueous concentrate compositions were prepared containing glyphosate IPA salt and excipient ingredients as shown in Table 12a. All are oil-in-water emulsions and were prepared by process (vii).

TABLE 12a

| Concentrate composition | Glyphosate g a.e./l | % w/w Butyl stearate | % w/w Surfactant | Type of surfactant |
|---|---|---|---|---|
| 12-01 | 163 | 0.50 | 5.0 | oleth-20 |
| 12-02 | 163 | 0.25 | 5.0 | oleth-20 |
| 12-03 | 163 | 0.25 | 2.5 | oleth-20 |
| 12-04 | 163 | 1.00 | 10.0 | oleth-20 |
| 12-05 | 163 | 0.50 | 5.0 | steareth-20 |
| 12-06 | 163 | 0.25 | 5.0 | steareth-20 |
| 12-07 | 163 | 0.25 | 2.5 | steareth-20 |
| 12-08 | 163 | 1.00 | 10.0 | steareth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 18 days after application.

Formulations B, C and J were applied as comparative treatments. Results, averaged for all replicates of each treatment, are shown in Table 12b.

TABLE 12b

| Concentrate composition | Glyphosate rate g a.e./ha | % Inhibition ABUTH | % Inhibition ECHCF |
|---|---|---|---|
| Formulation B | 150 | 3 | 10 |
|  | 250 | 28 | 23 |
|  | 350 | 72 | 37 |
|  | 450 | 73 | 50 |
| Formulation C | 150 | 57 | 43 |
|  | 250 | 87 | 62 |
|  | 350 | 93 | 83 |
|  | 450 | 99 | 95 |
| Formulation J | 150 | 27 | 47 |
|  | 250 | 70 | 53 |
|  | 350 | 92 | 75 |
|  | 450 | 94 | 92 |
| 12-01 | 150 | 68 | 50 |
|  | 250 | 85 | 47 |
|  | 350 | 97 | 70 |
|  | 450 | 99 | 83 |
| 12-02 | 150 | 67 | 40 |
|  | 250 | 78 | 50 |
|  | 350 | 96 | 63 |
|  | 450 | 99 | 68 |
| 12-03 | 150 | 52 | 40 |
|  | 250 | 72 | 50 |
|  | 350 | 95 | 63 |
|  | 450 | 97 | 85 |
| 12-04 | 150 | 72 | 40 |
|  | 250 | 97 | 53 |
|  | 350 | 97 | 77 |
|  | 450 | 99 | 90 |
| 12-05 | 150 | 75 | 40 |
|  | 250 | 0 | 53 |
|  | 350 | 88 | 53 |
|  | 450 | 96 | 78 |
| 12-06 | 150 | 98 | 40 |
|  | 250 | 93 | 50 |
|  | 350 | 97 | 68 |
|  | 450 | 97 | 82 |
| 12-07 | 150 | 73 | 40 |

TABLE 12b-continued

| Concentrate composition | Glyphosate rate g a.e./ha | % Inhibition ABUTH | ECHCF |
|---|---|---|---|
|  | 250 | 92 | 50 |
|  | 350 | 98 | 63 |
|  | 450 | 98 | 80 |
| 12-08 | 150 | 77 | 43 |
|  | 250 | 93 | 57 |
|  | 350 | 97 | 77 |
|  | 450 | 98 | 88 |

All compositions containing butyl stearate and either oleth-20 or steareth-20 showed a very high level of performance by comparison with commercial standard Formulations C and J.

Example 13

Aqueous concentrate compositions were prepared containing glyphosate IPA salt and excipient ingredients as shown in Table 13a. All contain colloidal particulates and were prepared by process (ix).

All compositions of this example showed acceptable storage stability. The compositions containing oleth-20 were not acceptably storage-stable in the absence of the colloidal particulate.

TABLE 13a

| Concentrate composition | Glyphosate g a.e./l | Butyl stearate | Oleth-20 | Aerosil | Type of Aerosil |
|---|---|---|---|---|---|
| 13-01 | 488 | 3.0 |  | 0.4 | OX-50 |
| 13-02 | 488 | 3.0 |  | 0.8 | OX-50 |
| 13-03 | 488 | 3.0 |  | 1.5 | OX-50 |
| 13-04 | 488 |  |  | 0.4 | OX-50 |
| 13-05 | 488 |  |  | 0.8 | OX-50 |
| 13-06 | 488 |  |  | 1.5 | OX-50 |
| 13-07 | 488 | 3.0 |  | 0.4 | MOX-80 |
| 13-08 | 488 | 3.0 |  | 0.8 | MOX-80 |
| 13-09 | 488 | 3.0 |  | 1.5 | MOX-80 |
| 13-10 | 488 |  |  | 0.4 | MOX-80 |
| 13-11 | 488 |  |  | 0.8 | MOX-80 |
| 13-12 | 488 |  |  | 1.5 | MOX-80 |
| 13-13 | 488 | 3.0 |  | 0.4 | MOX-170 |
| 13-14 | 488 | 3.0 |  | 0.8 | MOX-170 |
| 13-15 | 488 | 3.0 |  | 1.5 | MOX-170 |
| 13-16 | 488 |  |  | 0.4 | MOX-170 |
| 13-17 | 488 |  |  | 0.8 | MOX-170 |
| 13-18 | 488 |  |  | 1.5 | MOX-170 |
| 13-19 | 488 | 3.0 | 3.0 | 1.5 | MOX-80 |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and ECHCF, and evaluation of herbicidal inhibition was done 20 days after application.

Formulations B and J were applied as comparative treatments. Results, averaged for all replicates of each treatment, are shown in Table 13b.

TABLE 13b

| Concentrate composition | Glyphosate rate g a.e./ha | % Inhibition ABUTH | ECHCF |
|---|---|---|---|
| Formulation B | 150 | 0 | 27 |
|  | 250 | 17 | 37 |
|  | 350 | 47 | 57 |
|  | 450 | 60 | 60 |
| Formulation J | 150 | 57 | 50 |
|  | 250 | 82 | 87 |
|  | 350 | 95 | 99 |
|  | 450 | 98 | 99 |
| 13-01 | 150 | 37 | 60 |
|  | 250 | 73 | 70 |
|  | 350 | 96 | 97 |
|  | 450 | 96 | 99 |
| 13-02 | 150 | 43 | 50 |
|  | 250 | 73 | 63 |
|  | 350 | 93 | 96 |
|  | 450 | 98 | 99 |
| 13-03 | 150 | 53 | 60 |
|  | 250 | 83 | 87 |
|  | 350 | 87 | 97 |
|  | 450 | 98 | 98 |
| 13-04 | 150 | 45 | 40 |
|  | 250 | 57 | 60 |
|  | 350 | 78 | 95 |
|  | 450 | 94 | 100 |
| 13-05 | 150 | 47 | 50 |
|  | 250 | 60 | 82 |
|  | 350 | 92 | 96 |
|  | 450 | 95 | 99 |
| 13-06 | 150 | 38 | 53 |
|  | 250 | 68 | 96 |
|  | 350 | 82 | 99 |
|  | 450 | 83 | 95 |
| 13-07 | 150 | 50 | 57 |
|  | 250 | 87 | 88 |
|  | 350 | 91 | 99 |
|  | 450 | 98 | 98 |
| 13-08 | 150 | 53 | 50 |
|  | 250 | 88 | 85 |
|  | 350 | 96 | 97 |
|  | 450 | 97 | 100 |
| 13-09 | 150 | 40 | 30 |
|  | 250 | 37 | 47 |
|  | 350 | 57 | 80 |
|  | 450 | 77 | 94 |
| 13-10 | 150 | 47 | 50 |
|  | 250 | 70 | 95 |
|  | 350 | 75 | 99 |
|  | 450 | 77 | 98 |
| 13-11 | 150 | 27 | 60 |
|  | 250 | 72 | 85 |
|  | 350 | 82 | 98 |
|  | 450 | 75 | 99 |
| 13-12 | 150 | 37 | 57 |
|  | 250 | 73 | 86 |
|  | 350 | 80 | 99 |
|  | 450 | 85 | 100 |
| 13-13 | 150 | 45 | 53 |
|  | 250 | 85 | 94 |
|  | 350 | 95 | 100 |
|  | 450 | 98 | 99 |
| 13-14 | 150 | 50 | 50 |
|  | 250 | 78 | 83 |
|  | 350 | 94 | 98 |
|  | 450 | 98 | 99 |
| 13-15 | 150 | 53 | 67 |
|  | 250 | 75 | 88 |
|  | 350 | 93 | 97 |
|  | 450 | 96 | 99 |
| 13-16 | 150 | 42 | 50 |
|  | 250 | 47 | 96 |
|  | 350 | 70 | 98 |
|  | 450 | 90 | 99 |

TABLE 13b-continued

| Concentrate composition | Glyphosate rate g a.e./ha | % Inhibition ABUTH | ECHCF |
|---|---|---|---|
| 13-17 | 150 | 27 | 83 |
|  | 250 | 57 | 98 |
|  | 350 | 87 | 99 |
|  | 450 | 87 | 100 |
| 13-18 | 150 | 33 | 60 |
|  | 250 | 47 | 94 |
|  | 350 | 83 | 99 |
|  | 450 | 93 | 99 |
| 13-19 | 150 | 45 | 47 |
|  | 250 | 80 | 73 |
|  | 350 | 96 | 94 |
|  | 450 | 99 | 98 |

Remarkably high levels of herbicidal effectiveness were obtained in this test with compositions containing oleth-20 at a weight/weight ratio to glyphosate a.e. of about 1:14, and stabilized with colloidal particulates. In some cases the colloidal particulate alone contributed a major part of the efficacy enhancement. Results with composition 13-09 are out of line with other data and an application problem is suspected.

Example 14

Aqueous concentrate compositions were prepared containing glyphosate IPA salt and excipient ingredients as shown in Table 14a. Concentrate compositions 14-01 to 14-04, 14-06, 14-08, 14-09, 14-11, 14-12, 14-14 and 14-16 are oil-in-water emulsions and were prepared by process (vii). Concentrate compositions 14-05, 14-07, 14-10, 14-13, 14-15 and 14-17 are aqueous solution concentrates and were prepared by process (viii).

TABLE 14a

| Concentrate composition | Glyphosate g a.e./l | % w/w Butyl stearate | Surfactant | Type of surfactant |
|---|---|---|---|---|
| 14-01 | 163 | 0.25 | 2.5 | Neodol 1-12 |
| 14-02 | 163 | 0.25 | 2.5 | laureth-23 |
| 14-03 | 163 | 0.25 | 2.5 | steareth-10 |
| 14-04 | 163 | 0.25 | 2.5 | steareth-20 |
| 14-05 | 163 |  | 2.5 | steareth-20 |
| 14-06 | 163 | 0.25 | 2.5 | steareth-100 |
| 14-07 | 163 |  | 2.5 | steareth-100 |
| 14-08 | 163 | 0.25 | 2.5 | oleth-10 |
| 14-09 | 163 | 0.25 | 2.5 | oleth-20 |
| 14-10 | 163 |  | 2.5 | oleth-20 |
| 14-11 | 163 | 0.25 | 2.5 | ceteth-10 |
| 14-12 | 163 | 0.25 | 2.5 | ceteth-20 |
| 14-13 | 163 |  | 2.5 | ceteth-20 |
| 14-14 | 326 | 0.50 | 5.0 | ceteareth-27 |
| 14-15 | 326 |  | 5.0 | ceteareth-27 |
| 14-16 | 163 | 0.25 | 2.5 | ceteareth-55 |
| 14-17 | 163 |  | 2.5 | ceteareth-55 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 15 days after application.

Formulations B, C and J were applied as comparative treatments. Results, averaged for all replicates of each treatment, are shown in Table 14b.

TABLE 14b

| Concentrate composition | Glyphosate rate g a.e./ha | % Inhibition ABUTH | ECHCF |
|---|---|---|---|
| Formulation B | 150 | 0 | 33 |
|  | 250 | 20 | 43 |
|  | 350 | 63 | 63 |
|  | 450 | 75 | 70 |
| Formulation C | 150 | 53 | 55 |
|  | 250 | 80 | 87 |
|  | 350 | 94 | 97 |
|  | 450 | 98 | 99 |
| Formulation J | 150 | 40 | 57 |
|  | 250 | 80 | 90 |
|  | 350 | 96 | 99 |
|  | 450 | 98 | 99 |
| 14-01 | 150 | 52 | 40 |
|  | 250 | 65 | 73 |
|  | 350 | 77 | 70 |
|  | 450 | 77 | 70 |
| 14-02 | 150 | 37 | 70 |
|  | 250 | 75 | 80 |
|  | 350 | 83 | 97 |
|  | 450 | 95 | 99 |
| 14-03 | 150 | 47 | 53 |
|  | 250 | 77 | 86 |
|  | 350 | 83 | 97 |
|  | 450 | 93 | 100 |
| 14-04 | 150 | 80 | 60 |
|  | 250 | 93 | 83 |
|  | 350 | 96 | 85 |
|  | 450 | 99 | 99 |
| 14-05 | 150 | 80 | 43 |
|  | 250 | 93 | 79 |
|  | 350 | 96 | 94 |
|  | 450 | 98 | 96 |
| 14-06 | 150 | 77 | 53 |
|  | 250 | 85 | 83 |
|  | 350 | 94 | 99 |
|  | 450 | 97 | 99 |
| 14-07 | 150 | 63 | 50 |
|  | 250 | 80 | 88 |
|  | 350 | 85 | 96 |
|  | 450 | 96 | 99 |
| 14-08 | 150 | 27 | 45 |
|  | 250 | 75 | 83 |
|  | 350 | 77 | 99 |
|  | 450 | 96 | 98 |
| 14-09 | 150 | 75 | 57 |
|  | 250 | 80 | 82 |
|  | 350 | 97 | 95 |
|  | 450 | 99 | 98 |
| 14-10 | 150 | 70 | 40 |
|  | 250 | 85 | 83 |
|  | 350 | 97 | 98 |
|  | 450 | 99 | 99 |
| 14-11 | 150 | 53 | 37 |
|  | 250 | 75 | 63 |
|  | 350 | 88 | 93 |
|  | 450 | 92 | 98 |
| 14-12 | 150 | 70 | 40 |
|  | 250 | 78 | 75 |
|  | 350 | 90 | 91 |
|  | 450 | 98 | 98 |
| 14-13 | 150 | 72 | 40 |
|  | 250 | 92 | 80 |
|  | 350 | 97 | 90 |
|  | 450 | 99 | 97 |
| 14-14 | 150 | 78 | 53 |
|  | 250 | 89 | 88 |
|  | 350 | 97 | 95 |
|  | 450 | 99 | 100 |

TABLE 14b-continued

| Concentrate composition | Glyphosate rate g a.e./ha | % Inhibition ABUTH | % Inhibition ECHCF |
|---|---|---|---|
| 14-15 | 150 | 80 | 60 |
|  | 250 | 95 | 97 |
|  | 350 | 98 | 100 |
|  | 450 | 99 | 99 |
| 14-16 | 150 | 60 | 63 |
|  | 250 | 87 | 78 |
|  | 350 | 96 | 94 |
|  | 450 | 98 | 99 |
| 14-17 | 150 | 73 | 60 |
|  | 250 | 85 | 57 |
|  | 350 | 93 | 80 |
|  | 450 | 99 | 85 |

In combination with butyl stearate, steareth-20 (composition 14-04) gave greater herbicidal effectiveness than steareth-10 (14-03) on *ABUTH*. Similarly, oleth-20 (14-09) was more efficacious than oleth-10 (14-08) and ceteth-20 (14-12) than ceteth-10 (14-11). In the absence of butyl stearate, ceteareth-55 (14-17) was noticeably weaker on *ECHCF* than ceteareth-27 (14-15) but inclusion of butyl stearate (14-16) tended to correct this weakness. Note that while compositions 14-14 and 14-15 contained twice as high a concentration of excipients as the other compositions of the test, the concentration of glyphosate was also twice as high, thus the concentrations as sprayed were the same.

Example 15

Aqueous concentrate compositions were prepared containing glyphosate IPA salt and excipient ingredients as shown in Table 15a. Concentrate compositions 15-01 to 15-05, 15-07, 15-08, 15-10 and 15-12 to 15-16 are oil-in-water emulsions and were prepared by process (vii). Concentrate compositions 15-06, 15-09 and 15-11 are aqueous solution concentrates and were prepared by process (viii).

TABLE 15a

| Concentrate composition | Glyphosate g a.e./l | Butyl stearate % w/w | Surfactant % w/w | Type of surfactant |
|---|---|---|---|---|
| 15-01 | 163 | 0.25 | 2.5 | Neodol 1-12 |
| 15-02 | 163 | 0.25 | 2.5 | laureth-23 |
| 15-03 | 163 | 0.25 | 2.5 | steareth-10 |
| 15-04 | 163 | 0.25 | 2.5 | steareth-20 |
| 15-05 | 163 | 0.25 | 2.5 | Pluronic F-68 |
| 15-06 | 163 |  | 2.5 | Pluronic F-68 |
| 15-07 | 326 | 1.00 | 5.0 | Pluronic F-108 |
| 15-08 | 326 | 0.50 | 5.0 | Pluronic F-108 |
| 15-09 | 326 |  | 5.0 | Pluronic F-108 |
| 15-10 | 163 | 0.25 | 2.5 | Pluronic F-127 |
| 15-11 | 163 |  | 2.5 | Pluronic F-127 |
| 15-12 | 326 | 0.50 | 5.0 | ceteareth-27 |
| 15-13 | 163 | 0.25 | 2.5 | ceteareth-55 |
| 15-14 | 163 | 0.25 | 2.5 | oleth-20 |
| 15-15 | 163 | 0.25 | 2.5 | ceteth-20 |
| 15-16 | 163 | 0.25 | 2.5 | steareth-100 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting *ABUTH* and *ECHCF*, and evaluation of herbicidal inhibition was done 15 days after application.

Formulations B, C and J were applied as comparative treatments. Results, averaged for all replicates of each treatment, are shown in Table 15b.

TABLE 15b

| Concentrate composition | Glyphosate rate g a.e./ha | % Inhibition ABUTH | % Inhibition ECHCF |
|---|---|---|---|
| Formulation B | 150 | 5 | 0 |
|  | 250 | 47 | 5 |
|  | 350 | 70 | 23 |
|  | 450 | 75 | 43 |
| Formulation C | 150 | 73 | 47 |
|  | 250 | 99 | 50 |
|  | 350 | 98 | 67 |
|  | 450 | 99 | 75 |
| Formulation J | 150 | 73 | 43 |
|  | 250 | 89 | 50 |
|  | 350 | 97 | 83 |
|  | 450 | 98 | 77 |
| 15-01 | 150 | 37 | 30 |
|  | 250 | 70 | 33 |
|  | 350 | 77 | 40 |
|  | 450 | 90 | 47 |
| 15-02 | 150 | 52 | 37 |
|  | 250 | 77 | 67 |
|  | 350 | 90 | 77 |
|  | 450 | 92 | 75 |
| 15-03 | 150 | 40 | 30 |
|  | 250 | 77 | 70 |
|  | 350 | 80 | 82 |
|  | 450 | 90 | 83 |
| 15-04 | 150 | 75 | 37 |
|  | 250 | 95 | 53 |
|  | 350 | 99 | 91 |
|  | 450 | 99 | 82 |
| 15-05 | 150 | 58 | 37 |
|  | 250 | 65 | 53 |
|  | 350 | 80 | 80 |
|  | 450 | 75 | 68 |
| 15-06 | 150 | 40 | 30 |
|  | 250 | 75 | 33 |
|  | 350 | 78 | 43 |
|  | 450 | 80 | 43 |
| 15-07 | 150 | 50 | 30 |
|  | 250 | 75 | 33 |
|  | 350 | 78 | 53 |
|  | 450 | 86 | 53 |
| 15-08 | 150 | 47 | 30 |
|  | 250 | 75 | 33 |
|  | 350 | 77 | 40 |
|  | 450 | 80 | 50 |
| 15-09 | 150 | 43 | 33 |
|  | 250 | 77 | 40 |
|  | 350 | 78 | 63 |
|  | 450 | 83 | 50 |
| 15-10 | 150 | 27 | 40 |
|  | 250 | 77 | 43 |
|  | 350 | 80 | 50 |
|  | 450 | 92 | 40 |
| 15-11 | 150 | 37 | 30 |
|  | 250 | 72 | 33 |
|  | 350 | 80 | 60 |
|  | 450 | 95 | 40 |
| 15-12 | 150 | 78 | 37 |
|  | 250 | 98 | 40 |
|  | 350 | 99 | 53 |
|  | 450 | 100 | 50 |
| 15-13 | 150 | 75 | 30 |
|  | 250 | 88 | 40 |
|  | 350 | 98 | 47 |
|  | 450 | 100 | 65 |

TABLE 15b-continued

| Concentrate composition | Glyphosate rate g a.e./ha | % Inhibition ABUTH | ECHCF |
|---|---|---|---|
| 15-14 | 150 | 73 | 30 |
|  | 250 | 87 | 40 |
|  | 350 | 98 | 50 |
|  | 450 | 99 | 53 |
| 15-15 | 150 | 72 | 30 |
|  | 250 | 93 | 40 |
|  | 350 | 96 | 43 |
|  | 450 | 99 | 50 |
| 15-16 | 150 | 73 | 40 |
|  | 250 | 83 | 40 |
|  | 350 | 98 | 40 |
|  | 450 | 100 | 47 |

Composition 15-04 containing steareth-20 outperformed its counterpart 15-03 containing steareth-10, though both gave greater herbicidal effectiveness, especially on *ECHCF*, than 15-02 containing laureth-23 or 15-01 containing Neodol 1-12.

Example 16

Aqueous concentrate compositions were prepared containing glyphosate IPA salt and excipient ingredients as shown in Table 16a. Concentrate compositions 16-01 to 16-07 and 16-09 to 16-15 are oil-in-water emulsions and were prepared by process (vii). Concentrate compositions 16-08 and 16-16 are aqueous solution concentrates and were prepared by process (viii).

TABLE 16a

| Concentrate composition | Glyphosate g a.e./l | % w/w Oil | % w/w Surfactant | Type of oil | Type of surfactant |
|---|---|---|---|---|---|
| 16-01 | 163 | 0.5 | 5.0 | methyl stearate | oleth-20 |
| 16-02 | 163 | 0.5 | 5.0 | butyl stearate | oleth-20 |
| 16-03 | 163 | 0.5 | 5.0 | methyl oleate | oleth-20 |
| 16-04 | 163 | 0.5 | 5.0 | butyl oleate | oleth-20 |
| 16-05 | 163 | 0.5 | 5.0 | methyl laurate | oleth-20 |
| 16-06 | 163 | 0.5 | 5.0 | butyl laurate | oleth-20 |
| 16-07 | 163 | 0.5 | 5.0 | Orchex 796 | oleth-20 |
| 16-08 | 163 |  | 5.0 | none | oleth-20 |
| 16-09 | 163 | 0.5 | 5.0 | methyl stearate | Neodol 1-9 |
| 16-10 | 163 | 0.5 | 5.0 | butyl stearate | Neodol 1-9 |
| 16-11 | 163 | 0.5 | 5.0 | methyl oleate | Neodol 1-9 |
| 16-12 | 163 | 0.5 | 5.0 | butyl oleate | Neodol 1-9 |
| 16-13 | 163 | 0.5 | 5.0 | methyl laurate | Neodol 1-9 |
| 16-14 | 163 | 0.5 | 5.0 | butyl laurate | Neodol 1-9 |
| 16-15 | 163 | 0.5 | 5.0 | Orchex 796 | Neodol 1-9 |
| 16-16 | 163 |  | 5.0 | none | Neodol 1-9 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 19 days after application.

Formulations B, C and J were applied as comparative treatments. Results, averaged for all replicates of each treatment, are shown in Table 16b.

TABLE 16b

| Concentrate composition | Glyphosate rate g a.e./ha | % Inhibition ABUTH | ECHCF |
|---|---|---|---|
| Formulation B | 150 | 3 | 10 |
|  | 250 | 58 | 57 |
|  | 350 | 78 | 53 |
|  | 450 | 77 | 53 |
| Formulation C | 150 | 60 | 98 |
|  | 250 | 87 | 99 |
|  | 350 | 95 | 98 |
|  | 450 | 99 | 100 |
| Formulation J | 150 | 60 | 75 |
|  | 250 | 89 | 87 |
|  | 350 | 93 | 90 |
|  | 450 | 98 | 99 |
| 16-01 | 150 | 75 | 96 |
|  | 250 | 99 | 97 |
|  | 350 | 97 | 99 |
|  | 450 | 99 | 100 |
| 16-02 | 150 | 60 | 60 |
|  | 250 | 97 | 67 |
|  | 350 | 99 | 98 |
|  | 450 | 100 | 95 |
| 16-03 | 150 | 63 | 40 |
|  | 250 | 83 | 82 |
|  | 350 | 97 | 86 |
|  | 450 | 97 | 88 |
| 16-04 | 150 | 73 | 40 |
|  | 250 | 94 | 82 |
|  | 350 | 97 | 100 |
|  | 450 | 99 | 100 |
| 16-05 | 150 | 67 | 47 |
|  | 250 | 86 | 67 |
|  | 350 | 97 | 88 |
|  | 450 | 99 | 100 |
| 16-06 | 150 | 60 | 43 |
|  | 250 | 78 | 91 |
|  | 350 | 97 | 83 |
|  | 450 | 94 | 86 |
| 16-07 | 150 | 70 | 53 |
|  | 250 | 80 | 53 |
|  | 350 | 97 | 82 |
|  | 450 | 97 | 92 |
| 16-08 | 150 | 70 | 62 |
|  | 250 | 83 | 83 |
|  | 350 | 91 | 87 |
|  | 450 | 98 | 98 |
| 16-09 | 150 | 45 | 42 |
|  | 250 | 72 | 72 |
|  | 350 | 77 | 73 |
|  | 450 | 78 | 89 |
| 16-10 | 150 | 40 | 30 |
|  | 250 | 82 | 80 |
|  | 350 | 78 | 98 |
|  | 450 | 89 | 93 |
| 16-11 | 150 | 40 | 30 |
|  | 250 | 65 | 60 |
|  | 350 | 77 | 90 |
|  | 450 | 96 | 92 |
| 16-12 | 150 | 20 | 30 |
|  | 250 | 63 | 73 |
|  | 350 | 80 | 75 |
|  | 450 | 93 | 86 |
| 16-13 | 150 | 20 | 27 |
|  | 250 | 67 | 60 |
|  | 350 | 82 | 91 |
|  | 450 | 88 | 92 |

TABLE 16b-continued

| Concentrate composition | Glyphosate rate g a.e./ha | % Inhibition ABUTH | % Inhibition ECHCF |
|---|---|---|---|
| 16-14 | 150 | 7 | 30 |
| | 250 | 72 | 81 |
| | 350 | 87 | 78 |
| | 450 | 80 | 85 |
| 16-15 | 150 | 20 | 23 |

TABLE 16b-continued

| Concentrate composition | Glyphosate rate g a.e./ha | % Inhibition ABUTH | % Inhibition ECHCF |
|---|---|---|---|
| | 250 | 65 | 60 |
| | 350 | 77 | 81 |
| | 450 | 87 | 88 |
| 16-16 | 150 | 12 | 30 |
| | 250 | 57 | 53 |
| | 350 | 68 | 85 |
| | 450 | 85 | 85 |

Composition 16-08, containing as sole excipient substance oleth-20 at a 1:3 weight/weight ratio to glyphosate a.e., exhibited high herbicidal effectiveness, at least equal to commercial standard Formulations C and J on *ABUTH* but a little weaker on *ECHCF*. By comparison, composition 16-16, wherein the sole excipient substance was Neodol 1-9 at the same ratio to glyphosate, had much weaker activity. Addition of a small amount of fatty acid ester in most cases enhanced effectiveness, especially on *ECHCF*. In this study the most efficacious composition was 16-01, containing oleth-20 and methyl stearate. When added to Neodol 1-9, butyl stearate was more efficacious than methyl stearate, methyl oleate or butyl oleate. The mineral oil Orchex 796 did not substitute effectively for butyl stearate, either with oleth-20 or with Neodol 1-9.

Example 17

Aqueous concentrate compositions were prepared containing glyphosate IPA salt and excipient ingredients as shown in Table 17a. Concentrate compositions 17-01, 17-03, 17-05 to 17-08, 17-10 and 17-14 to 17-17 are oil-in-water emulsions and were prepared by process (vii). Concentrate compositions 17-02, 17-04, 17-09 and 17-11 to 17-13 are aqueous solution concentrates and were prepared by process (viii). Some compositions contained a coupling agent as indicated in Table 17a; the coupling agent was added with the surfactant.

TABLE 17a

| Conc. comp. | Glyphosate g a.e./l | % w/w Butyl stearate | % w/w Surfactant | % w/w Coupling agent | Type of coupling agent | Type of surfactant |
|---|---|---|---|---|---|---|
| 17-01 | 326 | 1.0 | 5.0 | 2.5 | Arcosolve DPM | oleth-20 |
| 17-02 | 326 | | 5.0 | 2.5 | Arcosolve DPM | oleth-20 |
| 17-03 | 163 | 0.5 | 2.5 | | none | oleth-20 |
| 17-04 | 163 | | 2.5 | | none | oleth-20 |
| 17-05 | 326 | 1.0 | 5.0 | | none | ceteareth-27 |
| 17-06 | 326 | 1.0 | 5.0 | 2.5 | PEG-400 | ceteareth-27 |
| 17-07 | 326 | 1.0 | 5.0 | 2.5 | Dowanol TPNB | ceteareth-27 |
| 17-08 | 326 | 1.0 | 5.0 | 2.5 | Dowanol PNB | ceteareth-27 |
| 17-09 | 163 | | 2.5 | | none | ceteareth-27 |
| 17-10 | 326 | 0.5 | 5.0 | | none | ceteareth-27 |
| 17-11 | 326 | | 5.0 | 2.5 | PEG-400 | ceteareth-27 |
| 17-12 | 326 | | 5.0 | 2.5 | Dowanol TPNB | ceteareth-27 |
| 17-13 | 326 | | 5.0 | 2.5 | Dowanol PNB | ceteareth-27 |
| 17-14 | 163 | 0.5 | 2.5 | | none | Neodol 1-9 |
| 17-15 | 163 | 0.5 | 2.5 | | none | laureth-23 |
| 17-16 | 163 | 0.5 | 2.5 | | none | steareth-20 |
| 17-17 | 163 | 0.5 | 2.5 | | none | ceteareth-27 |

Velvetleaf (*Abutilon theophrasti*, *ABUTH*) and Japanese millet (*Echinochloa crus-galli*, *ECHCF*) plants were grown and treated by the standard procedures given above. Applications of spray compositions were made 16 days after planting *ABUTH* and *ECHCF*, and evaluation of herbicidal inhibition was done 18 days after application.

Formulations B, C and J were applied as comparative treatments. Results, averaged for all replicates of each treatment, are shown in Table 17b.

TABLE 17b

| Concentrate composition | Glyphosate rate g a.e./ha | % Inhibition ABUTH | % Inhibition ECHCF |
|---|---|---|---|
| Formulation B | 150 | 0 | 5 |
| | 250 | 38 | 20 |
| | 350 | 63 | 30 |
| | 450 | 70 | 70 |
| Formulation C | 150 | 70 | 75 |
| | 250 | 92 | 94 |
| | 350 | 99 | 99 |
| | 450 | 99 | 98 |
| Formulation J | 150 | 65 | 50 |
| | 250 | 88 | 92 |
| | 350 | 97 | 99 |
| | 450 | 98 | 97 |
| 17-01 | 150 | 58 | 83 |
| | 250 | 77 | 88 |
| | 350 | 93 | 96 |
| | 450 | 93 | 99 |
| 17-02 | 150 | 40 | 76 |
| | 250 | 75 | 100 |

TABLE 17b-continued

| Concentrate composition | Glyphosate rate g a.e./ha | % Inhibition ABUTH | % Inhibition ECHCF |
|---|---|---|---|
| | 350 | 92 | 100 |
| | 450 | 92 | 100 |
| 17-03 | 150 | 48 | 75 |
| | 250 | 83 | 96 |
| | 350 | 92 | 100 |
| | 450 | 99 | 100 |
| 17-04 | 150 | 40 | 82 |
| | 250 | 78 | 99 |
| | 350 | 87 | 99 |
| | 450 | 98 | 100 |
| 17-05 | 150 | 68 | 92 |
| | 250 | 87 | 99 |
| | 350 | 95 | 99 |
| | 450 | 99 | 99 |
| 17-06 | 150 | 55 | 60 |
| | 250 | 83 | 99 |
| | 350 | 97 | 99 |
| | 450 | 98 | 98 |
| 17-07 | 150 | 63 | 57 |
| | 250 | 80 | 96 |
| | 350 | 95 | 97 |
| | 450 | 99 | 98 |
| 17-08 | 150 | 73 | 75 |
| | 250 | 90 | 90 |
| | 350 | 95 | 97 |
| | 450 | 100 | 97 |
| 17-09 | 150 | 73 | 68 |
| | 250 | 87 | 73 |
| | 350 | 92 | 90 |
| | 450 | 97 | 95 |
| 17-10 | 150 | 70 | 63 |
| | 250 | 87 | 80 |
| | 350 | 98 | 94 |
| | 450 | 99 | 96 |
| 17-11 | 150 | 73 | 60 |
| | 250 | 90 | 77 |
| | 350 | 99 | 93 |
| | 450 | 100 | 95 |
| 17-12 | 150 | 72 | 67 |
| | 250 | 83 | 75 |
| | 350 | 90 | 82 |
| | 450 | 99 | 94 |
| 17-13 | 150 | 73 | 70 |
| | 250 | 80 | 83 |
| | 350 | 99 | 94 |
| | 450 | 100 | 92 |
| 17-14 | 150 | 5 | 20 |
| | 250 | 55 | 63 |
| | 350 | 77 | 93 |
| | 450 | 78 | 99 |
| 17-15 | 150 | 43 | 57 |
| | 250 | 78 | 88 |
| | 350 | 88 | 98 |
| | 450 | 90 | 98 |
| 17-16 | 150 | 65 | 57 |
| | 250 | 83 | 82 |
| | 350 | 88 | 98 |
| | 450 | 95 | 97 |
| 17-17 | 150 | 72 | 50 |
| | 250 | 80 | 93 |
| | 350 | 88 | 90 |
| | 450 | 95 | 97 |

The superiority of herbicidal effectiveness provided by $C_{16-18}$ alkylethers (oleth-20, ceteareth-27, steareth-20) over that provided by shorter chain alkylethers (Neodol 1-9, laureth-23) was very pronounced in this test.

Example 18

Aqueous concentrate compositions were prepared containing glyphosate IPA salt and excipient ingredients as shown in Table 18a. Concentrate compositions 18-01 to 18-07 and 18-09 to 18-15 are oil-in-water emulsions and were prepared by process (vii). Concentrate compositions 18-08 and 18-16 are aqueous solution concentrates and were prepared by process (viii).

TABLE 18a

| Concentrate composition | Glyphosate g a.e./l | % w/w Oil | % w/w Surfactant | Type of oil | Type of surfactant |
|---|---|---|---|---|---|
| 18-01 | 163 | 0.5 | 5.0 | methyl stearate | steareth-20 |
| 18-02 | 163 | 0.5 | 5.0 | butyl stearate | steareth-20 |
| 18-03 | 163 | 0.5 | 5.0 | methyl oleate | steareth-20 |
| 18-04 | 163 | 0.5 | 5.0 | butyl oleate | steareth-20 |
| 18-05 | 163 | 0.5 | 5.0 | methyl laurate | steareth-20 |
| 18-06 | 163 | 0.5 | 5.0 | butyl laurate | steareth-20 |
| 18-07 | 163 | 0.5 | 5.0 | Orchex 796 | steareth-20 |
| 18-08 | 163 | | 5.0 | none | steareth-20 |
| 18-09 | 163 | 0.5 | 5.0 | methyl stearate | ceteareth-27 |
| 18-10 | 163 | 0.5 | 5.0 | butyl stearate | ceteareth-27 |
| 18-11 | 163 | 0.5 | 5.0 | methyl oleate | ceteareth-27 |
| 18-12 | 163 | 0.5 | 5.0 | butyl oleate | ceteareth-27 |
| 18-13 | 163 | 0.5 | 5.0 | methyl laurate | ceteareth-27 |
| 18-14 | 163 | 0.5 | 5.0 | butyl laurate | ceteareth-27 |
| 18-15 | 163 | 0.5 | 5.0 | Orchex 796 | ceteareth-27 |
| 18-16 | 163 | | 5.0 | none | ceteareth-27 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting *ABUTH* and *ECHCF*, and evaluation of herbicidal inhibition was done 18 days after application.

Formulations B, C and J were applied as comparative treatments. Results, averaged for all replicates of each treatment, are shown in Table 18b.

TABLE 18b

| Concentrate composition | Glyphosate rate g a.e./ha | % Inhibition ABUTH | % Inhibition ECHCF |
|---|---|---|---|
| Formulation B | 150 | 15 | 5 |
| | 250 | 57 | 20 |
| | 350 | 83 | 50 |
| | 450 | 78 | 73 |
| Formulation C | 150 | 65 | 63 |
| | 250 | 87 | 93 |
| | 350 | 92 | 94 |
| | 450 | 98 | 100 |
| Formulation J | 150 | 50 | 73 |
| | 250 | 90 | 90 |
| | 350 | 94 | 98 |
| | 450 | 98 | 99 |
| 18-01 | 150 | 72 | 70 |
| | 250 | 88 | 85 |
| | 350 | 96 | 83 |
| | 450 | 99 | 86 |
| 18-02 | 150 | 73 | 53 |
| | 250 | 83 | 87 |
| | 350 | 97 | 99 |
| | 450 | 97 | 98 |
| 18-03 | 150 | 68 | 33 |
| | 250 | 87 | 92 |
| | 350 | 93 | 97 |
| | 450 | 98 | 93 |

TABLE 18b-continued

| Concentrate composition | Glyphosate rate g a.e./ha | % Inhibition ABUTH | % Inhibition ECHCF |
|---|---|---|---|
| 18-04 | 150 | 72 | 50 |
|  | 250 | 87 | 88 |
|  | 350 | 94 | 86 |
|  | 450 | 98 | 97 |
| 18-05 | 150 | 72 | 67 |
|  | 250 | 83 | 82 |
|  | 350 | 99 | 97 |
|  | 450 | 98 | 98 |
| 18-06 | 150 | 73 | 33 |
|  | 250 | 95 | 83 |
|  | 350 | 99 | 95 |
|  | 450 | 99 | 88 |
| 18-07 | 150 | 73 | 55 |
|  | 250 | 93 | 73 |
|  | 350 | 95 | 83 |
|  | 450 | 98 | 91 |
| 18-08 | 150 | 75 | 40 |
|  | 250 | 94 | 60 |
|  | 350 | 98 | 86 |
|  | 450 | 99 | 92 |
| 18-09 | 150 | 77 | 50 |
|  | 250 | 90 | 50 |
|  | 350 | 98 | 92 |
|  | 450 | 99 | 98 |
| 18-10 | 150 | 72 | 53 |
|  | 250 | 92 | 77 |
|  | 350 | 96 | 86 |
|  | 450 | 99 | 99 |
| 18-11 | 150 | 72 | 60 |
|  | 250 | 87 | 87 |
|  | 350 | 97 | 97 |
|  | 450 | 97 | 99 |
| 18-12 | 150 | 70 | 57 |
|  | 250 | 90 | 90 |
|  | 350 | 96 | 96 |
|  | 450 | 98 | 99 |
| 18-13 | 150 | 68 | 40 |
|  | 250 | 90 | 77 |
|  | 350 | 99 | 95 |
|  | 450 | 99 | 98 |
| 18-14 | 150 | 77 | 33 |
|  | 250 | 94 | 70 |
|  | 350 | 96 | 82 |
|  | 450 | 99 | 93 |
| 18-15 | 150 | 75 | 30 |
|  | 250 | 96 | 75 |
|  | 350 | 97 | 88 |
|  | 450 | 99 | 92 |
| 18-16 | 150 | 77 | 40 |
|  | 250 | 99 | 47 |
|  | 350 | 98 | 67 |
|  | 450 | 98 | 78 |

Steareth-20 and ceteareth-27, as sole excipient substances (compositions 18-08 and 18-16 respectively) provided excellent herbicidal effectiveness, but further enhancements, especially on *ECHCF*, were obtained by inclusion of a small amount of fatty acid ester in the composition.

Example 19

Aqueous concentrate compositions were prepared containing glyphosate IPA salt and excipient ingredients as shown in Table 19a. Concentrate compositions 19-13 and 19-14 are aqueous solution concentrates and were prepared by process (viii). Concentrate compositions 19-01 to 19-12 and 19-15 are aqueous solution concentrates containing colloidal particulates and were prepared by process (ix). Concentrate compositions 19-16 and 19-17 contained colloidal particulates but no surfactant.

Compositions 19-13 and 19-14 (both containing 162 g a.e./l glyphosate) showed acceptable storage stability. However, at glyphosate loadings >480 g a.e./l (as in compositions 19-01 to 19-12 and 19-15) storage-stable compositions containing 3% oleth-20 could not be made except with the addition of colloidal particulate as shown below.

TABLE 19a

| Concentrate composition | Glyphosate g a.e./l | % w/w Oleth-20 | % w/w Glycerin | % w/w Aerosil | Type of Aerosil |
|---|---|---|---|---|---|
| 19-01 | 492 | 3.00 | 2.0 | 0.8 | 380 |
| 19-02 | 492 | 3.00 | 5.0 | 1.5 | 380 |
| 19-03 | 492 | 3.00 | 2.0 | 0.8 | 380 |
| 19-04 | 492 | 3.00 | 5.0 | 1.5 | 380 |
| 19-05 | 492 | 3.00 |  | 0.8 | OX-50 |
| 19-06 | 492 | 3.00 |  | 1.5 | OX-50 |
| 19-07 | 492 | 3.00 |  | 0.8 | 380/OX-50 blend |
| 19-08 | 492 | 3.00 |  | 1.5 | 380/OX-50 blend |
| 19-09 | 492 | 3.00 |  | 0.8 | 380 |
| 19-10 | 492 | 3.00 |  | 1.5 | 380 |
| 19-11 | 492 | 3.00 |  | 0.8 | 380 |
| 19-12 | 492 | 3.00 |  | 1.5 | 380 |
| 19-13 | 162 | 1.13 |  |  | none |
| 19-14 | 162 | 1.13 |  |  | none |
| 19-15 | 492 | 3.00 | 2.0 | 1.5 | 380 |
| 19-16 | 488 |  |  | 0.8 | 380 |
| 19-17 | 488 |  |  | 1.5 | 380 |

Velvetleaf (*Abutilon theophrasti, ABUTH*) and Japanese millet (*Echinochloa crus-galli, ECHCF*) plants were grown and treated by the standard procedures given above. Applications of spray compositions were made 17 days after planting *ABUTH* and *ECHCF*, and evaluation of herbicidal inhibition was done 18 days after application.

Formulations B and J were applied as comparative treatments. Results, averaged for all replicates of each treatment, are shown in Table 19b.

TABLE 19b

| Concentrate composition | Glyphosate rate g a.e./ha | % Inhibition ABUTH | % Inhibition ECHCF |
|---|---|---|---|
| Formulation B | 150 | 18 | 40 |
|  | 250 | 57 | 53 |
|  | 350 | 72 | 63 |
|  | 450 | 83 | 85 |
| Formulation J | 150 | 70 | 65 |
|  | 250 | 85 | 95 |
|  | 350 | 98 | 98 |
|  | 450 | 100 | 99 |
| 19-01 | 150 | 62 | 67 |
|  | 250 | 72 | 93 |
|  | 350 | 99 | 96 |
|  | 450 | 99 | 97 |
| 19-02 | 150 | 57 | 50 |
|  | 250 | 70 | 91 |
|  | 350 | 92 | 97 |
|  | 450 | 99 | 99 |
| 19-03 | 150 | 48 | 40 |
|  | 250 | 68 | 67 |
|  | 350 | 97 | 97 |
|  | 450 | 98 | 98 |

TABLE 19b-continued

| Concentrate composition | Glyphosate rate g a.e./ha | % Inhibition ABUTH | % Inhibition ECHCF |
|---|---|---|---|
| 19-04 | 150 | 55 | 50 |
|  | 250 | 82 | 83 |
|  | 350 | 95 | 90 |
|  | 450 | 99 | 94 |
| 19-05 | 150 | 65 | 43 |
|  | 250 | 87 | 87 |
|  | 350 | 100 | 94 |
|  | 450 | 96 | 95 |
| 19-06 | 150 | 55 | 53 |
|  | 250 | 75 | 82 |
|  | 350 | 95 | 95 |
|  | 450 | 100 | 96 |
| 19-07 | 150 | 45 | 83 |
|  | 250 | 78 | 82 |
|  | 350 | 90 | 93 |
|  | 450 | 95 | 99 |
| 19-08 | 150 | 55 | 47 |
|  | 250 | 75 | 88 |
|  | 350 | 93 | 99 |
|  | 450 | 99 | 97 |
| 19-09 | 150 | 47 | 47 |
|  | 250 | 65 | 82 |
|  | 350 | 78 | 99 |
|  | 450 | 97 | 97 |
| 19-10 | 150 | 47 | 40 |
|  | 250 | 72 | 96 |
|  | 350 | 77 | 80 |
|  | 450 | 85 | 97 |
| 19-11 | 150 | 37 | 53 |
|  | 250 | 73 | 82 |
|  | 350 | 80 | 83 |
|  | 450 | 90 | 92 |
| 19-12 | 150 | 35 | 57 |
|  | 250 | 70 | 82 |
|  | 350 | 80 | 97 |
|  | 450 | 90 | 99 |
| 19-13 | 150 | 50 | 40 |
|  | 250 | 68 | 75 |
|  | 350 | 95 | 92 |
|  | 450 | 99 | 95 |
| 19-14 | 150 | 40 | 33 |
|  | 250 | 70 | 82 |
|  | 350 | 93 | 89 |
|  | 450 | 98 | 93 |
| 19-15 | 150 | 23 | 33 |
|  | 250 | 67 | 73 |
|  | 350 | 83 | 91 |
|  | 450 | 94 | 92 |
| 19-16 | 150 | 13 | 40 |
|  | 250 | 45 | 50 |
|  | 350 | 62 | 72 |
|  | 450 | 77 | 77 |
| 19-17 | 150 | 7 | 33 |
|  | 250 | 50 | 50 |
|  | 350 | 60 | 70 |
|  | 450 | 75 | 73 |

Several high-loaded (492 g a.e./l) glyphosate compositions containing oleth-20 at just 3% exhibited surprisingly high herbicidal effectiveness, approaching or equalling that of commercial standard Formulation J, which is loaded at only about 360 g a.e./l and has a much higher surfactant to glyphosate ratio.

Example 20

Aqueous concentrate compositions were prepared containing glyphosate IPA salt and excipient ingredients as shown in Table 20a. Concentrate composition 20-08 to 20-14 are oil-in-water emulsions and were prepared by process (vii). Concentrate compositions 20-15 to 20-17 are aqueous solution concentrates and were prepared by process (viii). Concentrate compositions 20-01 to 20-07 contain colloidal particulates and were prepared by process (ix).

Compositions 20-08 to 20-17 (all containing 163 g a.e./l glyphosate) showed acceptable storage stability. However, at a glyphosate loading of 400 g a.e./l (as in compositions 20-01 to 20-07) storage-stable compositions containing 0.5–1% butyl stearate and 5–10% alkylether surfactant could not be made except with the addition of colloidal particulate as shown below.

TABLE 20a

| Concentrate composition | Glyphosate g a.e./l | % w/w Butyl stearate | % w/w Surfactant | % w/w Aerosil 90 | Type of surfactant |
|---|---|---|---|---|---|
| 20-01 | 400 | 1.0 | 10.0 | 1.0 | ceteareth-27 |
| 20-02 | 400 | 1.0 | 10.0 | 1.0 | steareth-20 |
| 20-03 | 400 | 0.5 | 5.0 | 1.0 | ceteareth-27 |
| 20-04 | 400 | 0.5 | 5.0 | 1.0 | steareth-20 |
| 20-05 | 400 | 1.0 | 5.0 | 1.0 | ceteareth-27 |
| 20-06 | 400 | 1.0 | 5.0 | 1.0 | steareth-20 |
| 20-07 | 400 | 1.0 | 5.0 | 1.0 | steareth-30 |
| 20-08 | 163 | 0.5 | 5.0 |  | oleth-20 |
| 20-09 | 163 | 0.5 | 5.0 |  | steareth-20 |
| 20-10 | 163 | 0.5 | 5.0 |  | ceteth-20 |
| 20-11 | 163 | 0.5 | 5.0 |  | laureth-23 |
| 20-12 | 163 | 0.5 | 5.0 |  | ceteareth-27 |
| 20-13 | 163 | 0.5 | 5.0 |  | Neodol 25-12 |
| 20-14 | 163 | 0.5 | 5.0 |  | Neodol 25-20 |
| 20-15 | 163 |  | 5.0 |  | steareth-20 |
| 20-16 | 163 |  | 5.0 |  | ceteth-20 |
| 20-17 | 163 |  | 5.0 |  | laureth-23 |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and ECHCF, and evaluation of herbicidal inhibition was done 19 days after application.

Formulations B, C and J were applied as comparative treatments. Results, averaged for all replicates of each treatment, are shown in Table 20b.

TABLE 20b

| Composition applied | Glyphosate rate g a.e./ha | % Inhibition ABUTH | % Inhibition ECHCF |
|---|---|---|---|
| Formulation B | 150 | 0 | 40 |
|  | 250 | 20 | 60 |
|  | 350 | 68 | 82 |
|  | 450 | 83 | 96 |
| Formulation C | 150 | 68 | 93 |
|  | 250 | 93 | 99 |
|  | 350 | 100 | 100 |
|  | 450 | 100 | 100 |
| Formulation J | 150 | 43 | 89 |
|  | 250 | 93 | 100 |
|  | 350 | 100 | 100 |
|  | 450 | 100 | 100 |
| 20-01 | 150 | 78 | 97 |
|  | 250 | 96 | 100 |
|  | 350 | 98 | 100 |
|  | 450 | 100 | 100 |
| 20-02 | 150 | 91 | 98 |
|  | 250 | 100 | 100 |
|  | 350 | 100 | 100 |
|  | 450 | 100 | 100 |

TABLE 20b-continued

| Composition applied | Glyphosate rate g a.e./ha | % Inhibition ABUTH | ECHCF |
|---|---|---|---|
| 20-03 | 150 | 90 | 97 |
| | 250 | 99 | 99 |
| | 350 | 100 | 100 |
| | 450 | 100 | 100 |
| 20-04 | 150 | 77 | 98 |
| | 250 | 100 | 100 |
| | 350 | 100 | 100 |
| | 450 | 100 | 100 |
| 20-05 | 150 | 82 | 93 |
| | 250 | 100 | 99 |
| | 350 | 100 | 100 |
| | 450 | 100 | 100 |
| 20-06 | 150 | 83 | 85 |
| | 250 | 100 | 99 |
| | 350 | 100 | 100 |
| | 450 | 100 | 100 |
| 20-07 | 150 | 83 | 87 |
| | 250 | 100 | 100 |
| | 350 | 100 | 100 |
| | 450 | 100 | 100 |
| 20-08 | 150 | 90 | 92 |
| | 250 | 100 | 100 |
| | 350 | 100 | 100 |
| | 450 | 100 | 100 |
| 20-09 | 150 | 90 | 85 |
| | 250 | 100 | 98 |
| | 350 | 100 | 100 |
| | 450 | 100 | 100 |
| 20-10 | 150 | 80 | 85 |
| | 250 | 100 | 92 |
| | 350 | 100 | 100 |
| | 450 | 100 | 100 |
| 20-11 | 150 | 83 | 88 |
| | 250 | 96 | 99 |
| | 350 | 100 | 98 |
| | 450 | 100 | 100 |
| 20-12 | 150 | 93 | 85 |
| | 250 | 100 | 99 |
| | 350 | 100 | 100 |
| | 450 | 100 | 100 |
| 20-13 | 150 | 72 | 73 |
| | 250 | 92 | 97 |
| | 350 | 100 | 99 |
| | 450 | 100 | 100 |
| 20-14 | 150 | 72 | 80 |
| | 250 | 99 | 99 |
| | 350 | 100 | 100 |
| | 450 | 100 | 100 |
| 20-15 | 150 | 100 | 93 |
| | 250 | 100 | 99 |
| | 350 | 100 | 100 |
| | 450 | 100 | 100 |
| 20-16 | 150 | 100 | 98 |
| | 250 | 100 | 100 |
| | 350 | 100 | 100 |
| | 450 | 100 | 100 |
| 20-17 | 150 | 83 | 83 |
| | 250 | 100 | 99 |
| | 350 | 100 | 99 |
| | 450 | 100 | 99 |

Outstanding herbicidal effectiveness was provided by compositions containing $C_{16-18}$ alkylether surfactants (ceteareth-27, steareth-20, steareth-30, oleth-20, ceteth-20). High-loaded (400 g a.e./l) glyphosate compositions containing a $C_{16-18}$ alkylether surfactant, butyl stearate and a colloidal particulate (Aerosil 90) to stabilize the compositions performed especially impressively in this test.

Example 21

Aqueous concentrate compositions were prepared containing glyphosate IPA salt and excipient ingredients as shown in Table 21a. Concentrate composition 21-01 to 21-09, 21-11 to 21-14, 21-16 and 21-17 are oil-in-water emulsions and were prepared by process (vii). Concentrate compositions 21-10 and 21-15 are aqueous solution concentrates and were prepared by process (viii).

TABLE 21a

| Conc. comp. | Gly-phosate g a.e./l | % w/w Oil | Oleth-20 | Other surfactant | Type of oil | Other surfactant |
|---|---|---|---|---|---|---|
| 21-01 | 163 | 0.25 | 2.5 | | methyl laurate | |
| 21-02 | 163 | 0.25 | 2.5 | | methyl myristate | |
| 21-03 | 163 | 0.25 | 2.5 | | methyl palmitoleate | |
| 21-04 | 163 | 0.25 | 2.5 | | methyl palmitate | |
| 21-05 | 163 | 0.25 | 2.5 | | methyl linoleate | |
| 21-06 | 163 | 0.25 | 2.5 | | methyl oleate | |
| 21-07 | 163 | 0.25 | 2.5 | | methyl stearate | |
| 21-08 | 163 | 0.25 | 2.5 | | ethyl stearate | |
| 21-09 | 163 | 0.25 | 2.5 | | butyl stearate | |
| 21-10 | 163 | | 2.5 | | none | |
| 21-11 | 163 | 0.25 | | 2.5 | methyl palmitoleate | MON 0818 |
| 21-12 | 163 | 0.25 | | 2.5 | methyl palmitate | MON 0818 |
| 21-13 | 163 | 0.25 | | 2.5 | methyl oleate | MON 0818 |
| 21-14 | 163 | 0.25 | | 2.5 | methyl stearate | MON 0818 |
| 21-15 | 163 | | | 2.5 | none | MON 0818 |
| 21-16 | 163 | 0.25 | | 2.5 | butyl stearate | laureth-23 |
| 21-17 | 163 | 0.25 | | 2.5 | butyl stearate | Neodol 1-9 |

Velvetleaf (*Abutilon theophrasti*, ABUTH) and Japanese millet (*Echinochloa crus-galli*, ECHCF) plants were grown and treated by the standard procedures given above. Applications of spray compositions were made 20 days after planting ABUTH and ECHCF, and evaluation of herbicidal inhibition was done 16 days after application.

Formulations B, C and J were applied as comparative treatments. Results, averaged for all replicates of each treatment, are shown in Table 21b.

TABLE 21b

| Concentrate composition | Glyphosate rate g a.e./ha | % Inhibition ABUTH | ECHCF |
|---|---|---|---|
| Formulation B | 100 | 2 | 35 |
| | 200 | 52 | 67 |
| | 300 | 77 | 83 |
| | 400 | 78 | 87 |
| Formulation C | 100 | 25 | 77 |
| | 200 | 72 | 99 |
| | 300 | 87 | 100 |
| | 400 | 99 | 100 |
| Formulation J | 100 | 13 | 73 |
| | 200 | 70 | 97 |
| | 300 | 90 | 100 |
| | 400 | 97 | 100 |
| 21-01 | 100 | 22 | 55 |
| | 200 | 65 | 86 |
| | 300 | 78 | 98 |
| | 400 | 89 | 98 |

TABLE 21b-continued

| Concentrate composition | Glyphosate rate g a.e./ha | % Inhibition ABUTH | ECHCF |
|---|---|---|---|
| 21-02 | 100 | 20 | 63 |
|  | 200 | 67 | 91 |
|  | 300 | 83 | 99 |
|  | 400 | 97 | 100 |
| 21-03 | 100 | 30 | 75 |
|  | 200 | 63 | 98 |
|  | 300 | 83 | 99 |
|  | 400 | 94 | 100 |
| 21-04 | 100 | 23 | 63 |
|  | 200 | 60 | 98 |
|  | 300 | 90 | 99 |
|  | 400 | 95 | 100 |
| 21-05 | 100 | 27 | 57 |
|  | 200 | 62 | 91 |
|  | 300 | 83 | 96 |
|  | 400 | 93 | 98 |
| 21-06 | 100 | 23 | 50 |
|  | 200 | 63 | 89 |
|  | 300 | 83 | 99 |
|  | 400 | 96 | 99 |
| 21-07 | 100 | 25 | 53 |
|  | 200 | 65 | 94 |
|  | 300 | 83 | 99 |
|  | 400 | 92 | 99 |
| 21-08 | 100 | 13 | 47 |
|  | 200 | 53 | 88 |
|  | 300 | 89 | 97 |
|  | 400 | 95 | 99 |
| 21-09 | 100 | 27 | 53 |
|  | 200 | 60 | 85 |
|  | 300 | 83 | 97 |
|  | 400 | 97 | 98 |
| 21-10 | 100 | 13 | 53 |
|  | 200 | 62 | 94 |
|  | 300 | 83 | 97 |
|  | 400 | 88 | 99 |
| 21-11 | 100 | 23 | 60 |
|  | 200 | 50 | 90 |
|  | 300 | 85 | 98 |
|  | 400 | 95 | 99 |
| 21-12 | 100 | 17 | 55 |
|  | 200 | 35 | 94 |
|  | 300 | 78 | 98 |
|  | 400 | 94 | 99 |
| 21-13 | 100 | 8 | 50 |
|  | 200 | 43 | 90 |
|  | 300 | 73 | 98 |
|  | 400 | 90 | 99 |
| 21-14 | 100 | 30 | 63 |
|  | 200 | 45 | 92 |
|  | 300 | 80 | 98 |
|  | 400 | 94 | 98 |
| 21-15 | 100 | 20 | 63 |
|  | 200 | 70 | 96 |
|  | 300 | 82 | 99 |
|  | 400 | 94 | 98 |
| 21-16 | 100 | 18 | 62 |
|  | 200 | 62 | 83 |
|  | 300 | 80 | 97 |
|  | 400 | 97 | 97 |
| 21-17 | 100 | 17 | 52 |
|  | 200 | 58 | 85 |
|  | 300 | 75 | 90 |
|  | 400 | 95 | 98 |

No great or consistent enhancement of herbicidal effectiveness of glyphosate compositions containing oleth-20 was obtained by adding a small amount of any of a variety of fatty acid esters in this study (compare 21-10 with 21-01 to 21-09).

Example 22

Aqueous concentrate compositions were prepared containing glyphosate IPA salt and excipient ingredients as shown in Table 22a. Concentrate composition 22-01 to 22-09, 22-11 to 22-14, 22-16 and 22-17 are oil-in-water emulsions and were prepared by process (vii). Concentrate compositions 22-10 and 22-15 are aqueous solution concentrates and were prepared by process (viii).

TABLE 22a

| Concentrate composition | Glyphosate g a.e./l | % w/w Oil | Oleth-20 | Other surfactant | Type of oil | Other surfactant |
|---|---|---|---|---|---|---|
| 22-01 | 163 | 0.25 | 2.5 |  | isopropyl myristate |  |
| 22-02 | 163 | 0.25 | 2.5 |  | ethyl myristate |  |
| 22-03 | 163 | 0.25 | 2.5 |  | methyl palmitate |  |
| 22-04 | 163 | 0.25 | 2.5 |  | ethyl palmitate |  |
| 22-05 | 163 | 0.25 | 2.5 |  | ethyl linoleate |  |
| 22-06 | 163 | 0.25 | 2.5 |  | ethyl oleate |  |
| 22-07 | 163 | 0.25 | 2.5 |  | methyl stearate |  |
| 22-08 | 163 | 0.25 | 2.5 |  | ethyl stearate |  |
| 22-09 | 163 | 0.25 | 2.5 |  | butyl stearate |  |
| 22-10 | 163 |  | 2.5 |  | none |  |
| 22-11 | 163 | 0.25 |  | 2.5 | methyl palmitate | MON 0818 |
| 22-12 | 163 | 0.25 |  | 2.5 | methyl stearate | MON 0818 |
| 22-13 | 163 | 0.25 |  | 2.5 | ethyl stearate | MON 0818 |
| 22-14 | 163 | 0.25 |  | 2.5 | ethyl oleate | MON 0818 |
| 22-15 | 163 |  |  | 2.5 | none | MON 0818 |
| 22-16 | 163 | 0.25 |  | 2.5 | butyl stearate | laureth-23 |
| 22-17 | 163 | 0.25 |  | 2.5 | butyl stearate | Neodol 1-9 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and ECHCF, and evaluation of herbicidal inhibition was done 18 days after application.

Formulations B, C and J were applied as comparative treatments. Results, averaged for all replicates of each treatment, are shown in Table 22b.

TABLE 22b

| Concentrate composition | Glyphosate rate g a.e./ha | % Inhibition ABUTH | ECHCF |
|---|---|---|---|
| Formulation B | 100 | 12 | 33 |
|  | 200 | 45 | 43 |
|  | 300 | 73 | 63 |
|  | 400 | 80 | 63 |
| Formulation C | 100 | 43 | 57 |
|  | 200 | 75 | 88 |
|  | 300 | 95 | 99 |
|  | 400 | 100 | 99 |
| Formulation J | 100 | 53 | 60 |
|  | 200 | 77 | 75 |
|  | 300 | 96 | 95 |
|  | 400 | 99 | 98 |
| 22-01 | 100 | 35 | 40 |
|  | 200 | 73 | 72 |
|  | 300 | 83 | 91 |
|  | 400 | 99 | 97 |
| 22-02 | 100 | 38 | 30 |
|  | 200 | 70 | 43 |

TABLE 22b-continued

| Concentrate composition | Glyphosate rate g a.e./ha | % Inhibition ABUTH | ECHCF |
|---|---|---|---|
| | 300 | 87 | 82 |
| | 400 | 96 | 80 |
| 22-03 | 100 | 25 | 27 |
| | 200 | 68 | 50 |
| | 300 | 90 | 73 |
| | 400 | 96 | 82 |
| 22-04 | 100 | 27 | 27 |
| | 200 | 75 | 50 |
| | 300 | 80 | 73 |
| | 400 | 96 | 80 |
| 22-05 | 100 | 33 | 27 |
| | 200 | 68 | 43 |
| | 300 | 83 | 70 |
| | 400 | 97 | 91 |
| 22-06 | 100 | 33 | 28 |
| | 200 | 72 | 53 |
| | 300 | 83 | 60 |
| | 400 | 99 | 70 |
| 22-07 | 100 | 37 | 25 |
| | 200 | 72 | 40 |
| | 300 | 83 | 50 |
| | 400 | 97 | 65 |
| 22-08 | 100 | 32 | 25 |
| | 200 | 73 | 43 |
| | 300 | 87 | 60 |
| | 400 | 98 | 67 |
| 22-09 | 100 | 35 | 25 |
| | 200 | 75 | 43 |
| | 300 | 95 | 57 |
| | 400 | 98 | 63 |
| 22-10 | 100 | 35 | 27 |
| | 200 | 73 | 40 |
| | 300 | 83 | 76 |
| | 400 | 97 | 73 |
| 22-11 | 100 | 35 | 33 |
| | 200 | 67 | 67 |
| | 300 | 80 | 86 |
| | 400 | 92 | 70 |
| 22-12 | 100 | 25 | 30 |
| | 200 | 67 | 70 |
| | 300 | 83 | 76 |
| | 400 | 88 | 80 |
| 22-13 | 100 | 27 | 33 |
| | 200 | 70 | 66 |
| | 300 | 78 | 63 |
| | 400 | 93 | 60 |
| 22-14 | 100 | 33 | 30 |
| | 200 | 67 | 47 |
| | 300 | 80 | 70 |
| | 400 | 92 | 77 |
| 22-15 | 100 | 20 | 30 |
| | 200 | 68 | 40 |
| | 300 | 83 | 75 |
| | 400 | 90 | 72 |
| 22-16 | 100 | 30 | 25 |
| | 200 | 62 | 43 |
| | 300 | 73 | 73 |
| | 400 | 77 | 70 |
| 22-17 | 100 | 30 | 23 |
| | 200 | 58 | 40 |
| | 300 | 75 | 60 |
| | 400 | 80 | 73 |

In this study, isopropyl myristate (composition 22-01) was the most effective of the fatty acid esters tested as additives to oleth-20 (22-10) in glyphosate compositions.

Example 23

Aqueous concentrate compositions were prepared containing glyphosate IPA salt and excipient ingredients as shown in Table 23a. Concentrate composition 23-01 to 23-13 are oil-in-water emulsions and were prepared by process (vii). Concentrate compositions 23-14 to 23-17 are aqueous solution concentrates and were prepared by process (viii).

TABLE 23a

| Concentrate composition | Glyphosate g a.e./l | % w/w Oil | Surfactant | Type of oil | Type of surfactant |
|---|---|---|---|---|---|
| 23-01 | 163 | 0.25 | 2.5 | butyl stearate | laureth-23 |
| 23-02 | 163 | 0.25 | 2.5 | butyl stearate | steareth-20 |
| 23-03 | 163 | 0.25 | 2.5 | butyl stearate | ceteareth-20 |
| 23-04 | 163 | 0.25 | 2.5 | butyl stearate | ceteareth-15 |
| 23-05 | 163 | 0.25 | 2.5 | butyl stearate | Neodol 45-13 |
| 23-06 | 163 | 0.25 | 2.5 | methyl stearate | steareth-20 |
| 23-07 | 163 | 0.25 | 2.5 | methyl stearate | ceteareth-20 |
| 23-08 | 163 | 0.25 | 2.5 | methyl stearate | ceteareth-15 |
| 23-09 | 163 | 0.25 | 2.5 | methyl stearate | Neodol 45-13 |
| 23-10 | 163 | 0.25 | 2.5 | methyl palmitate | steareth-20 |
| 23-11 | 163 | 0.25 | 2.5 | methyl palmitate | ceteareth-20 |
| 23-12 | 163 | 0.25 | 2.5 | methyl palmitate | ceteareth-15 |
| 23-13 | 163 | 0.25 | 2.5 | methyl palmitate | Neodol 45-13 |
| 23-14 | 163 | | 2.5 | none | steareth-20 |
| 23-15 | 163 | | 2.5 | none | ceteareth-20 |
| 23-16 | 163 | | 2.5 | none | ceteareth-15 |
| 23-17 | 163 | | 2.5 | none | Neodol 45-13 |

Velvetleaf (*Abutilon theophrasti*, ABUTH) and Japanese millet (*Echinochloa crus-galli*, ECHCF) plants were grown and treated by the standard procedures given above. Applications of spray compositions were made 24 days after planting ABUTH and ECHCF, and evaluation of herbicidal inhibition was done 16 days after application.

Formulations B, C and J were applied as comparative treatments. Results, averaged for all replicates of each treatment, are shown in Table 23b.

TABLE 23b

| Concentrate composition | Glyphosate rate g a.e./ha | % Inhibition ABUTH | ECHCF |
|---|---|---|---|
| Formulation B | 100 | 10 | 37 |
| | 200 | 30 | 40 |
| | 300 | 43 | 57 |
| | 400 | 23 | 33 |
| Formulation C | 100 | 50 | 67 |
| | 200 | 75 | 96 |
| | 300 | 85 | 99 |
| | 400 | 94 | 100 |
| Formulation J | 100 | 40 | 75 |
| | 200 | 73 | 94 |
| | 300 | 93 | 98 |
| | 400 | 95 | 99 |
| 23-01 | 100 | 63 | 77 |
| | 200 | 67 | 94 |
| | 300 | 77 | 99 |
| | 400 | 88 | 96 |
| 23-02 | 100 | 63 | 75 |
| | 200 | 83 | 88 |
| | 300 | 93 | 98 |
| | 400 | 95 | 99 |
| 23-03 | 100 | 67 | 75 |
| | 200 | 82 | 95 |
| | 300 | 95 | 99 |
| | 400 | 98 | 99 |
| 23-04 | 100 | 60 | 75 |
| | 200 | 82 | 97 |
| | 300 | 96 | 99 |
| | 400 | 98 | 100 |

TABLE 23b-continued

| Concentrate composition | Glyphosate rate g a.e./ha | % Inhibition ABUTH | ECHCF |
|---|---|---|---|
| 23-05 | 100 | 63 | 73 |
|  | 200 | 75 | 89 |
|  | 300 | 80 | 98 |
|  | 400 | 87 | 97 |
| 23-06 | 100 | 58 | 63 |
|  | 200 | 78 | 93 |
|  | 300 | 93 | 99 |
|  | 400 | 98 | 100 |
| 23-07 | 100 | 60 | 67 |
|  | 200 | 78 | 93 |
|  | 300 | 93 | 99 |
|  | 400 | 100 | 99 |
| 23-08 | 100 | missing | missing |
|  | 200 | missing | missing |
|  | 300 | 78 | 95 |
|  | 400 | 98 | 99 |
| 23-09 | 100 | 23 | 30 |
|  | 200 | 65 | 83 |
|  | 300 | 80 | 98 |
|  | 400 | 93 | 99 |
| 23-10 | 100 | 65 | 67 |
|  | 200 | 83 | 95 |
|  | 300 | 97 | 99 |
|  | 400 | 99 | 99 |
| 23-11 | 100 | 72 | 73 |
|  | 200 | 90 | 98 |
|  | 300 | 96 | 97 |
|  | 400 | 99 | 99 |
| 23-12 | 100 | 68 | 63 |
|  | 200 | 90 | 92 |
|  | 300 | 98 | 99 |
|  | 400 | 97 | 99 |
| 23-13 | 100 | 43 | 73 |
|  | 200 | 72 | 87 |
|  | 300 | 83 | 98 |
|  | 400 | 93 | 96 |
| 23-14 | 100 | 62 | 77 |
|  | 200 | 78 | 99 |
|  | 300 | 95 | 99 |
|  | 400 | 98 | 100 |
| 23-15 | 100 | 52 | 60 |
|  | 200 | 78 | 93 |
|  | 300 | 94 | 98 |
|  | 400 | 97 | 99 |
| 23-16 | 100 | 38 | 68 |
|  | 200 | 68 | 99 |
|  | 300 | 87 | 97 |
|  | 400 | 94 | 99 |
| 23-17 | 100 | 55 | 75 |
|  | 200 | 68 | 91 |
|  | 300 | 83 | 96 |
|  | 400 | 87 | 98 |

Herbicidal effectiveness exceeding that of commercial standard composition J, at least on ABUTH, was recorded with several compositions, including 23-02 (steareth-20 plus butyl stearate), 23-03 (ceteareth-20 plus butyl stearate), 23-04 (ceteareth-15 plus butyl stearate), 23-10 (steareth-20 plus methyl palmitate), 23-11 (ceteareth-20 plus methyl palmitate) and 23-12 (ceteareth-15 plus methyl palmitate). Compositions lacking fatty acid ester performed slightly less well overall than those containing butyl stearate or methyl palmitate.

Example 24

Spray compositions were prepared containing glyphosate IPA salt and excipient ingredients as shown in Table 24a. Compositions were prepared by simple mixing of ingredients. Soybean lecithin (45% phospholipid, Avanti), where included, was first prepared with sonication in water to make a homogeneous composition. Four different concentrations of glyphosate (not shown in Table 24a) were prepared, calculated to provide, when applied in a spray volume of 93 l/ha, the glyphosate rates shown in Table 24b.

TABLE 24a

| Spray comp. | % w/w Lecithin | FC-754 | Butyl stearate | Methyl oleate | Oleth-20 | Lecithin supplied as | Methyl oleate supplied as |
|---|---|---|---|---|---|---|---|
| 24-01 | 0.05 | 0.050 |  |  |  | soybean lecithin |  |
| 24-02 | 0.05 |  | 0.050 |  |  | soybean lecithin |  |
| 24-03 | 0.05 |  |  |  |  | soybean lecithin |  |
| 24-04 |  | 0.050 |  |  |  |  |  |
| 24-05 |  |  | 0.050 |  |  |  |  |
| 24-06 | 0.05 |  |  |  |  | LI-700 |  |
| 24-07 |  |  | 0.005 |  | 0.05 |  |  |
| 24-08 |  |  |  | 0.01 | 0.05 |  |  |
| 24-09 |  |  |  |  | 0.05 |  |  |
| 24-10 |  |  | 0.005 |  |  |  |  |
| 24-11 |  |  |  | 0.01 |  |  | pure methylated seed oil |
| 24-12 |  |  |  | 0.01 |  |  | pure methylated seed oil |

Velvetleaf (Abutilon theophrasti, ABUTH), Japanese millet (Echinochloa crus-galli, ECHCF) and Prickly sida (Sida spinosa, SIDSP) plants were grown and treated by the standard procedures given above. Applications of spray compositions were made 14 days after planting ABUTH, 14 days after planting ECHCF and 21 days after planting SIDSP. Evaluation of herbicidal inhibition was done 14 days after application.

Formulations B and C were applied as comparative treatments, representing technical glyphosate IPA salt and a commercial formulation of glyphosate IPA salt respectively. Results, averaged for all replicates of each treatment, are shown in Table 24b.

TABLE 24b

| Spray composition | Glyphosate rate g a.e./ha | % Inhibition ABUTH | ECHCF | SIDSP |
|---|---|---|---|---|
| Formulation B | 50 | 0 | 0 | 0 |
|  | 100 | 38 | 35 | 35 |
|  | 200 | 87 | 50 | 90 |
|  | 300 | 95 | 88 | 94 |
| Formulation C | 50 | 0 | 2 | 0 |
|  | 100 | 32 | 55 | 25 |
|  | 200 | 85 | 97 | 93 |
|  | 300 | 96 | 99 | 96 |
| 24-01 | 50 | 78 | 53 | 88 |
|  | 100 | 90 | 60 | 95 |
|  | 200 | 99 | 96 | 99 |
|  | 300 | 99 | 97 | 98 |
| 24-02 | 50 | 25 | 15 | 43 |
|  | 100 | 72 | 30 | 82 |
|  | 200 | 94 | 62 | 93 |
|  | 300 | 95 | 77 | 94 |
| 24-03 | 50 | 20 | 8 | 32 |
|  | 100 | 52 | 22 | 78 |
|  | 200 | 87 | 55 | 91 |
|  | 300 | 95 | 65 | 93 |

TABLE 24b-continued

| Spray composition | Glyphosate rate g a.e./ha | % Inhibition ABUTH | ECHCF | SIDSP |
|---|---|---|---|---|
| 24-04 | 50 | 62 | 37 | 85 |
|  | 100 | 82 | 68 | 92 |
|  | 200 | 97 | 96 | 95 |
|  | 300 | 98 | 95 | 97 |
| 24-05 | 50 | 15 | 10 | 25 |
|  | 100 | 47 | 27 | 23 |
|  | 200 | 85 | 62 | 87 |
|  | 300 | 90 | 63 | 92 |
| 24-06 | 50 | 0 | 2 | 0 |
|  | 100 | 20 | 15 | 20 |
|  | 200 | 85 | 60 | 82 |
|  | 300 | 90 | 65 | 90 |
| 24-07 | 50 | 67 | 27 | 82 |
|  | 100 | 87 | 55 | 93 |
|  | 200 | 94 | 92 | 96 |
|  | 300 | 97 | 99 | 97 |
| 24-08 | 50 | 62 | 30 | 75 |
|  | 100 | 78 | 63 | 91 |
|  | 200 | 93 | 96 | 96 |
|  | 300 | 94 | 98 | 98 |
| 24-09 | 50 | 65 | 45 | 77 |
|  | 100 | 80 | 73 | 95 |
|  | 200 | 93 | 98 | 97 |
|  | 300 | 95 | 99 | 99 |
| 24-10 | 50 | 10 | 25 | 5 |
|  | 100 | 23 | 35 | 37 |
|  | 200 | 90 | 50 | 93 |
|  | 300 | 92 | 73 | 94 |
| 24-11 | 50 | 10 | 25 | 0 |
|  | 100 | 52 | 33 | 43 |
|  | 200 | 88 | 72 | 93 |
|  | 300 | 94 | 78 | 94 |
| 24-12 | 50 | 0 | 15 | 0 |
|  | 100 | 43 | 35 | 33 |
|  | 200 | 91 | 70 | 90 |
|  | 300 | 94 | 82 | 93 |

Results of this test using glyphosate as the exogenous chemical are summarized as follows:

Oleth-20 at the low concentration of 0.05% (24-09) gave extremely high effectiveness, superior to that obtained with the commercial standard. Addition of 0.005% butyl stearate (24-07) or 0.01% methyl oleate (24-08) did not provide further enhancement.

Example 25

Spray compositions were prepared containing paraquat dichloride and excipient ingredients. Compositions 25-01 to 25-12 were exactly like compositions 24-01 to 24-12 except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 8 days after planting ECHCF and 21 days after planting SIDSP. Evaluation of herbicidal inhibition was done 12 days after application.

Standards included technical paraquat dichloride and Gramoxone, a commercial formulation of paraquat from Zeneca. Results, averaged for all replicates of each treatment, are shown in Table 25.

TABLE 25

| Spray composition | Paraquat rate g a.i./ha | % Inhibition ABUTH | ECHCF | SIDSP |
|---|---|---|---|---|
| Paraquat dichloride (technical) | 25 | 50 | 83 | 55 |
|  | 50 | 57 | 78 | 60 |
|  | 100 | 73 | 84 | 69 |
|  | 200 | 85 | 95 | 99 |
| Gramoxone (commercial) | 25 | 40 | 72 | 40 |
|  | 50 | 60 | 70 | 52 |
|  | 100 | 72 | 58 | 55 |
|  | 200 | 72 | 89 | 63 |
| 25-01 | 25 | 75 | 93 | 67 |
|  | 50 | 82 | 97 | 91 |
|  | 100 | 95 | 98 | 97 |
|  | 200 | 100 | 99 | 99 |
| 25-02 | 25 | 67 | 80 | 48 |
|  | 50 | 68 | 87 | 65 |
|  | 100 | 88 | 97 | 93 |
|  | 200 | 96 | 99 | 98 |
| 25-03 | 25 | 55 | 65 | 42 |
|  | 50 | 62 | 87 | 65 |
|  | 100 | 83 | 96 | 93 |
|  | 200 | 95 | 99 | 97 |
| 25-04 | 25 | 53 | 82 | 45 |
|  | 50 | 63 | 94 | 53 |
|  | 100 | 88 | 99 | 86 |
|  | 200 | 92 | 99 | 98 |
| 25-05 | 25 | 58 | 67 | 50 |
|  | 50 | 60 | 62 | 45 |
|  | 100 | 70 | 73 | 62 |
|  | 200 | 85 | 90 | 88 |
| 25-06 | 25 | 53 | 77 | 43 |
|  | 50 | 60 | 92 | 40 |
|  | 100 | 80 | 93 | 55 |
|  | 200 | 96 | 99 | 78 |
| 25-07 | 25 | 65 | 80 | 45 |
|  | 50 | 82 | 92 | 70 |
|  | 100 | 96 | 96 | 89 |
|  | 200 | 100 | 98 | 99 |
| 25-08 | 25 | 67 | 80 | 37 |
|  | 50 | 82 | 90 | 71 |
|  | 100 | 97 | 98 | 65 |
|  | 200 | 99 | 99 | 93 |
| 25-09 | 25 | 72 | 90 | 50 |
|  | 50 | 80 | 97 | 57 |
|  | 100 | 91 | 99 | 94 |
|  | 200 | 97 | 100 | 97 |
| 25-10 | 25 | 67 | 87 | 45 |
|  | 50 | 68 | 75 | 57 |
|  | 100 | 78 | 93 | 63 |
|  | 200 | 82 | 97 | 82 |
| 25-11 | 25 | 65 | 80 | 45 |
|  | 50 | 73 | 77 | 62 |
|  | 100 | 90 | 95 | 62 |
|  | 200 | 94 | 98 | 78 |
| 25-12 | 25 | 67 | 78 | 37 |
|  | 50 | 75 | 90 | 55 |
|  | 100 | 77 | 97 | 90 |
|  | 200 | 85 | 99 | 92 |

Results of this test using paraquat as the exogenous chemical are summarized as follows:

Oleth-20 at the low concentration of 0.05% (25-09) gave extremely high effectiveness, superior to that obtained with the commercial standard. Addition of 0.005% butyl stearate (25-07) or 0.01% methyl oleate (25-08) did not provide further enhancement.

Example 26

Spray compositions were prepared containing acifluorfen sodium salt and excipient ingredients. Compositions 26-01 to 26-12 were exactly like compositions 24-01 to 24-12 respectively except that a different active ingredient was used and a range of active ingredient concentrations was selected appropriate to the active ingredient being applied.

Velvetleaf (*Abutilon theophrasti, ABUTH*), Japanese millet (*Echinochloa crus-galli, ECHCF*) and prickly sida (*Sida spinosa, SIDSP*) plants were grown and treated by the standard procedures given above. Applications of spray compositions were made 15 days after planting *ABUTH*, 9 days after planting *ECHCF* and 22 days after planting *SIDSP*. Evaluation of herbicidal inhibition was done 10 days after application.

Standards included technical acifluorfen sodium and Blazer, a commercial formulation of acifluorfen from Rohm & Haas. Results, averaged for all replicates of each treatment, are shown in Table 26.

TABLE 26

| Spray composition | Acifluorfen rate g a.i./ha | % Inhibition ABUTH | ECHCF | SIDSP |
|---|---|---|---|---|
| Acifluorfen (technical) | 25 | 20 | 2 | 15 |
|  | 50 | 32 | 7 | 17 |
|  | 100 | 52 | 18 | 35 |
|  | 200 | 62 | 35 | 40 |
| Blazer (commercial) | 25 | 30 | 30 | 5 |
|  | 50 | 53 | 53 | 12 |
|  | 100 | 55 | 55 | 7 |
|  | 200 | 65 | 65 | 32 |
| 26-01 | 25 | 60 | 7 | 20 |
|  | 50 | 63 | 20 | 20 |
|  | 100 | 65 | 43 | 33 |
|  | 200 | 80 | 70 | 48 |
| 26-02 | 25 | 25 | 7 | 5 |
|  | 50 | 42 | 12 | 25 |
|  | 100 | 60 | 30 | 22 |
|  | 200 | 68 | 68 | 50 |
| 26-03 | 25 | 22 | 5 | 10 |
|  | 50 | 55 | 7 | 33 |
|  | 100 | 62 | 25 | 27 |
|  | 200 | 65 | 55 | 48 |
| 26-04 | 25 | 57 | 7 | 13 |
|  | 50 | 67 | 10 | 32 |
|  | 100 | 67 | 35 | 32 |
|  | 200 | 70 | 70 | 45 |
| 26-05 | 25 | 30 | 3 | 15 |
|  | 50 | 47 | 27 | 27 |
|  | 100 | 55 | 42 | 37 |
|  | 200 | 65 | 60 | 38 |
| 26-06 | 25 | 28 | 0 | 3 |
|  | 50 | 50 | 0 | 10 |
|  | 100 | 55 | 30 | 25 |
|  | 200 | 67 | 58 | 47 |
| 26-07 | 25 | 35 | 20 | 17 |
|  | 50 | 55 | 35 | 27 |
|  | 100 | 58 | 63 | 32 |
|  | 200 | 67 | 67 | 55 |
| 26-08 | 25 | 40 | 20 | 8 |
|  | 50 | 57 | 30 | 28 |
|  | 100 | 60 | 60 | 30 |
|  | 200 | 70 | 77 | 48 |
| 26-09 | 25 | 47 | 20 | 22 |
|  | 50 | 55 | 35 | 35 |
|  | 100 | 62 | 65 | 38 |
|  | 200 | 68 | 82 | 50 |
| 26-10 | 25 | 28 | 0 | 5 |
|  | 50 | 48 | 0 | 10 |
|  | 100 | 53 | 5 | 25 |
|  | 200 | 62 | 35 | 40 |
| 26-11 | 25 | 35 | 0 | 5 |
|  | 50 | 43 | 0 | 30 |
|  | 100 | 50 | 0 | 35 |
|  | 200 | 65 | 43 | 47 |

TABLE 26-continued

| Spray composition | Acifluorfen rate g a.i./ha | % Inhibition ABUTH | ECHCF | SIDSP |
|---|---|---|---|---|
| 26-12 | 25 | 40 | 5 | 5 |
|  | 50 | 55 | 18 | 35 |
|  | 100 | 60 | 47 | 38 |
|  | 200 | 70 | 62 | 48 |

Results of this test using acifluorfen as the exogenous chemical are summarized as follows:

Oleth-20 at the low concentration of 0.05% (26-09) gave effectiveness superior to that obtained with the commercial standard. Addition of 0.005% butyl stearate (26-07) or 0.01% methyl oleate (26-08) did not provide further enhancement.

Example 27

Spray compositions were prepared containing asulam and excipient ingredients. Compositions 27-01 to 27-12 were exactly like compositions 24-01 to 24-12 respectively except that a different active ingredient was used and a range of active ingredient concentrations was selected appropriate to the active ingredient being applied.

Velvetleaf (*Abutilon theophrasti, ABUTH*), Japanese millet (*Echinochloa crus-galli, ECHCF*) and prickly sida (*Sida spinosa, SIDSP*) plants were grown and treated by the standard procedures given above. Applications of spray compositions were made 14 days after planting *ABUTH*, 11 days after planting *ECHCF* and 21 days after planting *SIDSP*. Evaluation of herbicidal inhibition was done 14 days after application.

Standards included technical asulam and Asulox, a commercial formulation of asulam from Rhône-Poulenc. Results, averaged for all replicates of each treatment, are shown in Table 27.

TABLE 27

| Spray composition | Asulam rate g a.i./ha | % Inhibition ABUTH | ECHCF | SIDSP |
|---|---|---|---|---|
| Asulam (technical) | 200 | 0 | 12 | 0 |
|  | 400 | 17 | 27 | 5 |
|  | 800 | 48 | 32 | 20 |
|  | 1400 | 42 | 50 | 37 |
| Asulox (commercial) | 200 | 3 | 5 | 0 |
|  | 400 | 27 | 30 | 20 |
|  | 800 | 52 | 45 | 25 |
|  | 1400 | 50 | 60 | 40 |
| 27-01 | 200 | 5 | 8 | 13 |
|  | 400 | 23 | 45 | 22 |
|  | 800 | 50 | 50 | 30 |
|  | 1400 | 60 | 65 | 48 |
| 27-02 | 200 | 0 | 20 | 17 |
|  | 400 | 33 | 40 | 20 |
|  | 800 | 47 | 48 | 33 |
|  | 1400 | 53 | 68 | 55 |
| 27-03 | 200 | 3 | 20 | 3 |
|  | 400 | 28 | 52 | 7 |
|  | 800 | 50 | 50 | 23 |
|  | 1400 | 50 | 58 | 43 |

TABLE 27-continued

| Spray composition | Asulam rate g a.i./ha | % Inhibition ABUTH | ECHCF | SIDSP |
|---|---|---|---|---|
| 27-04 | 200 | 3 | 40 | 7 |
| | 400 | 35 | 45 | 18 |
| | 800 | 52 | 50 | 25 |
| | 1400 | 58 | 60 | 42 |
| 27-05 | 200 | 0 | 10 | 3 |
| | 400 | 23 | 30 | 18 |
| | 800 | 33 | 50 | 32 |
| | 1400 | 45 | 57 | 38 |
| 27-06 | 200 | 2 | 30 | 10 |
| | 400 | 8 | 47 | 17 |
| | 800 | 50 | 55 | 28 |
| | 1400 | 52 | 63 | 40 |
| 27-07 | 200 | 0 | 43 | 3 |
| | 400 | 22 | 48 | 17 |
| | 800 | 40 | 55 | 28 |
| | 1400 | 52 | 60 | 33 |
| 27-08 | 200 | 7 | 47 | 22 |
| | 400 | 20 | 48 | 22 |
| | 800 | 53 | 55 | 30 |
| | 1400 | 57 | 60 | 33 |
| 27-09 | 200 | 0 | 45 | 7 |
| | 400 | 25 | 50 | 7 |
| | 800 | 53 | 60 | 32 |
| | 1400 | 55 | 63 | 37 |
| 27-10 | 200 | 22 | 37 | 10 |
| | 400 | 27 | 45 | 10 |
| | 800 | 50 | 43 | 23 |
| | 1400 | 52 | 52 | 27 |
| 27-11 | 200 | 25 | 33 | 5 |
| | 400 | 15 | 37 | 13 |
| | 800 | 48 | 42 | 25 |
| | 1400 | 42 | 52 | 28 |
| 27-12 | 200 | 3 | 25 | 17 |
| | 400 | 13 | 42 | 18 |
| | 800 | 50 | 45 | 30 |
| | 1400 | 52 | 50 | 33 |

Results of this test using asulam as the exogenous chemical are summarized as follows:

Oleth-20 at the low concentration of 0.05% (27-09) gave, at low exogenous chemical rates, effectiveness on ECHCF superior to that obtained with the commercial standard. Addition of 0.005% butyl stearate (27-07) or 0.01% methyl oleate (27-08) did not provide further enhancement.

Example 28

Spray compositions were prepared containing dicamba sodium salt and excipient ingredients. Compositions 28-01 to 28-12 were exactly like compositions 24-01 to 24-12 respectively except that a different active ingredient was used and a range of active ingredient concentrations was selected appropriate to the active ingredient being applied.

Velvetleaf (Abutilon theophrasti, ABUTH), Japanese millet (Echinochloa crus-galli, ECHCF) and prickly sida (Sida spinosa, SIDSP) plants were grown and treated by the standard procedures given above. Applications of spray compositions were made 14 days after planting ABUTH, 8 days after planting ECHCF and 21 days after planting SIDSP. Evaluation of herbicidal inhibition was done 17 days after application.

Standards included technical dicamba sodium and Banvel, a commercial formulation of dicamba from Sandoz. Results, averaged for all replicates of each treatment, are shown in Table 28.

TABLE 28

| Spray composition | Dicamba rate g a.i./ha | % Inhibition ABUTH | ECHCF | SIDSP |
|---|---|---|---|---|
| Dicamba | 25 | 47 | 0 | 30 |
| (technical) | 50 | 63 | 0 | 40 |
| | 100 | 82 | 0 | 50 |
| | 200 | 93 | 5 | 58 |
| Banvel | 25 | 47 | 0 | 35 |
| (commercial) | 50 | 68 | 0 | 40 |
| | 100 | 91 | 0 | 53 |
| | 200 | 93 | 3 | 63 |
| 28-01 | 25 | 42 | 0 | 38 |
| | 50 | 67 | 0 | 48 |
| | 100 | 92 | 0 | 67 |
| | 200 | 93 | 3 | 73 |
| 28-02 | 25 | 43 | 0 | 43 |
| | 50 | 58 | 0 | 50 |
| | 100 | 85 | 0 | 62 |
| | 200 | 89 | 8 | 72 |
| 28-03 | 25 | 50 | 0 | 32 |
| | 50 | 65 | 0 | 45 |
| | 100 | 90 | 0 | 60 |
| | 200 | 94 | 13 | 68 |
| 28-04 | 25 | 43 | 0 | 35 |
| | 50 | 65 | 0 | 42 |
| | 100 | 94 | 0 | 53 |
| | 200 | 94 | 13 | 67 |
| 28-05 | 25 | 50 | 0 | 35 |
| | 50 | 68 | 0 | 40 |
| | 100 | 88 | 0 | 53 |
| | 200 | 92 | 15 | 60 |
| 28-06 | 25 | 40 | 0 | 40 |
| | 50 | 65 | 0 | 45 |
| | 100 | 88 | 0 | 52 |
| | 200 | 92 | 8 | 70 |
| 28-07 | 25 | 45 | 0 | 42 |
| | 50 | 57 | 0 | 45 |
| | 100 | 88 | 0 | 62 |
| | 200 | 88 | 20 | 68 |
| 28-08 | 25 | 40 | 0 | 38 |
| | 50 | 62 | 0 | 45 |
| | 100 | 97 | 18 | 62 |
| | 200 | 93 | 17 | 73 |
| 28-09 | 25 | 33 | 0 | 35 |
| | 50 | 60 | 0 | 45 |
| | 100 | 93 | 0 | 63 |
| | 200 | 96 | 15 | 73 |
| 28-10 | 25 | 35 | 0 | 30 |
| | 50 | 57 | 0 | 43 |
| | 100 | 90 | 0 | 50 |
| | 200 | 90 | 3 | 70 |
| 28-11 | 25 | 45 | 0 | 30 |
| | 50 | 53 | 0 | 42 |
| | 100 | 89 | 0 | 55 |
| | 200 | 92 | 0 | 73 |
| 28-12 | 25 | 38 | 0 | 37 |
| | 50 | 60 | 0 | 45 |
| | 100 | 96 | 0 | 52 |
| | 200 | 93 | 0 | 70 |

Results of this test using dicamba as the exogenous chemical are summarized as follows:

Oleth-20 at the low concentration of 0.05% (28-09) gave effectiveness on SIDSP superior to that obtained with the commercial standard. Addition of 0.005% butyl stearate (28-07) or 0.01% methyl oleate (28-08) did not provide significant further enhancement.

Example 29

Spray compositions were prepared containing metsulfuron-methyl and excipient ingredients. Compositions 29-01 to 29-12 were exactly like compositions 24-01 to 24-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 8 days after planting ECHCF and 21 days after planting SIDSP. Evaluation of herbicidal inhibition was done 14 days after application.

Standards included technical metsulfuron-methyl and Ally, a commercial formulation of metsulfuron from Du Pont. Results, averaged for all replicates of each treatment, are shown in Table 29.

TABLE 29

| Spray composition | Metsulfuron rate g a.i./ha | % Inhibition ABUTH | ECHCF | SIDSP |
|---|---|---|---|---|
| Metsulfuron (technical) | 0.5 | 72 | 0 | 5 |
|  | 1 | 90 | 0 | 23 |
|  | 5 | 96 | 0 | 50 |
|  | 10 | 97 | 30 | 55 |
| Ally (commercial) | 0.5 | 75 | 0 | 5 |
|  | 1 | 85 | 0 | 22 |
|  | 5 | 95 | 0 | 42 |
|  | 10 | 97 | 25 | 53 |
| 29-01 | 0.5 | 95 | 0 | 47 |
|  | 1 | 96 | 20 | 53 |
|  | 5 | 97 | 25 | 62 |
|  | 10 | 98 | 45 | 62 |
| 29-02 | 0.5 | 87 | 0 | 40 |
|  | 1 | 90 | 10 | 55 |
|  | 5 | 95 | 10 | 58 |
|  | 10 | 96 | 40 | 63 |
| 29-03 | 0.5 | 87 | 0 | 27 |
|  | 1 | 90 | 0 | 40 |
|  | 5 | 96 | 10 | 57 |
|  | 10 | 97 | 33 | 63 |
| 29-04 | 0.5 | 90 | 0 | 33 |
|  | 1 | 95 | 10 | 50 |
|  | 5 | 98 | 17 | 62 |
|  | 10 | 99 | 28 | 58 |
| 29-05 | 0.5 | 85 | 0 | 27 |
|  | 1 | 90 | 0 | 33 |
|  | 5 | 95 | 0 | 47 |
|  | 10 | 95 | 13 | 60 |
| 29-06 | 0.5 | 77 | 0 | 30 |
|  | 1 | 89 | 10 | 47 |
|  | 5 | 96 | 17 | 62 |
|  | 10 | 98 | 33 | 60 |
| 29-07 | 0.5 | 94 | 0 | 55 |
|  | 1 | 97 | 10 | 60 |
|  | 5 | 98 | 43 | 60 |
|  | 10 | 97 | 55 | 65 |
| 29-08 | 0.5 | 93 | 0 | 55 |
|  | 1 | 96 | 5 | 58 |
|  | 5 | 97 | 42 | 60 |
|  | 10 | 97 | 50 | 60 |
| 29-09 | 0.5 | 93 | 0 | 55 |
|  | 1 | 97 | 10 | 62 |
|  | 5 | 98 | 55 | 62 |
|  | 10 | 98 | 65 | 63 |
| 29-10 | 0.5 | 85 | 0 | 28 |
|  | 1 | 82 | 0 | 30 |
|  | 5 | 95 | 10 | 52 |
|  | 10 | 96 | 17 | 57 |
| 29-11 | 0.5 | 73 | 0 | 25 |
|  | 1 | 88 | 20 | 28 |
|  | 5 | 94 | 25 | 53 |
|  | 10 | 96 | 32 | 57 |

TABLE 29-continued

| Spray composition | Metsulfuron rate g a.i./ha | % Inhibition ABUTH | ECHCF | SIDSP |
|---|---|---|---|---|
| 29-12 | 0.5 | 75 | 0 | 32 |
|  | 1 | 85 | 20 | 37 |
|  | 5 | 94 | 23 | 55 |
|  | 10 | 96 | 25 | 57 |

Results of this test using metsulfuron as the exogenous chemical are summarized as follows:

Oleth-20 at the low concentration of 0.05% (29-09) gave high effectiveness, superior to that obtained with the commercial standard. Addition of 0.005% butyl stearate (29-07) or 0.01% methyl oleate (29-08) did not provide further enhancement.

Example 30

Spray compositions were prepared containing imazethapyr and excipient ingredients. Compositions 30-01 to 30-12 were exactly like compositions 24-01 to 24-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 14 days after planting ECHCF and 21 days after planting SIDSP. Evaluation of herbicidal inhibition was done 14 days after application.

Standards included technical imazethapyr and Pursuit, a commercial formulation of imazethapyr from American Cyanamid. Results, averaged for all replicates of each treatment, are shown in Table 30.

TABLE 30

| Spray composition | Imazethapyr rate g a.i./ha | % Inhibition ABUTH | ECHCF | SIDSP |
|---|---|---|---|---|
| Imazethapyr (technical) | 5 | 78 | 5 | 20 |
|  | 10 | 83 | 20 | 30 |
|  | 25 | 93 | 35 | 40 |
|  | 50 | 94 | 53 | 50 |
| Pursuit (commercial) | 5 | 70 | 5 | 25 |
|  | 10 | 73 | 33 | 30 |
|  | 25 | 90 | 50 | 42 |
|  | 50 | 93 | 62 | 57 |
| 30-01 | 5 | 70 | 45 | 35 |
|  | 10 | 75 | 62 | 52 |
|  | 25 | 92 | 63 | 57 |
|  | 50 | 93 | 72 | 62 |
| 30-02 | 5 | 73 | 57 | 32 |
|  | 10 | 75 | 67 | 43 |
|  | 25 | 90 | 70 | 52 |
|  | 50 | 92 | 72 | 57 |
| 30-03 | 5 | 70 | 42 | 27 |
|  | 10 | 78 | 42 | 35 |
|  | 25 | 90 | 53 | 45 |
|  | 50 | 92 | 62 | 52 |

TABLE 30-continued

| Spray composition | Imazethapyr rate g a.i./ha | % Inhibition | | |
|---|---|---|---|---|
| | | ABUTH | ECHCF | SIDSP |
| 30-04 | 5 | 73 | 55 | 33 |
| | 10 | 77 | 68 | 45 |
| | 25 | 93 | 68 | 47 |
| | 50 | 94 | 68 | 60 |
| 30-05 | 5 | 73 | 47 | 32 |
| | 10 | 73 | 45 | 40 |
| | 25 | 90 | 62 | 47 |
| | 50 | 91 | 68 | 52 |
| 30-06 | 5 | 78 | 72 | 30 |
| | 10 | 83 | 70 | 35 |
| | 25 | 93 | 77 | 62 |
| | 50 | 94 | 78 | 58 |
| 30-07 | 5 | 82 | 75 | 38 |
| | 10 | 90 | 90 | 52 |
| | 25 | 93 | 93 | 53 |
| | 50 | 97 | 97 | 62 |
| 30-08 | 5 | 75 | 77 | 38 |
| | 10 | 90 | 92 | 50 |
| | 25 | 95 | 93 | 57 |
| | 50 | 97 | 99 | 63 |
| 30-09 | 5 | 78 | 80 | 40 |
| | 10 | 83 | 89 | 63 |
| | 25 | 93 | 93 | 62 |
| | 50 | 96 | 93 | 60 |
| 30-10 | 5 | 85 | 50 | 37 |
| | 10 | 77 | 50 | 45 |
| | 25 | 91 | 63 | 48 |
| | 50 | 93 | 75 | 57 |
| 30-11 | 5 | 75 | 38 | 43 |
| | 10 | 80 | 38 | 37 |
| | 25 | 92 | 62 | 45 |
| | 50 | 93 | 73 | 53 |
| 30-12 | 5 | 75 | 55 | 38 |
| | 10 | 83 | 60 | 43 |
| | 25 | 92 | 67 | 53 |
| | 50 | 93 | 77 | 55 |

Results of this test using imazethapyr as the exogenous chemical are summarized as follows:

Oleth-20 at the low concentration of 0.05% (30-09) gave extremely high effectiveness, greatly superior to that obtained with the commercial standard, especially on ECHCF. Addition of 0.005% butyl stearate (30-07) further enhanced performance of low exogenous chemical rates on ABUTH more effectively than addition of 0.01% methyl oleate (30-08).

Example 31

Spray compositions were prepared containing fluazifop-p-butyl salt and excipient ingredients. Compositions 31-01 to 31-12 were exactly like compositions 24-01 to 24-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and broadleaf signalgrass (*Brachiaria platyphylla*, BRAPP) plants were grown and treated by the standard procedures given above. Applications of spray compositions were made 15 days after planting ABUTH, 15 days after planting ECHCF and 16 days after planting BRAPP. Evaluation of herbicidal inhibition was done 10 days after application.

Standards included technical fluazifop-p-butyl and Fusilade 5, a commercial formulation of fluazifop-p-butyl from Zeneca. Results, averaged for all replicates of each treatment, are shown in Table 31.

TABLE 31

| Spray composition | Fluazifop-p rate g a.i./ha | % Inhibition | | |
|---|---|---|---|---|
| | | ABUTH | ECHCF | BRAPP |
| Fluazifop-p-butyl (technical) | 2 | 0 | 0 | 20 |
| | 5 | 0 | 3 | 35 |
| | 15 | 5 | 45 | 65 |
| | 30 | 5 | 57 | 78 |
| Fusilade 5 (commercial) | 2 | 0 | 0 | 27 |
| | 5 | 0 | 27 | 33 |
| | 15 | 5 | 52 | 78 |
| | 30 | 7 | 75 | 85 |
| 31-01 | 2 | 0 | 0 | 20 |
| | 5 | 2 | 27 | 30 |
| | 15 | 5 | 58 | 78 |
| | 30 | 10 | 87 | 83 |
| 31-02 | 2 | 0 | 7 | 25 |
| | 5 | 0 | 35 | 30 |
| | 15 | 2 | 58 | 75 |
| | 30 | 8 | 78 | 75 |
| 31-03 | 2 | 0 | 0 | 18 |
| | 5 | 0 | 8 | 27 |
| | 15 | 0 | 45 | 75 |
| | 30 | 0 | 55 | 75 |
| 31-04 | 2 | 0 | 20 | 32 |
| | 5 | 2 | 42 | 25 |
| | 15 | 2 | 55 | 72 |
| | 30 | 5 | 80 | 78 |
| 31-05 | 2 | 0 | 13 | 32 |
| | 5 | 2 | 42 | 32 |
| | 15 | 2 | 55 | 72 |
| | 30 | 7 | 58 | 73 |
| 31-06 | 2 | 2 | 17 | 23 |
| | 5 | 0 | 20 | 25 |
| | 15 | 0 | 50 | 75 |
| | 30 | 0 | 73 | 77 |
| 31-07 | 2 | 0 | 50 | 40 |
| | 5 | 0 | 52 | 60 |
| | 15 | 0 | 67 | 80 |
| | 30 | 0 | 92 | 85 |
| 31-08 | 2 | 0 | 43 | 35 |
| | 5 | 0 | 55 | 37 |
| | 15 | 7 | 88 | 82 |
| | 30 | 3 | 96 | 85 |
| 31-09 | 2 | 0 | 47 | 18 |
| | 5 | 0 | 50 | 35 |
| | 15 | 0 | 80 | 80 |
| | 30 | 3 | 93 | 85 |
| 31-10 | 2 | 0 | 23 | 10 |
| | 5 | 0 | 37 | 42 |
| | 15 | 5 | 55 | 75 |
| | 30 | 10 | 58 | 80 |
| 31-11 | 2 | 0 | 7 | 10 |
| | 5 | 0 | 30 | 28 |
| | 15 | 0 | 50 | 62 |
| | 30 | 12 | 53 | 68 |
| 31-12 | 2 | 0 | 5 | 20 |
| | 5 | 0 | 7 | 35 |
| | 15 | 5 | 48 | 68 |
| | 30 | 12 | 60 | 77 |

Results of this test using fluazifop-p-butyl as the exogenous chemical are summarized as follows:

Oleth-20 at the low concentration of 0.05% (31-09) gave extremely high effectiveness on ECHCF, superior to that obtained with the commercial standard. Addition of 0.005% butyl stearate (31-07) or 0.01% methyl oleate (31-08) did not provide significant further enhancement.

Example 32

Spray compositions were prepared containing alachlor and excipient ingredients. Compositions 32-01 to 32-12 were exactly like compositions 24-01 to 24-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 8 days after planting ECHCF and 14 days after planting SIDSP. Evaluation of herbicidal inhibition was done 9 days after application.

Standards included technical alachlor and Lasso, a commercial formulation of alachlor from Monsanto Company. Results, averaged for all replicates of each treatment, are shown in Table 32.

TABLE 32

| Spray composition | Alachlor rate g a.i./ha | % Inhibition ABUTH | ECHCF | SIDSP |
|---|---|---|---|---|
| Alachlor (technical) | 500 | 0 | 0 | 0 |
| | 1000 | 0 | 0 | 0 |
| | 2000 | 0 | 0 | 0 |
| | 4000 | 0 | 0 | 0 |
| Lasso (commercial) | 500 | 0 | 0 | 0 |
| | 1000 | 0 | 5 | 13 |
| | 2000 | 0 | 30 | 17 |
| | 4000 | 15 | 43 | 65 |
| 32-01 | 500 | 0 | 0 | 0 |
| | 1000 | 0 | 0 | 0 |
| | 2000 | 0 | 0 | 0 |
| | 4000 | 10 | 0 | 7 |
| 32-02 | 500 | 0 | 0 | 0 |
| | 1000 | 0 | 0 | 0 |
| | 2000 | 0 | 22 | 7 |
| | 4000 | 12 | 47 | 12 |
| 32-03 | 500 | 0 | 0 | 0 |
| | 1000 | 0 | 0 | 0 |
| | 2000 | 0 | 0 | 0 |
| | 4000 | 10 | 0 | 0 |
| 32-04 | 500 | 0 | 0 | 0 |
| | 1000 | 0 | 0 | 0 |
| | 2000 | 0 | 0 | 0 |
| | 4000 | 5 | 0 | 15 |
| 32-05 | 500 | 0 | 0 | 0 |
| | 1000 | 0 | 0 | 0 |
| | 2000 | 0 | 0 | 0 |
| | 4000 | 3 | 0 | 5 |
| 32-06 | 500 | 0 | 0 | 0 |
| | 1000 | 0 | 0 | 0 |
| | 2000 | 0 | 13 | 7 |
| | 4000 | 0 | 37 | 12 |
| 32-07 | 500 | 0 | 0 | 0 |
| | 1000 | 0 | 8 | 0 |
| | 2000 | 0 | 28 | 15 |
| | 4000 | 12 | 50 | 20 |
| 32-08 | 500 | 0 | 0 | 0 |
| | 1000 | 0 | 8 | 0 |
| | 2000 | 0 | 8 | 0 |
| | 4000 | 5 | 20 | 5 |
| 32-09 | 500 | 0 | 0 | 0 |
| | 1000 | 0 | 0 | 0 |
| | 2000 | 0 | 3 | 0 |
| | 4000 | 12 | 42 | 32 |
| 32-10 | 500 | 0 | 0 | 0 |
| | 1000 | 0 | 0 | 0 |
| | 2000 | 0 | 0 | 0 |
| | 4000 | 0 | 0 | 0 |
| 32-11 | 500 | 0 | 0 | 0 |
| | 1000 | 0 | 0 | 0 |
| | 2000 | 0 | 0 | 0 |
| | 4000 | 0 | 0 | 0 |

TABLE 32-continued

| Spray composition | Alachlor rate g a.i./ha | % Inhibition ABUTH | ECHCF | SIDSP |
|---|---|---|---|---|
| 32-12 | 500 | 0 | 0 | 0 |
| | 1000 | 0 | 0 | 0 |
| | 2000 | 0 | 0 | 0 |
| | 4000 | 0 | 0 | 0 |

None of the compositions tested enhanced post-emergence foliar-applied herbicidal effectiveness of alachlor in this test. Alachlor is not known as a foliar-applied herbicide.

Example 33

Spray compositions were prepared containing glufosinate ammonium salt and excipient ingredients. Compositions 33-01 to 33-12 were exactly like compositions 24-01 to 24-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 10 days after planting ECHCF and 17 days after planting SIDSP. Evaluation of herbicidal inhibition was done 11 days after application.

Standards included technical glufosinate ammonium and Liberty, a commercial formulation of glufosinate from AgrEvo. Results, averaged for all replicates of each treatment, are shown in Table 33.

TABLE 33

| Spray composition | Glufosinate rate g a.i./ha | % Inhibition ABUTH | ECHCF | SIDSP |
|---|---|---|---|---|
| Glufosinate (technical) | 50 | 0 | 0 | 5 |
| | 100 | 47 | 0 | 10 |
| | 300 | 90 | 23 | 96 |
| | 600 | 98 | 43 | 94 |
| Liberty (commercial) | 50 | 77 | 70 | 20 |
| | 100 | 88 | 96 | 93 |
| | 300 | 98 | 100 | 97 |
| | 600 | 99 | 100 | 99 |
| 33-01 | 50 | 77 | 33 | 70 |
| | 100 | 95 | 58 | 93 |
| | 300 | 98 | 95 | 97 |
| | 600 | 99 | 99 | 98 |
| 33-02 | 50 | 33 | 30 | 50 |
| | 100 | 63 | 32 | 93 |
| | 300 | 96 | 52 | 90 |
| | 600 | 98 | 96 | 97 |
| 33-03 | 50 | 15 | 30 | 38 |
| | 100 | 50 | 33 | 87 |
| | 300 | 92 | 40 | 94 |
| | 600 | 98 | 70 | 98 |
| 33-04 | 50 | 92 | 47 | 50 |
| | 100 | 90 | 53 | 85 |
| | 300 | 98 | 98 | 96 |
| | 600 | 98 | 99 | 98 |

TABLE 33-continued

| Spray composition | Glufosinate rate g a.i./ha | % Inhibition ABUTH | ECHCF | SIDSP |
|---|---|---|---|---|
| 33-05 | 50 | 35 | 20 | 20 |
|  | 100 | 37 | 30 | 20 |
|  | 300 | 97 | 45 | 78 |
|  | 600 | 91 | 53 | 92 |
| 33-06 | 50 | 10 | 0 | 20 |
|  | 100 | 20 | 3 | 20 |
|  | 300 | 89 | 47 | 82 |
|  | 600 | 91 | 94 | 89 |
| 33-07 | 50 | 50 | 35 | 70 |
|  | 100 | 73 | 52 | 80 |
|  | 300 | 95 | 87 | 98 |
|  | 600 | 98 | 98 | 97 |
| 33-08 | 50 | 48 | 30 | 88 |
|  | 100 | 83 | 50 | 93 |
|  | 300 | 98 | 97 | 96 |
|  | 600 | 98 | 99 | 96 |
| 33-09 | 50 | 58 | 35 | 92 |
|  | 100 | 91 | 62 | 93 |
|  | 300 | 98 | 96 | 97 |
|  | 600 | 98 | 99 | 96 |
| 33-10 | 50 | 30 | 30 | 0 |
|  | 100 | 43 | 35 | 10 |
|  | 300 | 96 | 43 | 92 |
|  | 600 | 95 | 70 | 91 |
| 33-11 | 50 | 33 | 35 | 0 |
|  | 100 | 53 | 35 | 7 |
|  | 300 | 96 | 43 | 89 |
|  | 600 | 97 | 88 | 93 |
| 33-12 | 50 | 37 | 5 | 5 |
|  | 100 | 37 | 20 | 10 |
|  | 300 | 95 | 40 | 88 |
|  | 600 | 97 | 85 | 93 |

Results of this test using glufosinate as the exogenous chemical are summarized as follows:

Oleth-20 at the low concentration of 0.05% (33-09) gave extremely high effectiveness, superior on SIDSP to that obtained with the commercial standard. Addition of 0.005% butyl stearate (33-07) or 0.01% methyl oleate (33-08) did not provide further enhancement.

Example 34

Aqueous concentrate compositions were prepared containing glyphosate IPA salt and excipient ingredients as shown in Table 34a. Concentrate compositions 34-01 to 34-12 are aqueous solution concentrates containing colloidal particulates and were prepared by process (ix). Concentrate compositions 34-13 to 34-18 contained colloidal particulates but no surfactant.

The colloidal particulates of this example were in general too large to confer good storage stability to the compositions tested.

TABLE 34a

| Concentrate composition | Glyphosate g a.e./l | % w/w Surfactant | Silica | Type of surfactant | Type of silica |
|---|---|---|---|---|---|
| 34-01 | 488 | 3.0 | 0.8 | steareth-20 | Sident 9 |
| 34-02 | 488 | 3.0 | 0.8 | steareth-20 | Sipernat 22 |
| 34-03 | 488 | 3.0 | 0.8 | steareth-20 | Sipernat 22S |
| 34-04 | 488 | 3.0 | 0.8 | oleth-20 | Sident 9 |
| 34-05 | 488 | 3.0 | 0.8 | oleth-20 | Sipernat 22 |
| 34-06 | 488 | 3.0 | 0.8 | oleth-20 | Sipernat 22S |
| 34-07 | 488 | 3.0 | 1.5 | steareth-20 | Sident 9 |
| 34-08 | 488 | 3.0 | 1.5 | steareth-20 | Sipernat 22 |
| 34-09 | 488 | 3.0 | 1.5 | steareth-20 | Sipernat 22S |
| 34-10 | 488 | 3.0 | 1.5 | oleth-20 | Sident 9 |
| 34-11 | 488 | 3.0 | 1.5 | oleth-20 | Sipernat 22 |
| 34-12 | 488 | 3.0 | 1.5 | oleth-20 | Sipernat 22S |
| 34-13 | 488 |  | 0.8 | none | Sident 9 |
| 34-14 | 488 |  | 1.5 | none | Sipernat 22 |
| 34-15 | 488 |  | 0.8 | none | Sipernat 22S |
| 34-16 | 488 |  | 1.5 | none | Sident 9 |
| 34-17 | 488 |  | 0.8 | none | Sipernat 22 |
| 34-18 | 488 |  | 1.5 | none | Sipernat 22S |

Velvetleaf (*Abutilon theophrasti*, ABUTH) and Japanese millet (*Echinochloa crus-galli*, ECHCF) plants were grown and treated by the standard procedures given above. Applications of spray compositions were made 21 days after planting ABUTH and ECHCF, and evaluation of herbicidal inhibition was done 14 days after application.

Formulations B and J were applied as comparative treatments. Results, averaged for all replicates of each treatment, are shown in Table 34b.

TABLE 34b

| Concentrate composition | Glyphosate rate g a.e./ha | % Inhibition ABUTH | ECHCF |
|---|---|---|---|
| Formulation B | 100 | 3 | 37 |
|  | 200 | 10 | 57 |
|  | 300 | 43 | 87 |
|  | 400 | 57 | 88 |
| Formulation J | 100 | 33 | 80 |
|  | 200 | 72 | 98 |
|  | 300 | 96 | 99 |
|  | 400 | 97 | 99 |
| 34-01 | 100 | 47 | 89 |
|  | 200 | 78 | 97 |
|  | 300 | 87 | 99 |
|  | 400 | 98 | 99 |
| 34-02 | 100 | 37 | 83 |
|  | 200 | 70 | 99 |
|  | 300 | 90 | 99 |
|  | 400 | 95 | 100 |
| 34-03 | 100 | 40 | 89 |
|  | 200 | 70 | 99 |
|  | 300 | 90 | 100 |
|  | 400 | 95 | 100 |
| 34-04 | 100 | 37 | 94 |
|  | 200 | 58 | 98 |
|  | 300 | 87 | 99 |
|  | 400 | 95 | 100 |
| 34-05 | 100 | 30 | 60 |
|  | 200 | 73 | 95 |
|  | 300 | 85 | 99 |
|  | 400 | 97 | 99 |
| 34-06 | 100 | 33 | 67 |
|  | 200 | 70 | 97 |
|  | 300 | 78 | 99 |
|  | 400 | 92 | 100 |
| 34-07 | 100 | 32 | 81 |
|  | 200 | 60 | 99 |
|  | 300 | 83 | 98 |
|  | 400 | 88 | 100 |
| 34-08 | 100 | 40 | 63 |
|  | 200 | 65 | 93 |

TABLE 34b-continued

| Concentrate composition | Glyphosate rate g a.e./ha | % Inhibition ABUTH | ECHCF |
|---|---|---|---|
| | 300 | 90 | 99 |
| | 400 | 90 | 100 |
| 34-09 | 100 | 43 | 70 |
| | 200 | 55 | 98 |
| | 300 | 88 | 99 |
| | 400 | 94 | 100 |
| 34-10 | 100 | 33 | 91 |
| | 200 | 70 | 99 |
| | 300 | 83 | 99 |
| | 400 | 94 | 99 |
| 34-11 | 100 | 20 | 63 |
| | 200 | 70 | 97 |
| | 300 | 92 | 100 |
| | 400 | 94 | 100 |
| 34-12 | 100 | 48 | 67 |
| | 200 | 70 | 93 |
| | 300 | 88 | 98 |
| | 400 | 94 | 100 |
| 34-13 | 100 | 20 | 50 |
| | 200 | 60 | 83 |
| | 300 | 83 | 97 |
| | 400 | 94 | 99 |
| 34-14 | 100 | 43 | 43 |
| | 200 | 67 | 88 |
| | 300 | 83 | 97 |
| | 400 | 91 | 99 |
| 34-15 | 100 | 30 | 50 |
| | 200 | 67 | 73 |
| | 300 | 77 | 96 |
| | 400 | 97 | 96 |
| 34-16 | 100 | 43 | 43 |
| | 200 | 75 | 79 |
| | 300 | 87 | 94 |
| | 400 | 87 | 91 |
| 34-17 | 100 | 40 | 27 |
| | 200 | 68 | 53 |
| | 300 | 87 | 92 |
| | 400 | 93 | 98 |
| 34-18 | 100 | 47 | 10 |
| | 200 | 75 | 37 |
| | 300 | 83 | 63 |
| | 400 | 92 | 88 |

Many of the high-load (488 g a.e./l) glyphosate formulations of this Example exhibited herbicidal effectiveness equal to or greater than that obtained with commercial standard Formulation J, in spite of containing only 3% alkylether surfactant.

Example 35

Aqueous concentrate compositions were prepared containing glyphosate IPA salt and excipient ingredients as shown in Table 35a. Concentrate compositions 35-01 to 35-12 and 35-14 to 35-16 are oil-in-water emulsions and were prepared by process (vii). Concentrate composition 35-13 is an aqueous solution concentrate and was prepared by process (viii).

TABLE 35a

| Concentrate composition | Glyphosate g a.e./l | % w/w Oil | % w/w Surfactant | Type of oil | Type of surfactant |
|---|---|---|---|---|---|
| 35-01 | 163 | 0.5 | 5.0 | butyl stearate | steareth-30 |
| 35-02 | 163 | 0.5 | 5.0 | methyl stearate | steareth-30 |
| 35-03 | 163 | 0.5 | 5.0 | butyl stearate | Neodol 45-13 |
| 35-04 | 163 | 0.5 | 5.0 | methyl stearate | Neodol 45-13 |
| 35-05 | 163 | 0.5 | 5.0 | butyl stearate | ceteareth-15 |
| 35-06 | 163 | 0.5 | 5.0 | methyl stearate | ceteareth-15 |
| 35-07 | 163 | 0.5 | 5.0 | butyl stearate | laureth-23 |
| 35-08 | 163 | 0.5 | 5.0 | butyl stearate | oleth-20 |
| 35-09 | 163 | 0.5 | 5.0 | butyl stearate | steareth-20 |
| 35-10 | 163 | 0.5 | 5.0 | butyl stearate | ceteareth-27 |
| 35-11 | 163 | 0.3 | 5.0 | butyl stearate | ceteareth-27 |
| 35-12 | 163 | 0.3 | 2.5 | butyl stearate | ceteareth-27 |
| 35-13 | 163 | | 5.0 | none | ceteareth-27 |
| 35-14 | 163 | 0.5 | 5.0 | methyl stearate | ceteareth-27 |
| 35-15 | 163 | 0.5 | 5.0 | methyl stearate | steareth-20 |
| 35-16 | 163 | 0.5 | 5.0 | methyl stearate | oleth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 20 days after planting ABUTH and ECHCF, and evaluation of herbicidal inhibition was done 16 days after application.

Formulations B, C and J were applied as comparative treatments. Results, averaged for all replicates of each treatment, are shown in Table 35b.

TABLE 35b

| Concentrate composition | Glyphosate rate g a.e./ha | % Inhibition ABUTH | ECHCF |
|---|---|---|---|
| Formulation B | 100 | 45 | 57 |
| | 200 | 35 | 53 |
| | 300 | 50 | 57 |
| | 400 | 38 | 33 |
| Formulation C | 100 | 70 | 98 |
| | 200 | 90 | 99 |
| | 300 | 97 | 100 |
| | 400 | 100 | 100 |
| Formulation J | 100 | 72 | 88 |
| | 200 | 93 | 99 |
| | 300 | 97 | 99 |
| | 400 | 98 | 99 |
| 35-01 | 100 | 83 | 97 |
| | 200 | 97 | 100 |
| | 300 | 99 | 100 |
| | 400 | 100 | 100 |
| 35-02 | 100 | 80 | 99 |
| | 200 | 96 | 100 |
| | 300 | 99 | 100 |
| | 400 | 99 | 100 |
| 35-03 | 100 | 73 | 98 |
| | 200 | 92 | 100 |
| | 300 | 98 | 99 |
| | 400 | 99 | 100 |
| 35-04 | 100 | 73 | 98 |
| | 200 | 87 | 99 |
| | 300 | 97 | 99 |
| | 400 | 99 | 100 |
| 35-05 | 100 | 80 | 98 |
| | 200 | 87 | 100 |
| | 300 | 98 | 100 |
| | 400 | 100 | 100 |
| 35-06 | 100 | 78 | 97 |
| | 200 | 95 | 98 |
| | 300 | 98 | 100 |
| | 400 | 99 | 100 |

TABLE 35b-continued

| Concentrate composition | Glyphosate rate g a.e./ha | % Inhibition ABUTH | ECHCF |
|---|---|---|---|
| 35-07 | 100 | 78 | 98 |
| | 200 | 88 | 100 |
| | 300 | 96 | 100 |
| | 400 | 98 | 100 |
| 35-08 | 100 | 75 | 98 |
| | 200 | 93 | 99 |
| | 300 | 97 | 99 |
| | 400 | 100 | 99 |
| 35-09 | 100 | 83 | 93 |
| | 200 | 95 | 100 |
| | 300 | 98 | 100 |
| | 400 | 100 | 100 |
| 35-10 | 100 | 80 | 97 |
| | 200 | 95 | 98 |
| | 300 | 98 | 99 |
| | 400 | 100 | 100 |
| 35-11 | 100 | 80 | 97 |
| | 200 | 93 | 99 |
| | 300 | 98 | 100 |
| | 400 | 100 | 99 |
| 35-12 | 100 | 77 | 93 |
| | 200 | 88 | 100 |
| | 300 | 99 | 100 |
| | 400 | 99 | 100 |
| 35-13 | 100 | 80 | 73 |
| | 200 | 95 | 95 |
| | 300 | 99 | 100 |
| | 400 | 100 | 100 |
| 35-14 | 100 | 77 | 94 |
| | 200 | 92 | 99 |
| | 300 | 98 | 100 |
| | 400 | 100 | 99 |
| 35-15 | 100 | 78 | 92 |
| | 200 | 94 | 99 |
| | 300 | 98 | 100 |
| | 400 | 99 | 100 |
| 35-16 | 100 | 77 | 93 |
| | 200 | 90 | 98 |
| | 300 | 98 | 99 |
| | 400 | 99 | 100 |

Extremely high herbicidal effectiveness was provided by ceteareth-27 (composition 35-13); this was further enhanced by addition of a small amount of butyl stearate (35-10, 35-11) or methyl stearate (35-14). Compositions performing better than commercial standard Formulations C and J, at least on *ABUTH*, included those containing steareth-30, steareth-20 or ceteareth-27; in this test oleth-20 was not quite as effective as these saturated alkylethers.

Example 36

Aqueous concentrate compositions were prepared containing glyphosate IPA salt and excipient ingredients as shown in Table 36a. All are oil-in-water emulsions and were prepared by process (vii). Lecithin (45% phospholipid, Avanti) was first dispersed in water using sonication.

TABLE 36a

| Concentrate composition | Glyphosate g a.e./l | % w/w | | | | |
|---|---|---|---|---|---|---|
| | | Lecithin | Butyl stearate | Ethomeen T/25 | Ceteareth-20 | Ceteareth-27 |
| 36-01 | 220 | 0.75 | 0.75 | 1.5 | | |
| 36-02 | 220 | 0.75 | 0.75 | 1.5 | | |
| 36-03 | 220 | 0.75 | 0.75 | 3.0 | | |
| 36-04 | 220 | 0.75 | 7.50 | 1.5 | | |
| 36-05 | 220 | 0.75 | 7.50 | 3.0 | | |
| 36-06 | 220 | 3.75 | 3.75 | 3.0 | | |
| 36-07 | 220 | 1.50 | 1.50 | 3.0 | | |
| 36-08 | 220 | 1.50 | 1.50 | 1.5 | | |
| 36-09 | 220 | 3.75 | 3.75 | 1.5 | 1.5 | |
| 36-10 | 220 | 1.50 | 1.50 | 1.5 | 1.5 | |
| 36-11 | 220 | 3.75 | 7.50 | 1.5 | 1.5 | |
| 36-12 | 220 | 3.75 | 1.50 | 1.5 | 1.5 | |
| 36-13 | 220 | 0.75 | 3.75 | 1.5 | | 1.5 |
| 36-14 | 220 | 0.75 | 7.50 | 1.5 | | 1.5 |
| 36-15 | 220 | 0.75 | 3.75 | 3.0 | | 3.0 |
| 36-16 | 220 | 0.75 | 7.50 | 3.0 | | 3.0 |
| 36-17 | 220 | | 7.50 | 3.0 | | |
| 36-18 | 220 | 0.75 | 7.50 | | | 3.0 |

Velvetleaf (*Abutilon theophrasti*, ABUTH) and Japanese millet (*Echinochloa crus-galli*, ECHCF) plants were grown and treated by the standard procedures given above. Applications of spray compositions were made 23 days after planting *ABUTH* and *ECHCF*, and evaluation of herbicidal inhibition was done 18 days after application.

Formulations B and J were applied as comparative treatments. Results, averaged for all replicates of each treatment, are shown in Table 36b.

TABLE 36b

| Concentrate composition | Glyphosate rate g a.e./ha | % Inhibition ABUTH | ECHCF |
|---|---|---|---|
| Formulation B | 100 | 12 | 62 |
| | 200 | 5 | 55 |
| | 300 | 23 | 63 |
| | 400 | 43 | 78 |
| Formulation J | 100 | 27 | 82 |
| | 200 | 62 | 98 |
| | 300 | 88 | 95 |
| | 400 | 96 | 99 |
| 36-01 | 100 | 13 | 79 |
| | 200 | 68 | 95 |
| | 300 | 82 | 99 |
| | 400 | 95 | 91 |
| 36-02 | 100 | 27 | 82 |
| | 200 | 60 | 97 |
| | 300 | 81 | 95 |
| | 400 | 87 | 99 |
| 36-03 | 100 | 37 | 77 |
| | 200 | 62 | 96 |
| | 300 | 78 | 98 |
| | 400 | 89 | 90 |
| 36-04 | 100 | 37 | 84 |
| | 200 | 57 | 95 |
| | 300 | 84 | 99 |
| | 400 | 89 | 100 |
| 36-05 | 100 | 33 | 77 |
| | 200 | 65 | 100 |
| | 300 | 78 | 97 |
| | 400 | 88 | 97 |
| 36-06 | 100 | 43 | 78 |
| | 200 | 62 | 95 |
| | 300 | 87 | 97 |
| | 400 | 95 | 96 |
| 36-07 | 100 | 48 | 78 |
| | 200 | 80 | 91 |

TABLE 36b-continued

| Concentrate composition | Glyphosate rate g a.e./ha | % Inhibition ABUTH | % Inhibition ECHCF |
|---|---|---|---|
| | 300 | 90 | 99 |
| | 400 | 76 | 93 |
| 36-08 | 100 | 48 | 83 |
| | 200 | 67 | 89 |
| | 300 | 86 | 96 |
| | 400 | 93 | 97 |
| 36-09 | 100 | 62 | 84 |
| | 200 | 82 | 98 |
| | 300 | 85 | 99 |
| | 400 | 91 | 97 |
| 36-10 | 100 | 63 | 80 |
| | 200 | 75 | 96 |
| | 300 | 85 | 99 |
| | 400 | 99 | 99 |
| 36-11 | 100 | 42 | 75 |
| | 200 | 78 | 98 |
| | 300 | 92 | 99 |
| | 400 | 93 | 100 |
| 36-12 | 100 | 52 | 80 |
| | 200 | 73 | 93 |
| | 300 | 86 | 99 |
| | 400 | 97 | 97 |
| 36-13 | 100 | 55 | 83 |
| | 200 | 75 | 97 |
| | 300 | 97 | 99 |
| | 400 | 92 | 99 |
| 36-14 | 100 | 52 | 87 |
| | 200 | 73 | 95 |
| | 300 | 91 | 97 |
| | 400 | 87 | 98 |
| 36-15 | 100 | 57 | 83 |
| | 200 | 92 | 96 |
| | 300 | 98 | 100 |
| | 400 | 100 | 98 |
| 36-16 | 100 | 79 | 88 |
| | 200 | 87 | 97 |
| | 300 | 99 | 99 |
| | 400 | 97 | 94 |
| 36-17 | 100 | 58 | 83 |
| | 200 | 47 | 94 |
| | 300 | 88 | 98 |
| | 400 | 91 | 93 |
| 36-18 | 100 | 58 | 87 |
| | 200 | 75 | 91 |
| | 300 | 83 | 99 |
| | 400 | 91 | 98 |

Outstanding herbicidal effectiveness was provided by composition 93-18, containing lecithin, ceteareth-27 and butyl stearate. Addition of 3% Ethomeen T/25 (36-16) further enhanced effectiveness. Slightly reduced effectiveness at the lowest glyphosate rate was observed on *ABUTH* when the butyl stearate concentration was cut in half (36-15).

Example 37

Aqueous concentrate compositions were prepared containing glyphosate IPA salt and excipient ingredients as shown in Table 37a. Concentrate compositions 37-01 to 37-04, 37-06, 37-08, 37-10 and 37-18 are oil-in-water emulsions and were prepared by process (vii). Concentrate compositions 37-05, 37-07 and 37-09 are aqueous solution concentrates and were prepared by process (viii). Concentrate compositions 37-11 to 37-17 contain colloidal particulates and were prepared by process (ix).

The compositions of this example all showed acceptable storage stability. The compositions shown as containing colloidal particulate were not storage-stable unless the colloidal particulate was included as shown.

TABLE 37a

| Concentrate composition | Glyphosate g a.e./l | Butyl stearate % w/w | Surfactant % w/w | Aerosil 380 % w/w | Type of surfactant |
|---|---|---|---|---|---|
| 37-01 | 163 | 0.5 | 5.0 | | steareth-20 |
| 37-02 | 163 | 0.5 | 5.0 | | ceteareth-27 |
| 37-03 | 163 | 0.5 | 5.0 | | oleth-20 |
| 37-04 | 163 | 0.5 | 5.0 | | ceteth-20 |
| 37-05 | 163 | | 5.0 | | ceteth-20 |
| 37-06 | 163 | 0.5 | 5.0 | | Neodol 45-13 |
| 37-07 | 163 | | 5.0 | | Neodol 45-13 |
| 37-08 | 163 | 0.5 | 5.0 | | ceteareth-15 |
| 37-09 | 163 | | 5.0 | | ceteareth-15 |
| 37-10 | 163 | 0.5 | 5.0 | | steareth-30 |
| 37-11 | 360 | 1.0 | 10.0 | 1.25 | ceteth-20 |
| 37-12 | 360 | 1.0 | 10.0 | 1.25 | Neodol 45-13 |
| 37-13 | 360 | 1.0 | 10.0 | 1.25 | ceteareth-15 |
| 37-14 | 360 | 1.0 | 10.0 | 1.25 | steareth-30 |
| 37-15 | 360 | 1.0 | 10.0 | 1.25 | steareth-20 |
| 37-16 | 360 | 1.0 | 10.0 | 1.25 | oleth-20 |
| 37-17 | 360 | 1.0 | 10.0 | 1.25 | ceteareth-27 |
| 37-18 | 163 | 0.5 | 5.0 | | laureth-23 |

Velvetleaf (*Abutilon theophrasti*, ABUTH) and Japanese millet (*Echinochloa crus-galli*, ECHCF) plants were grown and treated by the standard procedures given above. Applications of spray compositions were made 22 days after planting *ABUTH* and *ECHCF*, and evaluation of herbicidal inhibition was done 18 days after application.

Formulations B and J were applied as comparative treatments. Results, averaged for all replicates of each treatment, are shown in Table 37b.

TABLE 37b

| Concentrate composition | Glyphosate rate g a.e./ha | % Inhibition ABUTH | % Inhibition ECHCF |
|---|---|---|---|
| Formulation B | 100 | 0 | 30 |
| | 200 | 2 | 60 |
| | 300 | 17 | 75 |
| | 400 | 50 | 73 |
| Formulation J | 100 | 20 | 63 |
| | 200 | 42 | 98 |
| | 300 | 75 | 100 |
| | 400 | 83 | 98 |
| 37-01 | 100 | 27 | 57 |
| | 200 | 67 | 98 |
| | 300 | 80 | 99 |
| | 400 | 87 | 98 |
| 37-02 | 100 | 27 | 63 |
| | 200 | 53 | 87 |
| | 300 | 77 | 99 |
| | 400 | 87 | 99 |
| 37-03 | 100 | 12 | 50 |
| | 200 | 53 | 99 |
| | 300 | 65 | 100 |
| | 400 | 83 | 99 |
| 37-04 | 100 | 20 | 63 |
| | 200 | 50 | 98 |
| | 300 | 73 | 98 |
| | 400 | 87 | 98 |
| 37-05 | 100 | 18 | 70 |
| | 200 | 57 | 93 |
| | 300 | 80 | 99 |
| | 400 | 83 | 99 |

TABLE 37b-continued

| Concentrate composition | Glyphosate rate g a.e./ha | % Inhibition ABUTH | ECHCF |
|---|---|---|---|
| 37-06 | 100 | 17 | 63 |
|  | 200 | 35 | 95 |
|  | 300 | 60 | 100 |
|  | 400 | 75 | 100 |
| 37-07 | 100 | 3 | 43 |
|  | 200 | 43 | 95 |
|  | 300 | 62 | 100 |
|  | 400 | 68 | 96 |
| 37-08 | 100 | 20 | 43 |
|  | 200 | 43 | 88 |
|  | 300 | 75 | 99 |
|  | 400 | 80 | 97 |
| 37-09 | 100 | 37 | 57 |
|  | 200 | 55 | 93 |
|  | 300 | 83 | 100 |
|  | 400 | 83 | 99 |
| 37-10 | 100 | 37 | 50 |
|  | 200 | 60 | 96 |
|  | 300 | 83 | 99 |
|  | 400 | 88 | 99 |
| 37-11 | 100 | 8 | 37 |
|  | 200 | 37 | 93 |
|  | 300 | 68 | 99 |
|  | 400 | 70 | 97 |
| 37-12 | 100 | 13 | 43 |
|  | 200 | 40 | 91 |
|  | 300 | 67 | 100 |
|  | 400 | 77 | 96 |
| 37-13 | 100 | 25 | 40 |
|  | 200 | 40 | 80 |
|  | 300 | 62 | 97 |
|  | 400 | 78 | 98 |
| 37-14 | 100 | 23 | 33 |
|  | 200 | 37 | 86 |
|  | 300 | 75 | 99 |
|  | 400 | 78 | 94 |
| 37-15 | 100 | 23 | 30 |
|  | 200 | 43 | 78 |
|  | 300 | 53 | 93 |
|  | 400 | 78 | 98 |
| 37-16 | 100 | 23 | 37 |
|  | 200 | 37 | 95 |
|  | 300 | 63 | 97 |
|  | 400 | 78 | 95 |
| 37-17 | 100 | 18 | 50 |
|  | 200 | 45 | 88 |
|  | 300 | 75 | 69 |
|  | 400 | 73 | 93 |
| 37-18 | 100 | missing | missing |
|  | 200 | missing | missing |
|  | 300 | missing | missing |
|  | 400 | missing | missing |

Compositions exhibiting herbicidal effectiveness greater than that provided by commercial standard Formulation J included 37-01 (steareth-20 plus butyl stearate), 37-09 (ceteareth-15) and 37-10 (steareth-20 plus butyl stearate).

Example 38

Aqueous concentrate compositions were prepared containing glyphosate IPA salt and excipient ingredients as shown in Table 38a. All are oil-in-water emulsions and were prepared by process (vii).

TABLE 38a

| Concentrate composition | Glyphosate g a.e./l | % w/w Butyl stearate | Surfactant | Type of surfactant |
|---|---|---|---|---|
| 38-01 | 163 | 1.00 | 10.0 | laureth-23 |
| 38-02 | 163 | 0.50 | 5.0 | laureth-23 |
| 38-03 | 163 | 0.25 | 2.5 | laureth-23 |
| 38-04 | 163 | 1.00 | 10.0 | Neodol 1-9 |
| 38-05 | 163 | 0.50 | 5.0 | Neodol 1-9 |
| 38-06 | 163 | 0.25 | 2.5 | Neodol 1-9 |
| 38-07 | 163 | 1.00 | 10.0 | steareth-10 |
| 38-08 | 163 | 0.50 | 5.0 | steareth-10 |
| 38-09 | 163 | 0.25 | 2.5 | steareth-10 |
| 38-10 | 163 | 0.50 | 5.0 | steareth-20 |
| 38-11 | 163 | 0.25 | 2.5 | steareth-20 |
| 38-12 | 163 | 0.25 | 1.0 | steareth-20 |
| 38-13 | 163 | 0.50 | 5.0 | oleth-20 |
| 38-14 | 163 | 0.25 | 2.5 | oleth-20 |
| 38-15 | 163 | 0.25 | 1.0 | oleth-20 |
| 38-16 | 163 | 0.50 | 5.0 | ceteareth-27 |
| 38-17 | 163 | 0.25 | 2.5 | ceteareth-27 |
| 38-18 | 163 | 0.25 | 1.0 | ceteareth-27 |

Velvetleaf (*Abutilon theophrasti*, ABUTH) and Japanese millet (*Echinochloa crus-galli*, ECHCF) plants were grown and treated by the standard procedures given above. Applications of spray compositions were made 21 days after planting ABUTH and ECHCF, and evaluation of herbicidal inhibition was done 20 days after application.

Formulations B and J were applied as comparative treatments. Results, averaged for all replicates of each treatment, are shown in Table 38b.

TABLE 38b

| Concentrate composition | Glyphosate rate g a.e./ha | % Inhibition ABUTH | ECHCF |
|---|---|---|---|
| Formulation B | 100 | 0 | 42 |
|  | 200 | 0 | 43 |
|  | 300 | 23 | 50 |
|  | 400 | 0 | 28 |
| Formulation J | 100 | 0 | 73 |
|  | 200 | 57 | 85 |
|  | 300 | 68 | 93 |
|  | 400 | 87 | 94 |
| 38-01 | 100 | 18 | 75 |
|  | 200 | 58 | 92 |
|  | 300 | 85 | 90 |
|  | 400 | 94 | 95 |
| 38-02 | 100 | 3 | 77 |
|  | 200 | 47 | 90 |
|  | 300 | 65 | 89 |
|  | 400 | 87 | 95 |
| 38-03 | 100 | 13 | 80 |
|  | 200 | 53 | 88 |
|  | 300 | 72 | 98 |
|  | 400 | 82 | 99 |
| 38-04 | 100 | 0 | 0 |
|  | 200 | 53 | 88 |
|  | 300 | 67 | 95 |
|  | 400 | 83 | 95 |
| 38-05 | 100 | 2 | 60 |
|  | 200 | 50 | 83 |
|  | 300 | 70 | 93 |
|  | 400 | 85 | 92 |
| 38-06 | 100 | 0 | 52 |
|  | 200 | 55 | 83 |
|  | 300 | 62 | 96 |
|  | 400 | 77 | 98 |

TABLE 38b-continued

| Concentrate composition | Glyphosate rate g a.e./ha | % Inhibition ABUTH | ECHCF |
|---|---|---|---|
| 38-07 | 100 | 8 | 70 |
|  | 200 | 68 | 95 |
|  | 300 | 91 | 99 |
|  | 400 | 95 | 100 |
| 38-08 | 100 | 10 | 65 |
|  | 200 | 67 | 99 |
|  | 300 | 78 | 99 |
|  | 400 | 93 | 100 |
| 38-09 | 100 | 5 | 80 |
|  | 200 | 52 | 98 |
|  | 300 | 75 | 100 |
|  | 400 | 86 | 98 |
| 38-10 | 100 | 0 | 65 |
|  | 200 | 62 | 84 |
|  | 300 | 58 | 94 |
|  | 400 | 75 | 100 |
| 38-11 | 100 | 5 | 83 |
|  | 200 | 50 | 99 |
|  | 300 | 63 | 97 |
|  | 400 | 87 | 99 |
| 38-12 | 100 | 10 | 76 |
|  | 200 | 60 | 96 |
|  | 300 | 72 | 100 |
|  | 400 | 100 | 100 |
| 38-13 | 100 | 20 | 85 |
|  | 200 | 67 | 100 |
|  | 300 | 91 | 100 |
|  | 400 | 96 | 98 |
| 38-14 | 100 | 23 | 68 |
|  | 200 | 62 | 89 |
|  | 300 | 80 | 100 |
|  | 400 | 99 | 99 |
| 38-15 | 100 | 5 | 57 |
|  | 200 | 55 | 93 |
|  | 300 | 89 | 95 |
|  | 400 | 90 | 98 |
| 38-16 | 100 | 30 | 68 |
|  | 200 | 68 | 94 |
|  | 300 | 83 | 98 |
|  | 400 | 100 | 100 |
| 38-17 | 100 | 43 | 68 |
|  | 200 | 62 | 99 |
|  | 300 | 78 | 100 |
|  | 400 | 100 | 99 |
| 38-18 | 100 | 25 | 52 |
|  | 200 | 53 | 84 |
|  | 300 | 85 | 94 |
|  | 400 | 98 | 95 |

Compositions having a 1:3 or lower weight/weight ratio of surfactant to glyphosate a.e., yet outperforming commercial standard Formulation J at least on *ABUTH* in this test, included those containing just 1% alkylether surfactant (ratio about 1:15) together with 0.25% butyl stearate, where the alkylether surfactant was steareth-20 (38-12), oleth-20 (38-15) or ceteareth-27 (38-18).

Example 39

Aqueous concentrate compositions were prepared containing glyphosate IPA salt and excipient ingredients as shown in Table 39a. All are aqueous solution concentrates containing colloidal particulates and were prepared by process (ix).

The compositions of this example all showed acceptable storage stability. The compositions shown as containing colloidal particulate were not storage-stable unless the colloidal particulate was included as shown.

TABLE 39a

| Conc. comp. | Glyphosate g a.e./l | % w/w Surfactant | Aerosil | Other | Type of surfactant | Type of Aerosil | Other component |
|---|---|---|---|---|---|---|---|
| 39-01 | 488 | 3.0 | 1.5 |  | steareth-20 | MOX-80/380 (1:2) |  |
| 39-02 | 488 | 4.5 | 1.5 |  | steareth-20 | 380 |  |
| 39-03 | 488 | 4.5 | 1.5 |  | steareth-20 | MOX-80/380 (1:2) |  |
| 39-04 | 488 | 4.5 | 1.5 |  | steareth-20 | MOX-80/MOX-170 (1:2) |  |
| 39-05 | 488 | 6.0 | 1.5 | 4.12 | steareth-20 | 380 | glycerin |
| 39-06 | 488 | 3.0 | 1.5 |  | steareth-20 | 380 |  |
| 39-07 | 488 | 3.0 | 1.5 | 7.12 | oleth-20 | 380 | propylene glycol |
| 39-08 | 488 | 3.0 | 1.5 |  | oleth-20 | MOX-80/380 (1:2) |  |
| 39-09 | 488 | 4.5 | 1.5 |  | oleth-20 | 380 |  |
| 39-10 | 488 | 4.5 | 1.5 |  | oleth-20 | MOX-80/380 (1:2) |  |

Velvetleaf (*Abutilon theophrasti*, ABUTH) and Japanese millet (*Echinochloa crus-galli*, ECHCF) plants were grown and treated by the standard procedures given above. Applications of spray compositions were made 21 days after planting *ABUTH* and *ECHCF*, and evaluation of herbicidal inhibition was done 20 days after application.

Formulations B and J were applied as comparative treatments. Results, averaged for all replicates of each treatment, are shown in Table 39b.

TABLE 39b

| Concentrate composition | Glyphosate rate g a.e./ha | % Inhibition ABUTH | ECHCF |
|---|---|---|---|
| Formulation B | 100 | 0 | 25 |
|  | 200 | 35 | 27 |
|  | 300 | 48 | 28 |
|  | 400 | 47 | 48 |
| Formulation J | 100 | 50 | 75 |
|  | 200 | 80 | 90 |
|  | 300 | 97 | 96 |
|  | 400 | 99 | 98 |
| 39-01 | 100 | 53 | 33 |
|  | 200 | 83 | 52 |
|  | 300 | 98 | 72 |
|  | 400 | 98 | 79 |
| 39-02 | 100 | 43 | 27 |
|  | 200 | 80 | 57 |
|  | 300 | 87 | 73 |
|  | 400 | 96 | 78 |
| 39-03 | 100 | 48 | 30 |
|  | 200 | 81 | 70 |
|  | 300 | 98 | 78 |
|  | 400 | 63 | 57 |

TABLE 39b-continued

| Concentrate composition | Glyphosate rate g a.e./ha | % Inhibition ABUTH | ECHCF |
|---|---|---|---|
| 39-04 | 100 | 45 | 32 |
|  | 200 | 87 | 75 |
|  | 300 | 97 | 73 |
|  | 400 | 98 | 83 |
| 39-05 | 100 | 38 | 27 |
|  | 200 | 37 | 23 |
|  | 300 | 45 | 32 |

Example 40

Dry granular concentrate compositions were prepared containing glyphosate ammonium salt and excipient ingredients as shown in Table 40a. The preparation procedure was as follows. Ammonium glyphosate powder was added to a blender. Excipient ingredients were slowly added, together with sufficient water to wet the powder and form a stiff dough. The blender was operated for sufficient time to thoroughly mix all ingredients. The dough was then transferred to extrusion apparatus and was extruded to form granules, which were finally dried in a fluid bed dryer.

TABLE 40a

| Conc. comp. | % w/w Glyphosate a.e. | Lecithin | Butyl stearate | Surfactant | Colloidal particulate | Type of surfactant | Type of colloidal particulate |
|---|---|---|---|---|---|---|---|
| 40-01 | 68.7 |  |  | 21.0 |  | steareth-20 |  |
| 40-02 | 66.0 |  | 2.2 | 22.0 |  | steareth-20 |  |
| 40-03 | 66.1 |  |  | 24.0 |  | oleth-20 |  |
| 40-04 | 66.0 |  | 2.2 | 22.0 |  | oleth-20 |  |
| 40-05 | 67.9 | 10.0 | 2.0 | 10.0 |  | MON 0818 |  |
| 40-06 | 59.2 | 10.0 |  | 20.0 + 2.0 |  | FC-754 + MON 0818 |  |
| 40-07 | 68.0 |  |  | 21.0 | 0.8 | Flomo 1407 | Aerosil 90 |
| 40-08 | 68.0 |  |  | 21.0 | 0.8 | Flomo 1407 | Aluminum oxide C |
| 40-09 | 66.1 |  |  | 24.0 |  | ceteth-20 |  |
| 40-10 | 66.0 |  | 2.2 | 22.0 |  | ceteth-20 |  |
| 40-11 | 71.2 |  |  | 16.1 | 2.0 | ceteth-20 | Aerosil 380 |
| 40-12 | 71.1 |  |  | 16.3 | 1.0 | ceteth-20 | Aerosil blend(*) |
| 40-13 | 71.2 |  |  | 16.1 | 2.0 | steareth-20 | Aerosil 380 |
| 40-14 | 71.2 |  |  | 16.1 | 1.0 | steareth-20 | Aerosil blend(*) |
| 40-15 | 68.0 |  |  | 20.0 | 1.9 | oleth-20 | Aerosil-380 |
| 40-16 | 70.8 |  |  | 16.6 | 1.0 | oleth-20 | Aerosil blend(*) |

(*)Aerosil MOX-80 + Aerosil MOX-170 (1:1)

TABLE 39b-continued

| Concentrate composition | Glyphosate rate g a.e./ha | % Inhibition ABUTH | ECHCF |
|---|---|---|---|
|  | 400 | 35 | 18 |
| 39-06 | 100 | 42 | 40 |
|  | 200 | 78 | 52 |
|  | 300 | 91 | 72 |
|  | 400 | 96 | 80 |
| 39-07 | 100 | 37 | 43 |
|  | 200 | 48 | 32 |
|  | 300 | 73 | 58 |
|  | 400 | 55 | 28 |
| 39-08 | 100 | 43 | 37 |
|  | 200 | 68 | 57 |
|  | 300 | 84 | 62 |
|  | 400 | 89 | 82 |
| 39-09 | 100 | 37 | 32 |
|  | 200 | 83 | 67 |
|  | 300 | 94 | 82 |
|  | 400 | 63 | 48 |
| 39-10 | 100 | 32 | 40 |
|  | 200 | 75 | 68 |
|  | 300 | 90 | 88 |
|  | 400 | 65 | 63 |

Several high-load (488 g a.e./l) glyphosate compositions exhibited herbicidal effectiveness on *ABUTH* equal to commercial standard Formulation J, but none was equal to Formulation J on *ECHCF* in this test.

Velvetleaf (*Abutilon theophrasti*, ABUTH) and Japanese millet (*Echinochloa crus-galli*, ECHCF) plants were grown and treated by the standard procedures given above. Applications of spray compositions were made 21 days after planting *ABUTH* and *ECHCF*, and evaluation of herbicidal inhibition was done 20 days after application.

Formulations J and K were applied as comparative treatments. Results, averaged for all replicates of each treatment, are shown in Table 40b.

TABLE 40b

| Concentrate composition | Glyphosate rate g a.e./ha | % Inhibition ABUTH | ECHCF |
|---|---|---|---|
| Formulation J | 100 | 52 | 80 |
|  | 200 | 90 | 96 |
|  | 300 | 96 | 100 |
|  | 400 | 97 | 99 |
| Formulation K | 100 | 33 | 70 |
|  | 200 | 67 | 93 |
|  | 300 | 83 | 99 |
|  | 400 | 93 | 100 |
| 40-01 | 100 | 47 | 60 |
|  | 200 | 87 | 98 |
|  | 300 | 97 | 98 |
|  | 400 | 100 | 98 |
| 40-02 | 100 | 47 | 63 |
|  | 200 | 80 | 94 |
|  | 300 | 90 | 99 |
|  | 400 | 98 | 100 |

TABLE 40b-continued

| Concentrate composition | Glyphosate rate g a.e./ha | % Inhibition ABUTH | % Inhibition ECHCF |
|---|---|---|---|
| 40-03 | 100 | 62 | 62 |
|  | 200 | 83 | 93 |
|  | 300 | 97 | 96 |
|  | 400 | 97 | 100 |
| 40-04 | 100 | 47 | 57 |
|  | 200 | 78 | 94 |
|  | 300 | 87 | 100 |
|  | 400 | 98 | 100 |
| 40-05 | 100 | 25 | 53 |
|  | 200 | 60 | 88 |
|  | 300 | 80 | 97 |
|  | 400 | 83 | 98 |
| 40-06 | 100 | 35 | 37 |
|  | 200 | 65 | 62 |
|  | 300 | 83 | 83 |
|  | 400 | 90 | 95 |
| 40-07 | 100 | 63 | 55 |
|  | 200 | 72 | 97 |
|  | 300 | 83 | 100 |
|  | 400 | 94 | 100 |
| 40-08 | 100 | 30 | 65 |
|  | 200 | 72 | 94 |
|  | 300 | 87 | 100 |
|  | 400 | 92 | 99 |
| 40-09 | 100 | 37 | 63 |
|  | 200 | 77 | 83 |
|  | 300 | 88 | 99 |
|  | 400 | 97 | 99 |
| 40-10 | 100 | 40 | 55 |
|  | 200 | 83 | 93 |
|  | 300 | 94 | 96 |
|  | 400 | 98 | 99 |
| 40-11 | 100 | 42 | 55 |
|  | 200 | 78 | 94 |
|  | 300 | 88 | 92 |
|  | 400 | 94 | 99 |
| 40-12 | 100 | 38 | 58 |
|  | 200 | 78 | 97 |
|  | 300 | 92 | 97 |
|  | 400 | 95 | 100 |
| 40-13 | 100 | 25 | 50 |
|  | 200 | 80 | 88 |
|  | 300 | 96 | 95 |
|  | 400 | 98 | 98 |
| 40-14 | 100 | 50 | 53 |
|  | 200 | 88 | 92 |
|  | 300 | 98 | 99 |
|  | 400 | 99 | 99 |
| 40-15 | 100 | 33 | 57 |
|  | 200 | 75 | 91 |
|  | 300 | 94 | 97 |
|  | 400 | 98 | 99 |
| 40-16 | 100 | 33 | 55 |
|  | 200 | 77 | 90 |
|  | 300 | 88 | 99 |
|  | 400 | 96 | 100 |

Several dry granular compositions of this Example outperformed commercial standard composition K, at least on *ABUTH*. They included 40-01 to 40-04 and 40-10 to 40-16, all containing an alkylether surfactant (steareth-20, oleth-20 or ceteth-20).

Example 41

Aqueous concentrate compositions were prepared containing glyphosate IPA salt and excipient ingredients as shown in Table 41a. All are oil-in-water emulsions and were prepared by process (vii). Soybean lecithin (45% phospholipid, Avanti) was first dispersed in water either by ultrasonication or by use of a microfluidizer as indicated in the column of Table 41a headed "Process".

TABLE 41a

| Conc. comp. | Glyphosate g a.e./l | % w/w | | | | | | |
|---|---|---|---|---|---|---|---|---|
| | | Lecithin | Butyl stearate | Ethomeen T/25 | MON 0818 | Ceteareth-20 | Ceteareth-27 | Process(*) |
| 41-01 | 220 | 0.75 | 3.75 | 3.0 | | | 3.0 | B |
| 41-02 | 220 | 0.75 | 0.75 | 3.0 | | | 3.0 | B |
| 41-03 | 220 | 0.75 | 3.75 | 3.0 | | 3.0 | | B |
| 41-04 | 220 | 0.75 | 0.75 | 3.0 | | 3.0 | | B |
| 41-05 | 220 | 6.00 | 1.50 | 3.0 | | 3.0 | | B |
| 41-06 | 220 | 6.00 | 1.50 | 3.0 | | | 3.0 | B |
| 41-07 | 220 | 4.00 | 1.00 | 3.0 | | 3.0 | | B |
| 41-08 | 220 | 4.00 | 1.00 | 3.0 | | | 3.0 | B |
| 41-09 | 220 | 0.75 | 3.75 | 3.0 | | | 3.0 | A |
| 41-10 | 220 | 0.75 | 0.75 | 3.0 | | | 3.0 | A |
| 41-11 | 220 | 0.75 | 3.75 | 6.0 | | | | B |
| 41-12 | 220 | 0.75 | 3.75 | | | 6.0 | | B |
| 41-13 | 345 | 6.00 | 1.50 | 4.5 | 4.5 | | | B |
| 41-14 | 345 | 6.00 | 1.50 | 6.0 | | | 3.0 | B |
| 41-15 | 345 | 6.00 | 1.50 | 6.0 | 6.0 | | | B |
| 41-16 | 345 | 0.50 | 7.50 | 12.0 | | | | B |
| 41-17 | 345 | 6.00 | 1.50 | 4.5 | 4.5 | | 3.0 | B |

(*)Process:
A Ultrasonicated
B Microfluidized, 3 cycles

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and ECHCF, and evaluation of herbicidal inhibition was done 15 days after application.

Formulations B and J were applied as comparative treatments. Results, averaged for all replicates of each treatment, are shown in Table 41b.

TABLE 41b

| Concentrate composition | Glyphosate rate g a.e./ha | % Inhibition ABUTH | ECHCF |
|---|---|---|---|
| Formulation B | 150 | 45 | 82 |
|  | 250 | 55 | 71 |
|  | 350 | 80 | 72 |
|  | 450 | 88 | 77 |
| Formulation J | 150 | 55 | 83 |
|  | 250 | 89 | 88 |
|  | 350 | 97 | 93 |
|  | 450 | 99 | 93 |
|  | 550 | 99 | 87 |
| 41-01 | 150 | 92 | 83 |
|  | 250 | 96 | 96 |
|  | 350 | 99 | 96 |
|  | 450 | 100 | 86 |
| 41-02 | 150 | 85 | 93 |
|  | 250 | 97 | 78 |
|  | 350 | 97 | 90 |
|  | 450 | 99 | 90 |
| 41-03 | 150 | 87 | 85 |
|  | 250 | 98 | 92 |
|  | 350 | 99 | 95 |
|  | 450 | 100 | 95 |
| 41-04 | 150 | 87 | 89 |
|  | 250 | 97 | 92 |
|  | 350 | 99 | 94 |
|  | 450 | 99 | 91 |
| 41-05 | 150 | 87 | 77 |
|  | 250 | 98 | 89 |
|  | 350 | 99 | 93 |
|  | 450 | 99 | 84 |
| 41-06 | 150 | 12 | 18 |
|  | 250 | 96 | 73 |
|  | 350 | 99 | 85 |
|  | 450 | 99 | 84 |
| 41-07 | 150 | 82 | 89 |
|  | 250 | 88 | 96 |
|  | 350 | 96 | 98 |
|  | 450 | 97 | 97 |
| 41-08 | 150 | 88 | 94 |
|  | 250 | 95 | 90 |
|  | 350 | 99 | 98 |
|  | 450 | 99 | 98 |
| 41-09 | 150 | 94 | 94 |
|  | 250 | 95 | 100 |
|  | 350 | 97 | 99 |
|  | 450 | 99 | 98 |
| 41-10 | 150 | 94 | 94 |
|  | 250 | 98 | 99 |
|  | 350 | 99 | 97 |
|  | 450 | 99 | 96 |
| 41-11 | 150 | 83 | 81 |
|  | 250 | 94 | 88 |
|  | 350 | 98 | 93 |
|  | 450 | 99 | 99 |
| 41-12 | 150 | 68 | 79 |
|  | 250 | 95 | 96 |
|  | 350 | 98 | 100 |
|  | 450 | 99 | 98 |
| 41-13 | 150 | 86 | 98 |
|  | 250 | 95 | 98 |
|  | 350 | 99 | 100 |
|  | 450 | 100 | 98 |
| 41-14 | 150 | 85 | 98 |
|  | 250 | 98 | 98 |
|  | 350 | 99 | 98 |
|  | 450 | 100 | 98 |
| 41-15 | 150 | 86 | 95 |
|  | 250 | 97 | 97 |
|  | 350 | 99 | 95 |
|  | 450 | 100 | 96 |
| 41-16 | 150 | 93 | 94 |
|  | 250 | 98 | 98 |
|  | 350 | 99 | 98 |
|  | 450 | 100 | 97 |
| 41-17 | 150 | 95 | 96 |
|  | 250 | 98 | 100 |
|  | 350 | 100 | 100 |
|  | 450 | 100 | 98 |

Many compositions containing lecithin and butyl stearate, together with ceteareth-20 or ceteareth-27, outperformed commercial standard Formulation J in this test.

Example 42

Aqueous concentrate compositions were prepared containing glyphosate IPA salt and excipient ingredients as shown in Table 42a. Concentrate compositions 42-04 and 42-05 are aqueous solution concentrates and were prepared by process (viii). Concentrate compositions 42-06 to 42-13 are aqueous solution concentrates containing colloidal particulates and were prepared by process (ix). Concentrate compositions 42-01 to 42-03 contain colloidal particulate but no surfactant.

The compositions of this example containing colloidal particulate all showed acceptable storage stability. Of those containing steareth-20 but no colloidal particulate, composition 42-04 was acceptable storage-stable but composition 42-05 was not.

TABLE 42a

| Concentrate composition | Glyphosate g a.e./l | % w/w Steareth-20 | Oleth-20 | Aerosil | Type of Aerosil |
|---|---|---|---|---|---|
| 42-01 | 484 |  |  | 1.5 | MOX-80 |
| 42-02 | 484 |  |  | 1.5 | 380 |
| 42-03 | 484 |  |  | 1.5 | MOX-80/MOX-170 (1:1) |
| 42-04 | 484 | 1.5 |  |  | none |
| 42-05 | 484 | 3.0 |  |  | none |
| 42-06 | 484 | 3.0 |  | 1.5 | MOX-170 |
| 42-07 | 484 | 3.0 |  | 1.5 | 380 |
| 42-08 | 484 | 3.0 |  | 1.5 | MOX-80/380 (1:1) |
| 42-09 | 484 | 3.0 |  | 1.5 | MOX-80/MOX-170 (1:1) |
| 42-10 | 484 |  | 3.0 | 1.5 | MOX-80 |
| 42-11 | 484 |  | 3.0 | 1.5 | MOX-170 |
| 42-12 | 484 |  | 3.0 | 1.5 | 380 |
| 42-13 | 484 |  | 3.0 | 1.5 | MOX-80/380(1:1) |

Velvetleaf (*Abutilon theophrasti*, ABUTH) and Japanese millet (*Echinochloa crus-galli*, ECHCF) plants were grown and treated by the standard procedures given above. Applications of spray compositions were made 20 days after planting ABUTH and ECHCF, and evaluation of herbicidal inhibition was done 19 days after application.

Formulations B and J were applied as comparative treatments. Results, averaged for all replicates of each treatment, are shown in Table 42b.

TABLE 42b

| Concentrate composition | Glyphosate rate g a.e./ha | % Inhibition ABUTH | % Inhibition ECHCF |
|---|---|---|---|
| Formulation B | 100 | 3 | 38 |
|  | 200 | 28 | 63 |
|  | 300 | 37 | 75 |
|  | 400 | 55 | 78 |
| Formulation J | 100 | 23 | 73 |
|  | 200 | 43 | 92 |
|  | 300 | 67 | 96 |
|  | 400 | 92 | 97 |
| 42-01 | 100 | 23 | 60 |
|  | 200 | 40 | 77 |
|  | 300 | 65 | 91 |
|  | 400 | 75 | 92 |
| 42-02 | 100 | 18 | 50 |
|  | 200 | 25 | 53 |
|  | 300 | 33 | 75 |
|  | 400 | 67 | 82 |
| 42-03 | 100 | 27 | 57 |
|  | 200 | 35 | 72 |
|  | 300 | 50 | 86 |
|  | 400 | 70 | 93 |
| 42-04 | 100 | 42 | 67 |
|  | 200 | 48 | 78 |
|  | 300 | 78 | 82 |
|  | 400 | 80 | 85 |
| 42-05 | 100 | 28 | 43 |
|  | 200 | 45 | 77 |
|  | 300 | 70 | 92 |
|  | 400 | 80 | 95 |
| 42-06 | 100 | 42 | 57 |
|  | 200 | 70 | 75 |
|  | 300 | 89 | 87 |
|  | 400 | 94 | 94 |
| 42-07 | 100 | 43 | 68 |
|  | 200 | 62 | 90 |
|  | 300 | 88 | 92 |
|  | 400 | 97 | 92 |
| 42-08 | 100 | 53 | 57 |
|  | 200 | 72 | 87 |
|  | 300 | 88 | 94 |
|  | 400 | 92 | 97 |
| 42-09 | 100 | 27 | 60 |
|  | 200 | 62 | 75 |

TABLE 42b-continued

| Concentrate composition | Glyphosate rate g a.e./ha | % Inhibition ABUTH | % Inhibition ECHCF |
|---|---|---|---|
|  | 300 | 75 | 92 |
|  | 400 | 83 | 90 |
| 42-10 | 100 | 47 | 43 |
|  | 200 | 73 | 73 |
|  | 300 | 82 | 88 |
|  | 400 | 97 | 93 |
| 42-11 | 100 | 48 | 57 |
|  | 200 | 63 | 75 |
|  | 300 | 80 | 91 |
|  | 400 | 89 | 98 |
| 42-12 | 100 | 30 | 40 |
|  | 200 | 42 | 63 |
|  | 300 | 68 | 75 |
|  | 400 | 73 | 83 |
| 42-13 | 100 | 37 | 40 |
|  | 200 | 57 | 75 |
|  | 300 | 73 | 80 |
|  | 400 | 78 | 94 |

Remarkably strong herbicidal effectiveness was provided by composition 42-05, in spite of its very low surfactant (steareth-20) to glyphosate a.e. ratio of about 1:13. Activity, at least on *ABUTH*, was further improved to a significant degree by inclusion in the composition of colloidal particulates such as Aerosil MOX-170 (42-06), Aerosil 380 (42-07), a blend of Aerosil MOX-80 and Aerosil 380 (42-08), and a blend of Aerosil MOX-80 and Aerosil MOX-170 (42-09).

Example 43

Aqueous and dry granular concentrate compositions were prepared as shown in Table 43a. Dry granular concentrate compositions 43-01 to 43-11 contain glyphosate ammonium salt, and were prepared by the procedure described in Example 40.

Aqueous concentrate compositions 43-12 to 43-16 contain glyphosate IPA salt and soybean lecithin (45% phospholipid, Avanti) and were prepared by process (v).

TABLE 43a

| Conc. comp. | Glyphosate g a.e./l | % w/w Glyphosate a.e. | Lecithin | Butyl stearate | Surfactant | Colloidal particulate | Type of surfactant | Type of colloidal particulate |
|---|---|---|---|---|---|---|---|---|
| 43-01 |  | 68.7 |  |  | 21.0 |  | steareth-20 |  |
| 43-02 |  | 66.1 |  |  | 24.0 |  | oleth-20 |  |
| 43-03 |  | 67.9 | 10.0 | 2.0 | 10.0 |  | MON 0818 |  |
| 43-04 |  | 59.2 | 10.0 |  | 20.0 + 2.0 |  | FC-754 + MON 0818 |  |
| 43-05 |  | 66.1 |  |  | 24.0 |  | ceteth-20 |  |
| 43-06 |  | 71.2 |  |  | 16.1 | 2.0 | steareth-20 | Aerosil 380 |
| 43-07 |  | 71.2 |  |  | 16.1 | 2.0 | steareth-20 | Aerosil blend |
| 43-08 |  | 68.0 |  |  | 20.0 | 1.9 | oleth-20 | Aerosil 380 |
| 43-09 |  | 63.5 |  |  | 25.0 | 2.0 | steareth-20 | Aerosil blend |
| 43-10 |  | 67.9 |  |  | 20.0 | 2.0 | steareth-20 | Aerosil blend |
| 43-11 |  | 72.2 |  |  | 15.0 | 2.0 | steareth-20 | Aerosil blend |
| 43-12 | 370 |  | 4.7 |  | 4.7 |  | steareth-20 |  |
| 43-13 | 350 |  | 4.9 |  | 4.9 |  | ceteareth-27 |  |
| 43-14 | 348 |  | 5.0 |  | 5.0 |  | ceteareth-15 |  |
| 43-15 | 348 |  | 5.0 |  | 5.0 |  | oleth-20 |  |
| 43-16 | 351 |  | 4.4 |  | 5.0 |  | steareth-30 |  |

Aerosil blend: Aerosil MOX-80 + Aerosil MOX-170 (1:1)

Velvetleaf (*Abutilon theophrasti*, ABUTH) and Japanese millet (*Echinochloa crus-galli*, ECHCF) plants were grown and treated by the standard procedures given above. Applications of spray compositions were made 20 days after planting ABUTH and ECHCF, and evaluation of herbicidal inhibition was done 16 days after application.

Formulations J and K were applied as comparative treatments. Results, averaged for all replicates of each treatment, are shown in Table 43b.

TABLE 43b

| Concentrate composition | Glyphosate rate g a.e./ha | % Inhibition ABUTH | % Inhibition ECHCF |
|---|---|---|---|
| Formulation J | 100 | 0 | 20 |
| | 200 | 28 | 57 |
| | 300 | 58 | 96 |
| | 400 | 73 | 99 |
| Formulation K | 100 | 22 | 13 |
| | 200 | 42 | 83 |
| | 300 | 48 | 91 |
| | 400 | 58 | 95 |
| 43-01 | 100 | 28 | 30 |
| | 200 | 48 | 80 |
| | 300 | 80 | 97 |
| | 400 | 85 | 99 |
| 43-02 | 100 | 43 | 52 |
| | 200 | 68 | 80 |
| | 300 | 72 | 88 |
| | 400 | 86 | 94 |
| 43-03 | 100 | 23 | 37 |
| | 200 | 50 | 83 |
| | 300 | 75 | 88 |
| | 400 | 85 | 96 |
| 43-04 | 100 | 50 | 45 |
| | 200 | 73 | 80 |
| | 300 | 85 | 92 |
| | 400 | 95 | 94 |
| 43-05 | 100 | 18 | 45 |
| | 200 | 65 | 83 |
| | 300 | 87 | 95 |
| | 400 | 94 | 86 |
| 43-06 | 100 | 47 | 50 |
| | 200 | 62 | 68 |
| | 300 | 82 | 94 |
| | 400 | 91 | 87 |
| 43-07 | 100 | 50 | 47 |
| | 200 | 60 | 78 |
| | 300 | 87 | 87 |
| | 400 | 93 | 93 |
| 43-08 | 100 | 30 | 55 |
| | 200 | 55 | 77 |
| | 300 | 82 | 85 |
| | 400 | 88 | 97 |
| 43-09 | 100 | 45 | 50 |
| | 200 | 57 | 78 |
| | 300 | 83 | 83 |
| | 400 | 84 | 89 |
| 43-10 | 100 | 42 | 50 |
| | 200 | 57 | 80 |
| | 300 | 73 | 91 |
| | 400 | 91 | 90 |
| 43-11 | 100 | 28 | 48 |
| | 200 | 50 | 75 |
| | 300 | 70 | 87 |
| | 400 | 82 | 89 |
| 43-12 | 100 | 20 | 40 |
| | 200 | 63 | 80 |
| | 300 | 67 | 96 |
| | 400 | 80 | 88 |
| 43-13 | 100 | 27 | 35 |
| | 200 | 50 | 85 |
| | 300 | 77 | 90 |
| | 400 | 84 | 86 |
| 43-14 | 100 | 27 | 25 |
| | 200 | 40 | 70 |
| | 300 | 68 | 94 |
| | 400 | 89 | 91 |
| 43-15 | 100 | 17 | 20 |
| | 200 | 47 | 82 |
| | 300 | 58 | 89 |
| | 400 | 91 | 95 |
| 43-16 | 100 | 22 | 20 |
| | 200 | 41 | 80 |
| | 300 | 84 | 89 |
| | 400 | 99 | 98 |

All compositions of the invention in this study exhibited greater herbicidal effectiveness on both ABUTH and ECHCF, in some cases by a very substantial margin, than commercial standard Formulation K.

Example 44

Aqueous concentrate compositions were prepared containing glyphosate IPA salt and excipient ingredients as shown in Table 44a. Concentrate compositions 44-01 to 44-07, 44-17 and 44-18 were prepared by process (v). Concentrate compositions 44-08 to 44-15 were prepared by process (x). Concentrate composition 44-16 was prepared by process (viii).

TABLE 44a

| Conc. comp. | Glyphosate g a.e./l | Lecithin | Fluorad FC-754 | Butyl stearate | Ethomeen T/25 | Ceteareth-20 | Arcosolve DPM | Ceteareth-27 |
|---|---|---|---|---|---|---|---|---|
| | | | | | % w/w | | | |
| 44-01 | 348 | 3.0 | 3.00 | | 0.75 | | | |
| 44-02 | 348 | 3.8 | 3.75 | | 5.00 | | | |
| 44-03 | 348 | 3.8 | 3.75 | | 7.50 | | | |
| 44-04 | 348 | 2.0 | 5.00 | | 0.75 | | | |
| 44-05 | 348 | 5.0 | 5.00 | | 0.75 | | | |
| 44-06 | 348 | 2.0 | 2.00 | | | | | |
| 44-07 | 348 | 1.0 | 1.00 | | | | | |
| 44-08 | 220 | 1.5 | | 1.5 | 3.00 | 3.0 | | |
| 44-09 | 220 | 1.5 | | 1.5 | 3.00 | | | 3.0 |
| 44-10 | 220 | 1.5 | | 1.5 | 6.00 | 3.0 | | |
| 44-11 | 220 | 1.5 | | 1.5 | 6.00 | | | 3.0 |
| 44-12 | 220 | 3.0 | | 1.5 | 3.00 | 3.0 | | |
| 44-13 | 220 | 3.0 | | 1.5 | 3.00 | | | 3.0 |
| 44-14 | 348 | 1.5 | | 1.5 | 6.00 | 3.0 | | |
| 44-15 | 348 | 3.0 | | 1.5 | 3.00 | 3.0 | | |
| 44-16 | 348 | | 3.00 | | | | | |
| 44-17 | 348 | 3.0 | | | | | 3.0 | |
| 44-18 | 348 | 5.0 | | | 13.00 | | 5.0 | |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 18 days after application.

Formulations B and J were applied as comparative treatments. Results, averaged for all replicates of each treatment, are shown in Table 44b.

TABLE 44b

| Concentrate composition | Glyphosate rate g a.e./ha | % Inhibition ABUTH | % Inhibition ECHCF |
|---|---|---|---|
| Formulation B | 100 | 28 | 32 |
| | 200 | 41 | 37 |
| | 300 | 73 | 64 |
| | 400 | 22 | 30 |
| Formulation J | 100 | 38 | 32 |
| | 200 | 82 | 73 |
| | 300 | 89 | 91 |
| | 400 | 97 | 89 |
| 44-01 | 100 | 73 | 28 |
| | 200 | 90 | 66 |
| | 300 | 97 | 92 |
| | 400 | 100 | 96 |
| 44-02 | 100 | 77 | 32 |
| | 200 | 87 | 67 |
| | 300 | 84 | 78 |
| | 400 | 98 | 84 |
| 44-03 | 100 | 79 | 33 |
| | 200 | 82 | 66 |
| | 300 | 99 | 81 |
| | 400 | 97 | 88 |
| 44-04 | 100 | 69 | 35 |
| | 200 | 95 | 59 |
| | 300 | 96 | 84 |
| | 400 | 92 | 91 |
| 44-05 | 100 | 82 | 32 |
| | 200 | 92 | 55 |
| | 300 | 96 | 71 |
| | 400 | 94 | 87 |
| 44-06 | 100 | 83 | 33 |
| | 200 | 100 | 52 |
| | 300 | 100 | 68 |
| | 400 | 99 | 75 |
| 44-07 | 100 | 77 | 35 |
| | 200 | 90 | 58 |
| | 300 | 95 | 71 |
| | 400 | 94 | 90 |
| 44-08 | 100 | 51 | 40 |
| | 200 | 89 | 75 |
| | 300 | 96 | 92 |
| | 400 | 95 | 98 |
| 44-09 | 100 | 76 | 57 |
| | 200 | 98 | 81 |
| | 300 | 97 | 86 |
| | 400 | 96 | 98 |
| 44-10 | 100 | 69 | 60 |
| | 200 | 98 | 63 |
| | 300 | 95 | 82 |
| | 400 | 99 | 90 |
| 44-11 | 100 | 61 | 60 |
| | 200 | 94 | 84 |
| | 300 | 97 | 89 |
| | 400 | 99 | 97 |
| 44-12 | 100 | 64 | 53 |
| | 200 | 95 | 82 |
| | 300 | 96 | 90 |
| | 400 | 95 | 98 |
| 44-13 | 100 | 61 | 58 |
| | 200 | 94 | 78 |
| | 300 | 88 | 87 |
| | 400 | 100 | 94 |
| 44-14 | 100 | 56 | 61 |
| | 200 | 88 | 77 |
| | 300 | 91 | 82 |
| | 400 | 97 | 89 |
| 44-15 | 100 | 42 | 52 |
| | 200 | 82 | 80 |
| | 300 | 86 | 90 |
| | 400 | 97 | 92 |
| 44-16 | 100 | 64 | 49 |
| | 200 | 86 | 75 |
| | 300 | 97 | 88 |
| | 400 | 100 | 82 |
| 44-17 | 100 | 57 | 32 |
| | 200 | 88 | 66 |
| | 300 | 95 | 73 |
| | 400 | 100 | 88 |
| 44-18 | 100 | 52 | 35 |

TABLE 44b-continued

| Concentrate composition | Glyphosate rate g a.e./ha | % Inhibition ABUTH | ECHCF |
|---|---|---|---|
| | 200 | 70 | 77 |
| | 300 | 82 | 79 |
| | 400 | 97 | 73 |

Compositions 44-08 to 44-15, containing lecithin, butyl stearate, Ethomeen T/25 and a $C_{16-18}$ alkylether surfactant (ceteareth-20 or ceteareth-27) exhibited a very high degree of herbicidal effectiveness. Not only was performance, at least of 44-08 to 44-13, on *ABUTH* substantially better than that of Formulation J, these compositions performed considerably better than Formulation J on *ECHCF* as well.

Example 45

Aqueous concentrate compositions were prepared containing glyphosate IPA salt and excipient ingredients as shown in Table 45a. All contain colloidal particulates and were prepared by process (ix).

The compositions of this example all showed acceptable storage stability. The compositions shown as containing colloidal particulate were not storage-stable unless the colloidal particulate was included as shown.

TABLE 45a

| Conc. comp. | Glyphosate g a.e./l | % w/w | | | | |
|---|---|---|---|---|---|---|
| | | Oil | Surfactant | Aerosil 380 | Type of oil | Type of surfactant |
| 45-01 | 360 | 1.0 | 10.0 | 1.25 | butyl stearate | oleth-20 |
| 45-02 | 360 | 1.0 | 10.0 | 1.25 | stearylamine | oleth-20 |
| 45-03 | 360 | 1.0 | 10.0 | 1.25 | stearyl alcohol | oleth-20 |
| 45-04 | 360 | 1.0 | 10.0 | 1.25 | docosane | oleth-20 |
| 45-05 | 360 | | 10.0 | 1.25 | none | oleth-20 |
| 45-06 | 360 | 1.0 | 10.0 | 1.25 | butyl stearate | steareth-30 |
| 45-07 | 360 | 1.0 | 10.0 | 1.25 | stearylamine | steareth-30 |
| 45-08 | 360 | 1.0 | 10.0 | 1.25 | stearyl alcohol | steareth-30 |
| 45-09 | 360 | 1.0 | 10.0 | 1.25 | docosane | steareth-30 |
| 45-10 | 360 | | 10.0 | 1.25 | none | steareth-30 |
| 45-11 | 360 | | 5.0 + 5.0 | 1.25 | none | oleth-20 + steareth-20 |
| 45-12 | 360 | | 5.0 + 5.0 | 1.25 | none | oleth-20 + steareth-30 |
| 45-13 | 360 | | 5.0 + 5.0 | 1.25 | none | oleth-20 + ceteareth-27 |
| 45-14 | 360 | | 5.0 + 5.0 | 1.25 | none | oleth-20 + ceteareth-15 |
| 45-15 | 360 | | 5.0 + 5.0 | 1.25 | none | steareth-30 + steareth-20 |
| 45-16 | 360 | | 5.0 + 5.0 | 1.25 | none | steareth-30 + ceteareth-27 |
| 45-17 | 360 | | 5.0 + 5.0 | 1.25 | none | steareth-30 + ceteareth-15 |
| 45-18 | 360 | | 10.0 | 1.25 | none | laureth-23 |

Velvetleaf (*Abutilon theophrasti*, *ABUTH*) and Japanese millet (*Echinochloa crus-galli*, *ECHCF*) plants were grown and treated by the standard procedures given above. Applications of spray compositions were made 17 days after planting *ABUTH* and *ECHCF*, and evaluation of herbicidal inhibition was done 19 days after application.

Formulations B and J were applied as comparative treatments. Results, averaged for all replicates of each treatment, are shown in Table 45b.

TABLE 45b

| Concentrate composition | Glyphosate rate g a.e./ha | % Inhibition ABUTH | ECHCF |
|---|---|---|---|
| Formulation B | 100 | 0 | 60 |
| | 200 | 15 | 73 |
| | 300 | 33 | 88 |
| | 400 | 57 | 91 |
| Formulation J | 100 | 5 | 70 |
| | 200 | 37 | 92 |
| | 300 | 80 | 99 |
| | 400 | 77 | 96 |
| 45-01 | 100 | 13 | 88 |
| | 200 | 32 | 85 |
| | 300 | 48 | 98 |
| | 400 | 90 | 93 |
| 45-02 | 100 | 10 | 70 |
| | 200 | 45 | 98 |
| | 300 | 72 | 99 |
| | 400 | 80 | 98 |
| 45-03 | 100 | 3 | 77 |
| | 200 | 25 | 94 |
| | 300 | 47 | 98 |
| | 400 | 75 | 99 |
| 45-04 | 100 | 7 | 67 |
| | 200 | 23 | 94 |
| | 300 | 40 | 99 |
| | 400 | 7 | 47 |
| 45-05 | 100 | 7 | 76 |
| | 200 | 25 | 88 |
| | 300 | 45 | 96 |
| | 400 | 75 | 97 |
| 45-06 | 100 | 12 | 96 |
| | 200 | 30 | 97 |
| | 300 | 45 | 98 |
| | 400 | 15 | 60 |
| 45-07 | 100 | 8 | 83 |
| | 200 | 12 | 97 |
| | 300 | 35 | 94 |
| | 400 | 50 | 98 |
| 45-08 | 100 | 15 | 72 |
| | 200 | 30 | 88 |
| | 300 | 40 | 99 |
| | 400 | 0 | 33 |
| 45-09 | 100 | 5 | 73 |
| | 200 | 15 | 94 |
| | 300 | 47 | 99 |
| | 400 | 5 | 53 |
| 45-10 | 100 | 7 | 79 |
| | 200 | 15 | 95 |
| | 300 | 45 | 98 |
| | 400 | 62 | 99 |
| 45-11 | 100 | 5 | 84 |
| | 200 | 13 | 98 |
| | 300 | 30 | 98 |
| | 400 | 55 | 100 |
| 45-12 | 100 | 3 | 95 |
| | 200 | 17 | 99 |
| | 300 | 28 | 99 |
| | 400 | 67 | 100 |
| 45-13 | 100 | 5 | 90 |
| | 200 | 17 | 99 |
| | 300 | 30 | 100 |
| | 400 | 60 | 98 |
| 45-14 | 100 | 3 | 98 |
| | 200 | 25 | 97 |
| | 300 | 38 | 100 |
| | 400 | 57 | 100 |
| 45-15 | 100 | 5 | 97 |
| | 200 | 25 | 97 |
| | 300 | 40 | 100 |
| | 400 | 40 | 99 |
| 45-16 | 100 | 10 | 97 |
| | 200 | 15 | 98 |

TABLE 45b-continued

| Concentrate composition | Glyphosate rate g a.e./ha | % Inhibition ABUTH | % Inhibition ECHCF |
|---|---|---|---|
| | 300 | 52 | 100 |
| | 400 | 0 | 47 |
| 45-17 | 100 | 7 | 97 |
| | 200 | 25 | 94 |
| | 300 | 40 | 98 |
| | 400 | 33 | 97 |
| 45-18 | 100 | 7 | 96 |
| | 200 | 25 | 99 |
| | 300 | 55 | 100 |
| | 400 | 73 | 100 |

Percent inhibition data for the 400 g a.e./ha glyphosate rate in this test are unreliable and should be ignored. Neither oleth-20 (composition 45-05) nor steareth-20 (45-10) provided herbicidal effectiveness equal to Formulation J in this study, and no great or consistent further enhancement was obtained by adding butyl stearate.

Example 46

Aqueous concentrate compositions were prepared containing glyphosate IPA salt and excipient ingredients as shown in Table 46a. Concentrate compositions 46-01 to 46-03 are oil-in-water emulsions and were prepared by process (vii). Compositions 46-04 to 46-18 all contain colloidal particulates and were prepared by process (ix). Different mixing methods were employed in the final stage of preparation of these compositions, as indicated in the column of Table 46a headed "Process".

The compositions of this example all showed acceptable storage stability. The compositions shown as containing colloidal particulate were not storage-stable unless the colloidal particulate was included as shown.

TABLE 46a

| Concentrate composition | Glyphosate g a.e./l | % w/w Butyl stearate | % w/w Surfactant | Aerosil 380 | Type of surfactant | Process(*) |
|---|---|---|---|---|---|---|
| 46-01 | 163 | 0.5 | 5.0 | | oleth-20 | |
| 46-02 | 163 | 0.5 | 5.0 | | steareth-20 | |
| 46-03 | 163 | 0.5 | 5.0 | | ceteareth-27 | |
| 46-04 | 360 | 1.0 | 10.0 | 1.25 | ceteareth-15 | A |
| 46-05 | 360 | 1.0 | 10.0 | 1.25 | ceteth-20 | A |
| 46-06 | 360 | 1.0 | 10.0 | 1.25 | steareth-20 | A |
| 46-07 | 360 | 1.0 | 10.0 | 1.25 | oleth-20 | A |
| 46-08 | 360 | 1.0 | 10.0 | 1.25 | ceteareth-27 | A |
| 46-09 | 360 | 1.0 | 10.0 | 1.25 | steareth-30 | A |
| 46-10 | 360 | | 10.0 | 1.25 | steareth-30 | A |
| 46-11 | 360 | 1.0 | 10.0 | 1.25 | oleth-20 | A |
| 46-12 | 360 | 1.0 | 10.0 | 1.25 | oleth-20 | B |
| 46-13 | 360 | 1.0 | 10.0 | 1.25 | oleth-20 | C |
| 46-14 | 360 | 1.0 | 10.0 | 1.25 | oleth-20 | D |

TABLE 46a-continued

| Concentrate composition | Glyphosate g a.e./l | % w/w Butyl stearate | % w/w Surfactant | Aerosil 380 | Type of surfactant | Process(*) |
|---|---|---|---|---|---|---|
| 46-15 | 360 | 1.0 | 10.0 | 1.25 | oleth-20 | E |
| 46-16 | 360 | 1.0 | 10.0 | 1.25 | oleth-20 | F |
| 46-17 | 360 | 1.0 | 10.0 | 1.25 | oleth-20 | G |
| 46-18 | 360 | 1.0 | 10.0 | 1.25 | oleth-20 | A |

(*) Process:
A Silverson mixer, medium screen, 3 minutes at 7000 rpm
B Silverson mixer, coarse screen, 3 minutes at 7000 rpm
C Fann mixer, 50% output, 5 minutes
D Turrax mixer, 3 minutes at 8000 rpm
E Overhead stirrer, low speed
F Overhead stirrer, high speed
G Hand shaking, 3 minutes Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting *ABUTH* and *ECHCF*, and evaluation of herbicidal inhibition was done 19 days after application.

Formulations B and J were applied as comparative treatments. Results, averaged for all replicates of each treatment, are shown in Table 46b.

TABLE 46b

| Concentrate composition | Glyphosate rate g a.e./ha | % Inhibition ABUTH | % Inhibition ECHCF |
|---|---|---|---|
| Formulation B | 100 | 20 | 40 |
| | 200 | 45 | 50 |
| | 300 | 65 | 72 |
| | 400 | 78 | 85 |
| Formulation J | 100 | 43 | 53 |
| | 200 | 80 | 80 |
| | 300 | 96 | 82 |
| | 400 | 99 | 94 |
| 46-01 | 100 | 45 | 57 |
| | 200 | 80 | 72 |
| | 300 | 89 | 78 |
| | 400 | 98 | 83 |
| 46-02 | 100 | 53 | 57 |
| | 200 | 80 | 78 |
| | 300 | 89 | 77 |
| | 400 | 93 | 83 |
| 46-03 | 100 | 45 | 60 |
| | 200 | 83 | 75 |
| | 300 | 97 | 73 |
| | 400 | 97 | 85 |
| 46-04 | 100 | 45 | 45 |
| | 200 | 80 | 80 |
| | 300 | 83 | 83 |
| | 400 | 95 | 95 |
| 46-05 | 100 | 42 | 42 |
| | 200 | 77 | 77 |
| | 300 | 93 | 93 |
| | 400 | 98 | 98 |
| 46-06 | 100 | 30 | 30 |
| | 200 | 42 | 42 |
| | 300 | 27 | 30 |
| | 400 | 3 | 20 |
| 46-07 | 100 | 40 | 40 |
| | 200 | 77 | 75 |
| | 300 | 90 | 93 |
| | 400 | 97 | 86 |
| 46-08 | 100 | 43 | 50 |
| | 200 | 80 | 80 |

TABLE 46b-continued

| Concentrate composition | Glyphosate rate g a.e./ha | % Inhibition ABUTH | ECHCF |
|---|---|---|---|
| | 300 | 92 | 93 |
| | 400 | 96 | 98 |
| 46-09 | 100 | 0 | 2 |
| | 200 | 82 | 75 |
| | 300 | 83 | 96 |
| | 400 | 90 | 88 |
| 46-10 | 100 | 57 | 60 |
| | 200 | 80 | 70 |
| | 300 | 88 | 88 |
| | 400 | 95 | 93 |
| 46-11 | 100 | 35 | 47 |
| | 200 | 72 | 75 |
| | 300 | 80 | 75 |
| | 400 | 85 | 77 |
| 46-12 | 100 | 47 | 47 |
| | 200 | 72 | 77 |
| | 300 | 80 | 90 |
| | 400 | 86 | 78 |
| 46-13 | 100 | 55 | 50 |
| | 200 | 75 | 83 |
| | 300 | 78 | 92 |
| | 400 | 91 | 92 |
| 46-14 | 100 | 52 | 50 |
| | 200 | 75 | 78 |
| | 300 | 83 | 88 |
| | 400 | 99 | 92 |
| 46-15 | 100 | 47 | 47 |
| | 200 | 70 | 73 |
| | 300 | 87 | 87 |
| | 400 | 75 | 63 |
| 46-16 | 100 | 43 | 40 |
| | 200 | 78 | 75 |
| | 300 | 88 | 88 |
| | 400 | 87 | 91 |
| 46-17 | 100 | 43 | 43 |
| | 200 | 67 | 88 |
| | 300 | 80 | 75 |
| | 400 | 92 | 83 |
| 46-18 | 100 | 27 | 40 |
| | 200 | 63 | 57 |
| | 300 | 82 | 73 |
| | 400 | 87 | 70 |

Results obtained with composition 46-06 are out of line with other data in this Example and an error in formulation or application is suspected. Some differences in herbicidal effectiveness were evident when a composition containing 360 g a.e./l glyphosate, 1% butyl stearate, 10% oleth-20 and 1.25% Aerosil 380 was processed in different ways (46-11 to 46-17). However, as compositions 46-07 and 46-11 were identically processed yet differed in effectiveness, no firm conclusions can be drawn from this test.

Example 47

Aqueous concentrate compositions were prepared containing glyphosate IPA salt and excipient ingredients as shown in Table 47a. Concentrate compositions 47-01 to 47-09 are aqueous solution concentrates and were prepared by process (viii). Concentrate compositions 47-10 to 47-18 are aqueous solution concentrates containing colloidal particulates and were prepared by process (ix).

Compositions of this example containing 3% or 6% surfactant were not acceptably storage-stable except in the presence of colloidal particulate as shown.

TABLE 47a

| Composition no. | Glyphosate g a.e./l | % w/w Steareth-20 | Oleth-20 | Velvetex AB-45 | Aerosil | Type of Aerosil |
|---|---|---|---|---|---|---|
| 47-01 | 488 | 1.0 | | | | none |
| 47-02 | 488 | 3.0 | | | | none |
| 47-03 | 488 | 6.0 | | | | none |
| 47-04 | 488 | | 1.0 | | | none |
| 47-05 | 488 | | 3.0 | | | none |
| 47-06 | 488 | | 6.0 | | | none |
| 47-07 | 488 | | | 1.0 | | none |
| 47-08 | 488 | | | 3.0 | | none |
| 47-09 | 488 | | | 4.6 | | none |
| 47-10 | 488 | 1.0 | | | 1.5 | MOX-80/MOX-170 (1:1) |
| 47-11 | 488 | 3.0 | | | 1.5 | MOX-80/MOX-170 (1:1) |
| 47-12 | 488 | 6.0 | | | 1.5 | MOX-80/MOX-170 (1:1) |
| 47-13 | 488 | | 1.0 | | 1.5 | MOX-80/MOX-170 (1:1) |
| 47-14 | 488 | | 3.0 | | 1.5 | MOX-80/MOX-170 (1:1) |
| 47-15 | 488 | | 6.0 | | 1.5 | MOX-80/MOX-170 (1:1) |
| 47-16 | 488 | | | 1.0 | 1.5 | MOX-80/MOX-170 (1:1) |
| 47-17 | 488 | | | 3.0 | 1.5 | MOX-80/MOX-170 (1:1) |
| 47-18 | 488 | | | 4.6 | 1.5 | MOX-80/MOX-170 (1:1) |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and ECHCF, and evaluation of herbicidal inhibition was done 18 days after application.

Formulations B and J were applied as comparative treatments. Results, averaged for all replicates of each treatment, are shown in Table 47b.

TABLE 47b

| Concentrate composition | Glyphosate rate g a.e./ha | % Inhibition ABUTH | ECHCF |
|---|---|---|---|
| Formulation B | 100 | 10 | 40 |
| | 200 | 38 | 67 |
| | 300 | 70 | 80 |
| | 400 | 86 | 92 |
| Formulation J | 100 | 43 | 58 |
| | 200 | 65 | 82 |
| | 300 | 91 | 94 |
| | 400 | 100 | 95 |
| 47-01 | 100 | 23 | 60 |
| | 200 | 40 | 65 |
| | 300 | 73 | 87 |
| | 400 | 80 | 92 |
| 47-02 | 100 | 38 | 67 |
| | 200 | 77 | 82 |
| | 300 | 95 | 83 |

TABLE 47b-continued

| Concentrate composition | Glyphosate rate g a.e./ha | % Inhibition ABUTH | % Inhibition ECHCF |
|---|---|---|---|
| | 400 | 99 | 93 |
| 47-03 | 100 | 33 | 67 |
| | 200 | 78 | 73 |
| | 300 | 90 | 94 |
| | 400 | 100 | 96 |
| 47-04 | 100 | 23 | 63 |
| | 200 | 48 | 81 |
| | 300 | 68 | 87 |
| | 400 | 72 | 88 |
| 47-05 | 100 | 30 | 63 |
| | 200 | 63 | 80 |
| | 300 | 78 | 89 |
| | 400 | 95 | 93 |
| 47-06 | 100 | 25 | 85 |
| | 200 | 68 | 93 |
| | 300 | 77 | 93 |
| | 400 | 99 | 95 |
| 47-07 | 100 | 13 | 60 |
| | 200 | 42 | 80 |
| | 300 | 57 | 95 |
| | 400 | 92 | 96 |
| 47-08 | 100 | 20 | 73 |
| | 200 | 43 | 92 |
| | 300 | 83 | 93 |
| | 400 | 72 | 96 |
| 47-09 | 100 | 30 | 73 |
| | 200 | 50 | 94 |
| | 300 | 65 | 96 |
| | 400 | 75 | 98 |
| 47-10 | 100 | 10 | 65 |
| | 200 | 53 | 88 |
| | 300 | 72 | 94 |
| | 400 | 83 | 95 |
| 47-11 | 100 | 15 | 50 |
| | 200 | 57 | 77 |
| | 300 | 82 | 95 |
| | 400 | 92 | 97 |
| 47-12 | 100 | 30 | 70 |
| | 200 | 68 | 98 |
| | 300 | 78 | 97 |
| | 400 | 96 | 98 |
| 47-13 | 100 | 15 | 77 |
| | 200 | 43 | 93 |
| | 300 | 68 | 95 |
| | 400 | 77 | 99 |
| 47-14 | 100 | 10 | 73 |
| | 200 | 40 | 93 |
| | 300 | 68 | 98 |
| | 400 | 78 | 98 |
| 47-15 | 100 | missing | missing |
| | 200 | missing | missing |
| | 300 | missing | missing |
| | 400 | missing | missing |
| 47-16 | 100 | 0 | 60 |
| | 200 | 30 | 93 |
| | 300 | 40 | 99 |
| | 400 | 50 | 99 |
| 47-17 | 100 | 2 | 83 |
| | 200 | 43 | 99 |
| | 300 | 67 | 100 |
| | 400 | 67 | 100 |
| 47-18 | 100 | 5 | 95 |
| | 200 | 37 | 100 |
| | 300 | 60 | 100 |
| | 400 | 78 | 100 |

In high-load (488 g a.e./l) glyphosate compositions, steareth-20 at 3% or 6% provided greater herbicidal effectiveness in this test than the same concentrations of oleth-20. Even at just 3%, steareth-20 (composition 47-02) gave effectiveness equal to commercial standard Formulation J. Addition of a blend of colloidal particulates to stabilize the composition (47-11) slightly reduced effectiveness in this study.

Example 48

Aqueous concentrate compositions were prepared containing glyphosate IPA salt and excipient ingredients as shown in Table 48a. Concentrate compositions 48-01 to 48-04 are aqueous solution concentrates and were prepared by process (viii). Concentrate compositions 48-08 to 48-18 are aqueous solution concentrates containing colloidal particulates and were prepared by process (ix). Concentrate compositions 48-05 to 48-07 contain colloidal particulate but no surfactant.

All compositions of this example except 48-01 to 48-03 were acceptably storage-stable.

TABLE 48a

| Concentrate composition | Glyphosate g a.e./l | % w/w Steareth-20 | % w/w Steareth-100 | % w/w MON 0818 | Aerosil | Type of Aerosil |
|---|---|---|---|---|---|---|
| 48-01 | 488 | 3.0 | | | | |
| 48-02 | 488 | 4.5 | | | | |
| 48-03 | 488 | 6.0 | | | | |
| 48-04 | 488 | | 3.0 | | | |
| 48-05 | 488 | | | | 1.5 | 380 |
| 48-06 | 488 | | | | 1.5 | MOX-80/MOX-170 (1:1) |
| 48-07 | 488 | | | | 3.0 | MOX-80/380 (1:1) |
| 48-08 | 488 | | 1.5 | | | |
| 48-09 | 488 | 3.0 | | 3.0 | 1.5 | 380 |
| 48-10 | 488 | 4.5 | | 3.0 | 1.5 | 380 |
| 48-11 | 488 | 6.0 | | 3.0 | 1.5 | 380 |
| 48-12 | 488 | 3.0 | | 3.0 | 1.5 | MOX-80/MOX-170 (1:1) |
| 48-13 | 488 | 4.5 | | 3.0 | 1.5 | MOX-80/MOX-170 (1:1) |
| 48-14 | 488 | 6.0 | | 3.0 | 1.5 | MOX-80/MOX-170 (1:1) |
| 48-15 | 488 | 3.0 | | 3.0 | 1.5 | MOX-80/380 (1:1) |
| 48-16 | 488 | 4.5 | | 3.0 | 1.5 | MOX-80/380 (1:1) |
| 48-17 | 488 | 6.0 | | 3.0 | 1.5 | MOX-80/380 (1:1) |
| 48-18 | 488 | | 4.5 | 3.0 | 1.5 | MOX-80/MOX-170 (1:1) |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 21 days after application.

Formulations B and J were applied as comparative treatments. Results, averaged for all replicates of each treatment, are shown in Table 48b.

TABLE 48b

| Concentrate composition | Glyphosate rate g a.e./ha | % Inhibition ABUTH | % Inhibition ECHCF |
|---|---|---|---|
| Formulation B | 100 | 2 | 23 |
| | 200 | 18 | 50 |
| | 300 | 42 | 67 |
| | 400 | 63 | 80 |
| Formulation J | 100 | 20 | 47 |
| | 200 | 40 | 86 |
| | 300 | 83 | 98 |
| | 400 | 93 | 98 |
| 48-01 | 100 | 10 | 75 |
| | 200 | 62 | 83 |
| | 300 | 80 | 96 |
| | 400 | 93 | 99 |
| 48-02 | 100 | 40 | 60 |
| | 200 | 77 | 92 |
| | 300 | 87 | 97 |
| | 400 | 93 | 99 |
| 48-03 | 100 | 23 | 40 |
| | 200 | 38 | 63 |
| | 300 | 78 | 91 |
| | 400 | 97 | 91 |
| 48-04 | 100 | 20 | 38 |
| | 200 | 23 | 77 |
| | 300 | 43 | 94 |
| | 400 | 73 | 94 |
| 48-05 | 100 | 7 | 30 |
| | 200 | 25 | 37 |
| | 300 | 42 | 60 |
| | 400 | 67 | 63 |
| 48-06 | 100 | 7 | 30 |
| | 200 | 20 | 53 |
| | 300 | 52 | 67 |
| | 400 | 83 | 67 |
| 48-07 | 100 | 5 | 35 |
| | 200 | 20 | 63 |
| | 300 | 57 | 80 |
| | 400 | 43 | 85 |
| 48-08 | 100 | 22 | 83 |
| | 200 | 47 | 99 |
| | 300 | 86 | 98 |
| | 400 | 78 | 100 |
| 48-09 | 100 | 12 | 45 |
| | 200 | 25 | 77 |
| | 300 | 40 | 83 |
| | 400 | 37 | 95 |
| 48-10 | 100 | 13 | 53 |
| | 200 | 73 | 99 |
| | 300 | 85 | 98 |
| | 400 | 99 | 99 |
| 48-11 | 100 | 25 | 50 |
| | 200 | 60 | 88 |
| | 300 | 93 | 99 |
| | 400 | 99 | 99 |
| 48-12 | 100 | 25 | 45 |
| | 200 | 57 | 88 |
| | 300 | 85 | 97 |
| | 400 | 100 | 94 |
| 48-13 | 100 | 30 | 52 |
| | 200 | 68 | 87 |
| | 300 | 93 | 99 |
| | 400 | 100 | 92 |
| 48-14 | 100 | 40 | 45 |
| | 200 | 73 | 88 |
| | 300 | 81 | 98 |
| | 400 | 100 | 99 |
| 48-15 | 100 | 8 | 57 |
| | 200 | 33 | 96 |
| | 300 | 81 | 99 |
| | 400 | 95 | 99 |
| 48-16 | 100 | 10 | 62 |
| | 200 | 48 | 83 |
| | 300 | 99 | 98 |
| | 400 | 100 | 100 |
| 48-17 | 100 | 27 | 58 |
| | 200 | 65 | 92 |
| | 300 | 75 | 98 |
| | 400 | 93 | 99 |
| 48-18 | 100 | 5 | 40 |
| | 200 | 33 | 87 |
| | 300 | 55 | 98 |
| | 400 | 75 | 98 |

Among stabilized high-load (488 g a.e./l) glyphosate compositions providing herbicidal effectiveness superior to commercial standard Formulation J, at least on ABUTH, were 48-10 and 48-11 (respectively 4.5% and 6% steareth-20+3% MON 0818+1.5% Aerosil 380), 48-13 (4.5% steareth-20+3% MON 0818+1.5% Aerosil MOX-80/MOX-170 blend) and 48-16 (4.5% steareth-20+3% MON 0818+ 1.5% Aerosil MOX-80/380 blend). The relatively poor performance of composition 48-04 and the good performance of composition 48-02 shows that the excellent results obtained with the stabilized compositions listed above are primarily attributable to the steareth-20 component.

Example 49

Aqueous concentrate compositions were prepared containing glyphosate IPA salt and excipient ingredients as shown in Table 49a. Concentrate compositions 49-01 to 49-09 are aqueous solution concentrates and were prepared by process (viii). Concentrate compositions 49-10 to 49-18 are aqueous solution concentrates containing colloidal particulates and were prepared by process (ix).

Compositions of this example containing 3% or 6% surfactant were not acceptably storage-stable except in the presence of colloidal particulate as shown.

TABLE 49a

| Concentrate composition | Glyphosate g a.e./l | % w/w Steareth-20 | % w/w Oleth-20 | % w/w Velvetex AB-45 | Aerosil | Type of Aerosil |
|---|---|---|---|---|---|---|
| 49-01 | 488 | 1.5 | | | | none |
| 49-02 | 488 | 3.0 | | | | none |
| 49-03 | 488 | 6.0 | | | | none |
| 49-04 | 488 | | 1.5 | | | none |
| 49-05 | 488 | | 3.0 | | | none |
| 49-06 | 488 | | 6.0 | | | none |
| 49-07 | 488 | | | 1.5 | | none |
| 49-08 | 488 | | | 3.0 | | none |
| 49-09 | 488 | | | 4.5 | | none |
| 49-10 | 488 | 1.5 | | | 1.5 | MOX-80/380 (1:1) |
| 49-11 | 488 | 3.0 | | | 1.5 | MOX-80/380 (1:1) |
| 49-12 | 488 | 6.0 | | | 1.5 | MOX-80/380 (1:1) |
| 49-13 | 488 | | 1.5 | | 1.5 | MOX-80/380 (1:1) |
| 49-14 | 488 | | 3.0 | | 1.5 | MOX-80/380 (1:1) |
| 49-15 | 488 | | 6.0 | | 1.5 | MOX-80/380 (1:1) |

TABLE 49a-continued

| Concentrate composition | Glyphosate g a.e./l | Steareth-20 | Oleth-20 | Velvetex AB-45 | Aerosil | Type of Aerosil |
|---|---|---|---|---|---|---|
| 49-16 | 488 | | | 1.5 | 1.5 | MOX-80/380 (1:1) |
| 49-17 | 488 | | | 3.0 | 1.5 | MOX-80/380 (1:1) |
| 49-18 | 488 | | | 4.5 | 1.5 | MOX-80/380 (1:1) |

Velvetleaf (*Abutilon theophrasti*, ABUTH) and Japanese millet (*Echinochloa crus-galli*, ECHCF) plants were grown and treated by the standard procedures given above. Applications of spray compositions were made 15 days after planting ABUTH and ECHCF, and evaluation of herbicidal inhibition was done 22 days after application.

Formulations B and J were applied as comparative treatments. Results, averaged for all replicates of each treatment, are shown in Table 49b.

TABLE 49b

| Concentrate composition | Glyphosate rate g a.e./ha | % Inhibition ABUTH | ECHCF |
|---|---|---|---|
| Formulation B | 100 | 0 | 10 |
| | 200 | 3 | 27 |
| | 300 | 13 | 30 |
| | 400 | 33 | 40 |
| Formulation J | 100 | 2 | 53 |
| | 200 | 30 | 97 |
| | 300 | 70 | 99 |
| | 400 | 80 | 99 |
| 49-01 | 100 | 5 | 67 |
| | 200 | 30 | 89 |
| | 300 | 58 | 98 |
| | 400 | 80 | 100 |
| 49-02 | 100 | 20 | 60 |
| | 200 | 45 | 90 |
| | 300 | 78 | 99 |
| | 400 | 80 | 100 |
| 49-03 | 100 | 20 | 57 |
| | 200 | 47 | 93 |
| | 300 | 78 | 96 |
| | 400 | 83 | 98 |
| 49-04 | 100 | 3 | 57 |
| | 200 | 30 | 83 |
| | 300 | 63 | 99 |
| | 400 | 82 | 98 |
| 49-05 | 100 | 5 | 53 |
| | 200 | 27 | 83 |
| | 300 | 47 | 98 |
| | 400 | 77 | 100 |
| 49-06 | 100 | 5 | 40 |
| | 200 | 23 | 70 |
| | 300 | 47 | 92 |
| | 400 | 77 | 99 |
| 49-07 | 100 | 3 | 53 |
| | 200 | 30 | 85 |
| | 300 | 60 | 94 |
| | 400 | 72 | 97 |
| 49-08 | 100 | 3 | 50 |
| | 200 | 22 | 88 |
| | 300 | 53 | 97 |
| | 400 | 80 | 100 |
| 49-09 | 100 | 0 | 40 |
| | 200 | 20 | 83 |
| | 300 | 40 | 99 |
| | 400 | 67 | 99 |

TABLE 49b-continued

| Concentrate composition | Glyphosate rate g a.e./ha | % Inhibition ABUTH | ECHCF |
|---|---|---|---|
| 49-10 | 100 | 0 | 40 |
| | 200 | 27 | 60 |
| | 300 | 47 | 83 |
| | 400 | 78 | 94 |
| 49-11 | 100 | 5 | 47 |
| | 200 | 25 | 77 |
| | 300 | 57 | 96 |
| | 400 | 87 | 97 |
| 49-12 | 100 | 15 | 43 |
| | 200 | 52 | 88 |
| | 300 | 87 | 98 |
| | 400 | 87 | 98 |
| 49-13 | 100 | 0 | 40 |
| | 200 | 17 | 70 |
| | 300 | 35 | 83 |
| | 400 | 53 | 88 |
| 49-14 | 100 | 0 | 33 |
| | 200 | 18 | 67 |
| | 300 | 28 | 90 |
| | 400 | 62 | 98 |
| 49-15 | 100 | 2 | 33 |
| | 200 | 25 | 70 |
| | 300 | 53 | 85 |
| | 400 | 72 | 97 |
| 49-16 | 100 | 0 | 30 |
| | 200 | 17 | 50 |
| | 300 | 27 | 67 |
| | 400 | 72 | 87 |
| 49-17 | 100 | 0 | 0 |
| | 200 | 7 | 63 |
| | 300 | 32 | 88 |
| | 400 | 47 | 90 |
| 49-18 | 100 | 0 | 5 |
| | 200 | 12 | 60 |
| | 300 | 25 | 83 |
| | 400 | 45 | 97 |

Compositions containing steareth-20 generally performed better than counterparts containing oleth-20 in this study, both in the presence and in the absence of colloidal particulates.

Example 50

Aqueous concentrate compositions were prepared containing glyphosate IPA salt and excipient ingredients as shown in Table 50a. All contain colloidal particulates and were prepared by process (ix).

The compositions of this example all showed acceptable storage stability. The compositions shown as containing colloidal particulate were not storage-stable unless the colloidal particulate was included as shown.

TABLE 50a

| Concentrate composition | Glyphosate a.e. | Oil | Surfactant | Aerosil 380 | Type of oil | Type of surfactant |
|---|---|---|---|---|---|---|
| 50-01 | 31 | 1.0 | 10.0 | 1.25 | Butyl stearate | steareth-20 |
| 50-02 | 31 | 1.0 | 10.0 | 1.25 | Butyl stearate | oleth-20 |

TABLE 50a-continued

| Concentrate composition | Gly-phosate a.e. | Oil | Sur-factant | Aerosil 380 | Type of oil | Type of surfactant |
|---|---|---|---|---|---|---|
| 50-03 | 31 | 1.0 | 10.0 | 1.25 | Butyl stearate | steareth-30 |
| 50-04 | 31 | | 10.0 | 1.25 | none | steareth-30 |

Velvetleaf (*Abutilon theophrasti*, ABUTH) and Japanese millet (*Echinochloa crus-galli*, ECHCF) plants were grown and treated by the standard procedures given above. Treatments were applied at four different hours of the day. Applications of spray compositions were made 16 days after planting ABUTH and ECHCF, and evaluation of herbicidal inhibition was done 22 days after application.

Formulation J was applied as a comparative treatment. Results, averaged for all replicates of each treatment, are shown in Table 50b.

TABLE 50b

| Concentrate composition | Hour when applied | Glyphosate rate g a.e./ha | % Inhibition ABUTH | % Inhibition ECHCF |
|---|---|---|---|---|
| Formulation J | 1000 | 100 | 5 | 33 |
| | | 200 | 42 | 75 |
| | | 300 | 67 | 83 |
| | | 400 | 77 | 93 |
| 50-01 | 1000 | 100 | 7 | 33 |
| | | 200 | 40 | 70 |
| | | 300 | 50 | 82 |
| | | 400 | 78 | 91 |
| 50-02 | 1000 | 100 | 18 | 33 |
| | | 200 | 37 | 73 |
| | | 300 | 48 | 91 |
| | | 400 | 80 | 92 |
| 50-03 | 1000 | 100 | 30 | 33 |
| | | 200 | 40 | 75 |
| | | 300 | 82 | 85 |
| | | 400 | 83 | 80 |
| 50-04 | 1000 | 100 | 30 | 30 |
| | | 200 | 43 | 78 |
| | | 300 | 78 | 92 |
| | | 400 | 93 | 95 |
| Formulation J | 1200 | 100 | 5 | 38 |
| | | 200 | 35 | 87 |
| | | 300 | 53 | 96 |
| | | 400 | 88 | 99 |
| 50-01 | 1200 | 100 | 10 | 30 |
| | | 200 | 47 | 91 |
| | | 300 | 70 | 89 |
| | | 400 | 78 | 97 |
| 50-02 | 1200 | 100 | 5 | 37 |
| | | 200 | 40 | 75 |
| | | 300 | 48 | 87 |
| | | 400 | 70 | 94 |
| 50-03 | 1200 | 100 | 20 | 37 |
| | | 200 | 50 | 82 |
| | | 300 | 78 | 98 |
| | | 400 | 83 | 97 |
| 50-04 | 1200 | 100 | 33 | 33 |
| | | 200 | 45 | 93 |
| | | 300 | 75 | 98 |
| | | 400 | 95 | 100 |
| Formulation J | 1400 | 100 | 15 | 40 |
| | | 200 | 30 | 90 |
| | | 300 | 55 | 100 |
| | | 400 | 80 | 100 |
| 50-01 | 1400 | 100 | 17 | 40 |
| | | 200 | 45 | 70 |
| | | 300 | 75 | 97 |
| | | 400 | 80 | 98 |
| 50-02 | 1400 | 100 | 17 | 47 |
| | | 200 | 35 | 83 |
| | | 300 | 67 | 97 |
| | | 400 | 63 | 97 |
| 50-03 | 1400 | 100 | 30 | 40 |
| | | 200 | 63 | 80 |
| | | 300 | 77 | 97 |
| | | 400 | 78 | 100 |
| 50-04 | 1400 | 100 | 23 | 40 |
| | | 200 | 45 | 87 |
| | | 300 | 73 | 100 |
| | | 400 | 78 | 100 |
| Formulation J | 1600 | 100 | 10 | 37 |
| | | 200 | 32 | 83 |
| | | 300 | 52 | 97 |
| | | 400 | 75 | 98 |
| 50-01 | 1600 | 100 | 27 | 43 |
| | | 200 | 40 | 89 |
| | | 300 | 77 | 99 |
| | | 400 | 95 | 99 |
| 50-02 | 1600 | 100 | 20 | 53 |
| | | 200 | 40 | 95 |
| | | 300 | 53 | 98 |
| | | 400 | 80 | 98 |
| 50-03 | 1600 | 100 | 27 | 60 |
| | | 200 | 60 | 93 |
| | | 300 | 78 | 97 |
| | | 400 | 96 | 100 |
| 50-04 | 1600 | 100 | 15 | 37 |
| | | 200 | 43 | 83 |
| | | 300 | 67 | 97 |
| | | 400 | 78 | 96 |

Composition 50-03 illustrates the consistency of high-level performance obtainable with, in this case, steareth-30 at an approximately 1:3 weight/weight ratio to glyphosate a.e., together with a small amount of butyl stearate and Aerosil 380. An average of percent inhibition of ABUTH across all four glyphosate rates shows the following comparison of 50-03 with Formulation J, applied at four different hours of the day:

| Hour | Formulation J | Composition 50-03 |
|---|---|---|
| 1000 | 48 | 59 |
| 1200 | 45 | 58 |
| 1400 | 48 | 62 |
| 1600 | 42 | 65 |

Example 51

Aqueous concentrate compositions were prepared containing glyphosate IPA salt and excipient ingredients as shown in Table 51a. Concentrate compositions 51-01 to 51-07 are aqueous solution concentrates and were prepared by process (viii). Concentrate compositions 51-08 to 51-18 are aqueous solution concentrates containing colloidal particulates and were prepared by process (ix).

Compositions 51-01 to 51-06 were not acceptably storage-stable. All other compositions showed acceptable storage stability.

TABLE 51a

| Concentrate composition | Glyphosate g a.e./l | % w/w | | | |
|---|---|---|---|---|---|
| | | Steareth-30 | Steareth-20 | Agrimul PG-2069 | Aerosil 380 |
| 51-01 | 488 | 3.00 | | | |
| 51-02 | 488 | 4.50 | | | |
| 51-03 | 488 | 6.00 | | | |
| 51-04 | 488 | | 3.00 | | |
| 51-05 | 488 | | 4.50 | | |
| 51-06 | 488 | | 6.00 | | |
| 51-07 | 488 | | | 2.0 | |
| 51-08 | 488 | 3.00 | | | 1.5 |
| 51-09 | 488 | 4.50 | | | 1.5 |
| 51-10 | 488 | 6.00 | | | 1.5 |
| 51-11 | 488 | | 3.00 | | 1.5 |
| 51-12 | 488 | | 4.50 | | 1.5 |
| 51-13 | 488 | | 6.00 | | 1.5 |
| 51-14 | 488 | 1.50 | 1.50 | | 1.5 |
| 51-15 | 488 | 2.25 | 2.25 | | 1.5 |
| 51-16 | 488 | 3.00 | 3.00 | | 1.5 |
| 51-17 | 488 | 2.25 | 2.25 | 2.0 | 1.5 |
| 51-18 | 488 | 3.00 | 3.00 | 2.0 | 1.5 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 23 days after application.

Formulations B and J were applied as comparative treatments. Results, averaged for all replicates of each treatment, are shown in Table 51b.

TABLE 51b

| Concentrate composition | Glyphosate rate g a.e./ha | % Inhibition | |
|---|---|---|---|
| | | ABUTH | ECHCF |
| Formulation B | 100 | 2 | 20 |
| | 200 | 22 | 33 |
| | 300 | 35 | 67 |
| | 400 | 68 | 73 |
| Formulation J | 100 | 32 | 63 |
| | 200 | 78 | 90 |
| | 300 | 83 | 93 |
| | 400 | 92 | 97 |
| 51-01 | 100 | 38 | 57 |
| | 200 | 50 | 63 |
| | 300 | 62 | 80 |
| | 400 | 75 | 89 |
| 51-02 | 100 | 20 | 57 |
| | 200 | 63 | 70 |
| | 300 | 75 | 88 |
| | 400 | 80 | 96 |
| 51-03 | 100 | 47 | 53 |
| | 200 | 72 | 80 |
| | 300 | 87 | 96 |
| | 400 | 100 | 99 |
| 51-04 | 100 | 33 | 30 |
| | 200 | 48 | 60 |
| | 300 | 75 | 73 |
| | 400 | 90 | 83 |
| 51-05 | 100 | 10 | 30 |
| | 200 | 43 | 50 |
| | 300 | 68 | 82 |
| | 400 | 83 | 92 |
| 51-06 | 100 | 22 | 40 |
| | 200 | 43 | 50 |
| | 300 | 75 | 83 |
| | 400 | 83 | 87 |
| 51-07 | 100 | 10 | 37 |
| | 200 | 40 | 63 |
| | 300 | 78 | 86 |
| | 400 | 95 | 96 |
| 51-08 | 100 | 23 | 43 |
| | 200 | 68 | 63 |
| | 300 | 92 | 88 |
| | 400 | 98 | 93 |
| 51-09 | 100 | 47 | 57 |
| | 200 | 78 | 70 |
| | 300 | 95 | 92 |
| | 400 | 100 | 96 |
| 51-10 | 100 | 37 | 57 |
| | 200 | 85 | 68 |
| | 300 | 92 | 85 |
| | 400 | 100 | 93 |
| 51-11 | 100 | 28 | 43 |
| | 200 | 63 | 73 |
| | 300 | 85 | 83 |
| | 400 | 95 | 96 |
| 51-12 | 100 | 40 | 53 |
| | 200 | 75 | 88 |
| | 300 | 90 | 92 |
| | 400 | 100 | 97 |
| 51-13 | 100 | 40 | 53 |
| | 200 | 75 | 75 |
| | 300 | 99 | 92 |
| | 400 | 100 | 98 |
| 51-14 | 100 | 30 | 43 |
| | 200 | 68 | 72 |
| | 300 | 83 | 82 |
| | 400 | 96 | 97 |
| 51-15 | 100 | 38 | 47 |
| | 200 | 77 | 72 |
| | 300 | 94 | 92 |
| | 400 | 100 | 96 |
| 51-16 | 100 | 33 | 43 |
| | 200 | 75 | 67 |
| | 300 | 92 | 88 |
| | 400 | 100 | 94 |
| 51-17 | 100 | 25 | 43 |
| | 200 | 68 | 82 |
| | 300 | 78 | 96 |
| | 400 | 99 | 96 |
| 51-18 | 100 | 13 | 37 |
| | 200 | 72 | 70 |
| | 300 | 87 | 80 |
| | 400 | 99 | 85 |

Several stabilized high-load (488 g a.e./l) glyphosate compositions of this Example provided herbicidal effectiveness equal or superior, at least on ABUTH, to that obtained with commercial standard Formulation J.

Example 52

Aqueous concentrate compositions were prepared containing glyphosate IPA salt and excipient ingredients as shown in Table 52a. Concentrate compositions 52-12 to 52-14 are aqueous solution concentrates and were prepared by process (viii). Concentrate compositions 52-01 to 52-11 and 52-15 to 52-17 are aqueous solution concentrates containing colloidal particulates and were prepared by process (ix).

TABLE 52a

| Conc. comp. | Glyphosate g a.e./l | Steareth-20 | Ethomeen T/25 | Propylene glycol | Aerosil | Type of Aerosil |
|---|---|---|---|---|---|---|
| 52-01 | 488 | 3.0 | | | 0.8 | 380 |
| 52-02 | 488 | 6.0 | | | 1.5 | MOX-80/ MOX-170 (1:1) |
| 52-03 | 488 | 4.5 | | | 1.5 | 380 |
| 52-04 | 488 | 4.5 | 2.25 | 0.5 | 1.5 | MOX-80/ 380 (1:2) |
| 52-05 | 488 | 4.5 | | 0.5 | 1.5 | MOX-80/ 380 (1:2) |
| 52-06 | 488 | 6.0 | | 0.5 | 1.5 | MOX-80/ 380 (1:2) |
| 52-07 | 488 | 3.0 | 1.50 | 0.5 | 1.5 | MOX-80/ 380 (1:2) |
| 52-08 | 488 | 6.0 | 3.00 | 0.5 | 1.5 | MOX-80/ 380 (1:2) |
| 52-09 | 488 | 3.0 | 1.50 | 0.5 | 1.5 | 380 |
| 52-10 | 488 | 4.5 | 2.25 | 0.5 | 1.5 | 380 |
| 52-11 | 488 | 6.0 | 3.00 | 0.5 | 1.5 | 380 |
| 52-12 | 488 | | 1.50 | 0.5 | | none |
| 52-13 | 488 | | 2.25 | 0.5 | | none |
| 52-14 | 488 | | 3.00 | 0.5 | | none |
| 52-15 | 488 | | 1.50 | 0.5 | 1.5 | MOX-80/ 380 (1:2) |
| 52-16 | 488 | | 2.25 | 0.5 | 1.5 | MOX-80/ 380 (1:2) |
| 52-17 | 488 | | 3.00 | 0.5 | 1.5 | MOX-80/ 380 (1:2) |

Velvetleaf (Abutilon theophrasti, ABUTH) and Japanese millet (Echinochloa crus-galli, ECHCF) plants were grown and treated by the standard procedures given above. Applications of spray compositions were made 16 days after planting ABUTH and ECHCF, and evaluation of herbicidal inhibition was done 20 days after application.

Formulations B and J were applied as comparative treatments. Results, averaged for all replicates of each treatment, are shown in Table 52b.

TABLE 52b

| Concentrate composition | Glyphosate rate g a.e./ha | % Inhibition ABUTH | % Inhibition ECHCF |
|---|---|---|---|
| Formulation B | 100 | 0 | 3 |
| | 200 | 10 | 12 |
| | 300 | 43 | 22 |
| | 400 | 47 | 27 |
| Formulation J | 100 | 13 | 15 |
| | 200 | 25 | 22 |
| | 300 | 58 | 53 |
| | 400 | 68 | 82 |
| 52-01 | 100 | 30 | 20 |
| | 200 | 60 | 53 |
| | 300 | 73 | 88 |
| | 400 | 87 | 96 |
| 52-02 | 100 | 40 | 23 |
| | 200 | 63 | 55 |
| | 300 | 88 | 87 |
| | 400 | 93 | 93 |
| 52-03 | 100 | 42 | 20 |
| | 200 | 72 | 55 |
| | 300 | 82 | 83 |
| | 400 | 90 | 88 |
| 52-04 | 100 | 60 | 32 |
| | 200 | 70 | 57 |
| | 300 | 90 | 88 |
| | 400 | 90 | 93 |
| 52-05 | 100 | 47 | 32 |
| | 200 | 67 | 57 |
| | 300 | 88 | 85 |
| | 400 | 94 | 88 |
| 52-06 | 100 | 33 | 37 |
| | 200 | 68 | 67 |
| | 300 | 82 | 80 |
| | 400 | 90 | 88 |
| 52-07 | 100 | 35 | 37 |
| | 200 | 67 | 70 |
| | 300 | 87 | 85 |
| | 400 | 97 | 93 |
| 52-08 | 100 | 32 | 35 |
| | 200 | 67 | 77 |
| | 300 | 85 | 92 |
| | 400 | 97 | 95 |
| 52-09 | 100 | 27 | 33 |
| | 200 | 57 | 67 |
| | 300 | 88 | 83 |
| | 400 | 93 | 95 |
| 52-10 | 100 | 13 | 33 |
| | 200 | 62 | 58 |
| | 300 | 80 | 80 |
| | 400 | 92 | 92 |
| 52-11 | 100 | 13 | 20 |
| | 200 | 60 | 57 |
| | 300 | 88 | 63 |
| | 400 | 93 | 82 |
| 52-12 | 100 | 10 | 27 |
| | 200 | 53 | 53 |
| | 300 | 70 | 67 |
| | 400 | 88 | 85 |
| 52-13 | 100 | 3 | 28 |
| | 200 | 50 | 57 |
| | 300 | 67 | 70 |
| | 400 | 90 | 82 |
| 52-14 | 100 | 3 | 28 |
| | 200 | 55 | 57 |
| | 300 | 70 | 83 |
| | 400 | 87 | 87 |
| 52-15 | 100 | 10 | 20 |
| | 200 | 58 | 43 |
| | 300 | 70 | 72 |
| | 400 | 83 | 85 |
| 52-16 | 100 | 12 | 22 |
| | 200 | 55 | 57 |
| | 300 | 73 | 77 |
| | 400 | 92 | 90 |
| 52-16 | 100 | 7 | 20 |
| | 200 | 53 | 55 |
| | 300 | 70 | 75 |
| | 400 | 85 | 88 |

Several stabilized high-load (488 g a.e./l) glyphosate compositions of this Example provided herbicidal effectiveness equal or superior, on both ABUTH and ECHCF, to that obtained with commercial standard Formulation J.

Example 53

Glyphosate-containing spray compositions were prepared by tank-mixing Formulation B with excipients as shown in Table 53.

Velvetleaf (Abutilon theophrasti, ABUTH) and Japanese millet (Echinochloa crus-galli, ECHCF) plants were grown and treated by the standard procedures given above. Appli cations of spray compositions were made 16 days after planting ABUTH and ECHCF, and evaluation of herbicidal inhibition was done 22 days after application. Results, averaged for all replicates of each treatment, are shown in Table 53.

TABLE 53

| Glyphosate composition | Glyphosate rate g a.e./ha | Additive | Ratio add./ a.e. | % Inhibition ABUTH | % Inhibition ECHCF |
|---|---|---|---|---|---|
| Formulation B | 150 | none |  | 18 | 25 |
|  | 250 |  |  | 73 | 58 |
|  | 350 |  |  | 80 | 82 |
| Formulation J | 150 | none |  | 47 | 90 |
|  | 250 |  |  | 77 | 93 |
|  | 350 |  |  | 95 | 94 |
| Formulation B | 150 | steareth-10 | 1:0.3 | 53 | 88 |
|  | 250 |  |  | 83 | 94 |
|  | 350 |  |  | 98 | 98 |
| Formulation B | 150 | steareth-10 | 1:1 | 48 | 73 |
|  | 250 |  |  | 67 | 97 |
|  | 350 |  |  | 93 | 99 |
| Formulation B | 150 | steareth-10 | 1:1.5 | 52 | 60 |
|  | 250 |  |  | 65 | 95 |
|  | 350 |  |  | 86 | 99 |
| Formulation B | 150 | steareth-10 | 1:3 | 48 | 73 |
|  | 250 |  |  | 65 | 83 |
|  | 350 |  |  | 80 | 98 |
| Formulation B | 150 | steareth-10 | 1:6 | 50 | 81 |
|  | 250 |  |  | 60 | 87 |
|  | 350 |  |  | 85 | 97 |
| Formulation B | 150 | steareth-20 | 1:0.3 | 76 | 92 |
|  | 250 |  |  | 100 | 93 |
|  | 350 |  |  | 100 | 99 |
| Formulation B | 150 | steareth-20 | 1:1 | 65 | 75 |
|  | 250 |  |  | 94 | 96 |
|  | 350 |  |  | 99 | 99 |
| Formulation B | 150 | steareth-20 | 1:1.5 | 52 | 95 |
|  | 250 |  |  | 84 | 92 |
|  | 350 |  |  | 98 | 98 |
| Formulation B | 150 | steareth-20 | 1:3 | 53 | 82 |
|  | 250 |  |  | 82 | 100 |
|  | 350 |  |  | 98 | 93 |
| Formulation B | 150 | steareth-20 | 1:6 | 47 | 62 |
|  | 250 |  |  | 68 | 93 |
|  | 350 |  |  | 92 | 97 |
| Formulation B | 150 | steareth-30 | 1:0.3 | 63 | 88 |
|  | 250 |  |  | 97 | 100 |
|  | 350 |  |  | 100 | 100 |
| Formulation B | 150 | steareth-30 | 1:1 | 53 | 72 |
|  | 250 |  |  | 88 | 96 |
|  | 350 |  |  | 97 | 97 |
| Formulation B | 150 | steareth-30 | 1:1.5 | 50 | 79 |
|  | 250 |  |  | 81 | 89 |
|  | 350 |  |  | 96 | 100 |
| Formulation B | 150 | steareth-30 | 1:3 | 50 | 67 |
|  | 250 |  |  | 78 | 88 |
|  | 350 |  |  | 97 | 91 |
| Formulation B | 150 | steareth-30 | 1:6 | 47 | 58 |
|  | 250 |  |  | 75 | 99 |
|  | 350 |  |  | 89 | 99 |
| Formulation B | 150 | ceteareth-30 | 1:0.3 | 55 | 86 |
|  | 250 |  |  | 89 | 91 |
|  | 350 |  |  | 99 | 100 |
| Formulation B | 150 | ceteareth-30 | 1:1 | 50 | 86 |
|  | 250 |  |  | 85 | 95 |
|  | 350 |  |  | 97 | 100 |
| Formulation B | 150 | ceteareth-30 | 1:1.5 | 43 | 75 |
|  | 250 |  |  | 80 | 100 |
|  | 350 |  |  | 88 | 98 |
| Formulation B | 150 | ceteareth-30 | 1:3 | 33 | 73 |
|  | 250 |  |  | 60 | 92 |
|  | 350 |  |  | 94 | 100 |
| Formulation B | 150 | ceteareth-30 | 1:6 | 37 | 73 |
|  | 250 |  |  | 53 | 89 |
|  | 350 |  |  | 88 | 100 |
| Formulation B | 150 | Ethomeen T/25 | 1:0.3 | 67 | 90 |
|  | 250 |  |  | 92 | 99 |
|  | 350 |  |  | 100 | 100 |
| Formulation B | 150 | Ethomeen T/25 | 1:1 | 58 | 94 |
|  | 250 |  |  | 83 | 96 |
|  | 350 |  |  | 93 | 98 |
| Formulation B | 150 | Ethomeen T/25 | 1:1.5 | 50 | 73 |
|  | 250 |  |  | 86 | 100 |
|  | 350 |  |  | 99 | 100 |
| Formulation B | 150 | Ethomeen T/25 | 1:3 | 45 | 83 |
|  | 250 |  |  | 89 | 95 |
|  | 350 |  |  | 100 | 100 |
| Formulation B | 150 | Ethomeen T/25 | 1:6 | 35 | 82 |
|  | 250 |  |  | 73 | 98 |
|  | 350 |  |  | 88 | 98 |

Steareth-20, steareth-30 and ceteareth-30 were more effective additives for Formulation B than steareth-10 in this study.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A plant treatment composition comprising (a) an exogenous chemical and (b) an alkylether surfactant or mixture of such surfactants having the formula

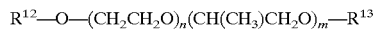

$$R^{12}-O-(CH_2CH_2O)_n(CH(CH_3)CH_2O)_m-R^{13}$$

wherein $R^{12}$ is an alkyl or alkenyl group having about 16 to about 22 carbon atoms, n is an average number of about 20 to about 100, m is an average number of 0 to about 5, and $R^{13}$ is hydrogen or $C_{1-4}$ alkyl, present in an amount such that the weight/weight ratio of said alkylether surfactant or mixture of such surfactants to the exogenous chemical is about 1:3 to about 1:100, wherein if the exogenous chemical is a salt of an acid, the ratio is calculated on an acid equivalent basis.

2. The composition of claim 1 wherein the exogenous chemical is a foliar-applied exogenous chemical.

3. The composition of claim 2 wherein the exogenous chemical is a pesticide, gametocide or plant growth regulator.

4. The composition of claim 3 wherein the exogenous chemical is a herbicide, nematicide or plant growth regulator.

5. The composition of claim 4 wherein the exogenous chemical is a herbicide.

6. The composition of claim 5 wherein the herbicide is selected from the group consisting of acetanilides, bipyridyls, cyclohexenones, dinitroanilines, diphenylethers, fatty acids, hydroxybenzonitriles, imidazolinones, phenoxies, phenoxypropionates, substituted ureas, sulfonylureas, thiocarbamates and triazines.

7. The composition of claim 5 wherein the herbicide is selected from the group consisting of acetochlor, alachlor, metolachlor, aminotriazole, asulam, bentazon, bialaphos, diquat, paraquat, bromacil, clethodim, sethoxydim, dicamba, diflufenican, pendimethalin, acifluorfen, $C_{9-10}$ fatty acids, fomesafen, oxyfluorfen, fosamine, flupoxam, glufosinate, glyphosate, bromoxynil, imazaquin, imazethapyr, isoxaben, norflurazon, 2,4-D, diclofop, fluazifop, quizalofop, picloram, propanil, fluometuron, isoproturon, chlorimuron, chlorsulfuron, halosulfuron, metsulfuron, primisulfuron, sulfometuron, sulfosulfuron, triallate, atrazine, metribuzin, triclopyr and herbicidal derivatives thereof.

8. The composition of claim 7 wherein the herbicide is glyphosate or a herbicidal derivative thereof.

9. The composition of claim 8 wherein the herbicide is glyphosate in its acid form.

10. The composition of claim 4 wherein the exogenous chemical is water-soluble.

11. The composition of claim 10 wherein the exogenous chemical is a salt having an anion portion and a cation portion.

12. The composition of claim 11 wherein at least one of said anion and cation portions is biologically active and has a molecular weight of less than about 300.

13. The composition of claim 12 wherein the exogenous chemical is paraquat or diquat.

14. The composition of claim 12 wherein the exogenous chemical exhibits systemic biological activity in the plant.

15. The composition of claim 14 wherein the exogenous chemical has one or more functional groups selected from the group consisting of amine, amide, carboxylate, phosphonate and phosphinate groups.

16. The composition of claim 15 wherein the exogenous chemical is a salt of 3,4,4-trifluoro-3-butenoic acid or of N-(3,4,4-trifluoro-1-oxo-3-butenyl)glycine that exhibits nematicidal activity.

17. The composition of claim 15 wherein the exogenous chemical is a herbicidal or plant growth regulating compound having at least one of each of amine, carboxylate and either phosphonate or phosphinate functional groups.

18. The composition of claim 17 wherein the herbicidal or plant growth regulating compound is a salt of glufosinate.

19. The composition of claim 18 wherein the salt of glufosinate is the ammonium salt.

20. The composition of claim 17 wherein the herbicidal or plant growth regulating compound is a salt of N-phosphonomethylglycine.

21. The composition of claim 20 wherein the salt of N-phosphonomethylglycine is selected from the group consisting of sodium, potassium, ammonium, mono-, di-, tri- and tetra-$C_{1-4}$-alkylammonium, mono-, di- and tri-$C_{1-4}$-alkanolammonium, mono-, di- and tri-$C_{1-4}$-alkylsulfonium and sulfoxonium salts.

22. The composition of claim 21 wherein the salt of N-phosphonomethylglycine is the ammonium, monoisopropylammonium or trimethylsulfonium salt.

23. The composition of claim 1, wherein the composition is a shelf-stable concentrate composition comprising the exogenous chemical in an amount of about 15 to about 90 percent by weight.

24. The composition of claim 23, wherein the composition is a solid composition comprising the exogenous chemical substance in an amount of about 30 to about 90 percent by weight.

25. The composition of claim 24, wherein the composition is a water-soluble or water-dispersible granular formulation.

26. The composition of claim 23, further comprising a liquid diluent, and wherein the composition comprises the exogenous chemical substance in an amount of about 15 to about 60 percent by weight.

27. The composition of claim 26 wherein the exogenous chemical substance is water-soluble and is present in an aqueous phase of the composition in an amount of about 15 to about 45 percent by weight of the composition.

28. The composition of claim 27, wherein the composition is an emulsion having an oil phase and the first excipient substance is present predominantly in the oil phase.

29. The composition of claim 28, wherein the composition is an oil-in-water emulsion.

30. The composition of claim 28, wherein the composition is a water-in-oil emulsion.

31. The composition of claim 28, wherein the composition is a water-in-oil-in-water multiple emulsion.

32. The composition of claim 28, further comprising a solid inorganic particulate colloidal material.

33. The composition of claim 32, wherein the colloidal material comprises particles having an average surface area of about 50 to about 400 $m^2/g$.

34. The composition of claim 32, wherein the colloidal material comprises particles having an average surface area of about 180 to about 400 $m^2/g$.

35. The composition of claim 32, wherein the colloidal material comprises particles of an inorganic oxide selected from the oxides of silicon, aluminum and titanium.

36. A plant treatment composition comprising (a) glyphosate or a herbicidal derivative thereof and (b) an alkylether surfactant or mixture of such surfactants having the formula

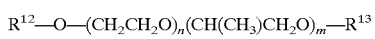

wherein $R^{12}$ is an alkyl or alkenyl group having about 16 to about 22 carbon atoms, n is an average number of about 15 to about 100, m is an average number of 0 to about 5 and $R^{13}$ is hydrogen or $C_{1-4}$ alkyl, present in an amount such that the weight/weight ratio of said alkylether surfactant or mixture of such surfactants to the glyphosate or herbicidal derivative thereof on an acid equivalent basis is about 1:3 to about 1:100.

37. The composition of claim 1 or 36, wherein m is 0 and $R^{13}$ is hydrogen.

38. The composition of claim 1 or 36, wherein n is from about 20 to about 40.

39. The composition of claim 37, wherein $R^{12}$ is a saturated straight-chain alkyl group.

40. The composition of claim 39, wherein the alkylether surfactant is a cetyl or stearyl ether or mixture thereof.

41. The composition of claim 1 or 36, further comprising water and an amount of a solid inorganic particulate colloidal material effective to stabilize the composition, said composition not exhibiting phase separation over a period of time T when stored in a closed container at a temperature in the range from about 15° C. to about 30° C., T being in the range from about 1 hour to about 60 days; wherein the exogenous chemical and the surfactant are present at concentrations in the absolute or relative to each other such that, in the absence of the colloidal material, phase separation would occur during said period of time T.

42. The composition of claim 41 wherein the colloidal material comprises particulates selected from the group consisting of silicon oxides, aluminum oxides, titanium oxides, and mixtures thereof.

43. The composition of claim 41 wherein the particulate colloidal material has an average specific surface area of about 50 to about 400 m²/g.

44. The composition of claim 41 wherein the particulate colloidal material has an average specific surface area of about 180 to about 400 m²/g.

45. The composition of claim 41 wherein the particulate colloidal material has a bimodal distribution of specific surface area whereby a first component of the colloidal material has an average specific surface area of about 50 to about 150 m²/g and a second component of the colloidal material has an average specific surface area of about 180 to about 400 m²/g.

46. The composition of claim 1 or 36, further comprising a compound of formula

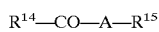

$R^{14}$—CO—A—$R^{15}$ wherein $R^{14}$ is a hydrocarbyl group having about 5 to about 21 carbon atoms, $R^{15}$ is a hydrocarbyl group having 1 to about 14 carbon atoms, the total number of carbon atoms in $R^{14}$ and $R^{15}$ is about 11 to about 27, and A is O or NH.

47. The composition of claim 46 wherein said compound is a $C_{1-4}$ alkyl ester of a $C_{12-18}$ fatty acid.

48. The composition of claim 46 wherein said compound is a $C_{1-4}$ alkyl ester of a $C_{12-18}$ saturated fatty acid.

49. The composition of claim 46 wherein said compound is a propyl, isopropyl or butyl ester of a $C_{12-18}$ fatty acid.

50. The composition of claim 46 wherein said compound is butyl stearate.

51. The composition of claim 46, further comprising water and an amount of a solid inorganic particulate colloidal material effective to stabilize the composition, said composition not exhibiting phase separation over a period of time T when stored in a closed container at a temperature in the range from about 15° C. to about 30° C., T being in the range from about 1 hour to about 60 days; wherein the exogenous chemical and the surfactant are present at concentrations in the absolute or relative to each other such that, in the absence of the colloidal material, phase separation would occur during said period of time T.

52. The composition of claim 51 wherein the colloidal material comprises particulates selected from the group consisting of silicon oxides, aluminum oxides, titanium oxides, and mixtures thereof.

53. The composition of claim 51 wherein the particulate colloidal material has an average specific surface area of about 50 to about 400 m²/g.

54. The composition of claim 51 wherein the particulate colloidal material has an average specific surface area of about 180 to about 400 m²/g.

55. The composition of claim 51 wherein the particulate colloidal material has a bimodal distribution of specific surface area whereby a first component of the colloidal material has an average specific surface area of about 50 to about 150 m²/g and a second component of the colloidal material has an average specific surface area of about 180 to about 400 m²/g.

56. The composition of claim 1 or 36, further comprising water in an amount effective to make the composition a dilute aqueous composition ready for application to foliage of a plant.

57. The composition of claim 36 comprising glyphosate in its acid form.

58. The composition of claim 36 wherein the herbicidal derivative is a salt of N-phosphonomethylglycine.

59. The composition of claim 58 wherein the salt is selected from the group consisting of sodium, potassium, ammonium, mono-, di-, tri- and tetra-$C_{1-4}$-alkylammonium, mono-, di- and tri-$C_{1-4}$-alkanolammonium, mono-, di- and tri-$C_{1-4}$-alkylsulfonium and sulfoxonium salts.

60. The composition of claim 59 wherein the salt of glyphosate is the ammonium, monoisopropylammonium or trimethylsulfonium salt.

61. The composition of claim 36, wherein the composition is a shelf-stable concentrate composition comprising glyphosate or a herbicidal derivative thereof in an amount of about 15 to about 90 percent by weight.

62. The composition of claim 61, wherein the composition is a solid composition comprising glyphosate or a herbicidal derivative thereof in an amount of about 30 to about 90 percent by weight.

63. The composition of claim 62, wherein the composition is a water-soluble or water-dispersible granular formulation.

64. The composition of claim 36, further comprising a liquid diluent, and wherein the composition comprises glyphosate or a herbicidal derivative thereof in an amount of about 15 to about 60 percent by weight.

65. The composition of claim 64 wherein glyphosate or a herbicidal derivative is present in an aqueous phase of the composition in an amount of about 15 to about 45 percent by weight of the composition.

66. The composition of claim 65, wherein the composition is an emulsion having an oil phase and the first excipient substance is present predominantly in the oil phase.

67. The composition of claim 66, wherein the composition is an oil-in-water emulsion.

68. The composition of claim 66, wherein the composition is a water-in-oil emulsion.

69. The composition of claim 66, wherein the composition is a water-in-oil-in-water multiple emulsion.

70. The composition of claim 66, further comprising a solid inorganic particulate colloidal material.

71. The composition of claim 70, wherein the colloidal material comprises particles having an average surface area of about 50 to about 400 m²/g.

72. The composition of claim 70, wherein the colloidal material comprises particles having an average surface area of about 180 to about 400 m²/g.

73. The composition of claim 70, wherein the colloidal material comprises particles of an inorganic oxide selected from the oxides of silicon, aluminum and titanium.

74. A herbicidal composition that comprises
(a) a water soluble salt of N-phosphonomethylglycine, and
(b) an alkylether surfactant or mixture of such surfactants having the formula

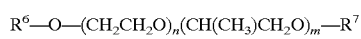

$R^6$—O—$(CH_2CH_2O)_n(CH(CH_3)CH_2O)_m$—$R^7$ wherein $R^6$ is $C_{16}$ or $C_{18}$ alkyl or a mixture thereof, n is an average number of about 20 to about 60, m is an average number from 0 to about 5 and $R^7$ is hydrogen or $C_{1-4}$ alkyl; wherein the weight/weight ratio of said alkylether surfactant or mixture of such surfactants to the N-phosphonomethylglycine on an acid equivalent basis is about 1:3 to about 1:100.

75. A plant treatment method, comprising contacting foliage of a plant with a biologically effective amount of a composition according to any of claims 1, 36, 57–60, or 74.

* * * * *